(12) United States Patent
Lancaster et al.

(10) Patent No.: US 10,597,435 B2
(45) Date of Patent: Mar. 24, 2020

(54) INSULIN-FC FUSIONS AND METHODS OF USE

(71) Applicant: Akston Biosciences Corporation, Beverly, MA (US)

(72) Inventors: Thomas M. Lancaster, Wenham, MA (US); Todd C. Zion, Marblehead, MA (US); Thillainayagam Sathiyaseelan, Lexington, MA (US); Sylaja Murikipudi, Medford, MA (US)

(73) Assignee: Akston Biosciences Corporation, Beverly, MA (US)

( * ) Notice: Subject to any disclaimer, the term of this patent is extended or adjusted under 35 U.S.C. 154(b) by 0 days.

(21) Appl. No.: 16/438,681

(22) Filed: Jun. 12, 2019

(65) Prior Publication Data

US 2019/0315828 A1    Oct. 17, 2019

Related U.S. Application Data

(63) Continuation of application No. 16/468,182, filed as application No. PCT/US2017/065456 on Dec. 8, 2017.

(60) Provisional application No. 62/514,460, filed on Jun. 2, 2017, provisional application No. 62/514,449, filed on Jun. 2, 2017, provisional application No. 62/514,427, filed on Jun. 2, 2017, provisional application No. 62/432,268, filed on Dec. 9, 2016.

(51) Int. Cl.
| | | |
|---|---|---|
| *A61K 38/28* | (2006.01) | |
| *C07K 14/62* | (2006.01) | |
| *A61P 3/10* | (2006.01) | |
| *A61K 38/00* | (2006.01) | |

(52) U.S. Cl.
CPC ............... *C07K 14/62* (2013.01); *A61P 3/10* (2018.01); *A61K 38/00* (2013.01); *C07K 2319/30* (2013.01)

(58) Field of Classification Search
CPC ...................................................... C07K 14/62
See application file for complete search history.

(56) References Cited

U.S. PATENT DOCUMENTS

| | | | |
|---|---|---|---|
| 2003/0040601 A1* | 2/2003 | Diers ..................... | C07K 14/62 530/303 |
| 2013/0190476 A1 | 7/2013 | Lancaster et al. | |
| 2014/0037699 A1 | 2/2014 | Zion et al. | |
| 2014/0302038 A1 | 10/2014 | Dimasi et al. | |
| 2016/0324932 A1 | 11/2016 | Baldwin et al. | |

FOREIGN PATENT DOCUMENTS

CN          103509118 A         1/2014

OTHER PUBLICATIONS

International Searching Authority, International Search Report, PCT/US2017/065456, dated Apr. 9, 2018.
International Searching Authority, Written Opinion of the International Searching Authority, PCT/US2017/065456, dated Apr. 9, 2018.
Wang et al. "Proinsulin-Transferrin Fusion Protein as a Novel Long-Acting Insulin Analog for the Inhibition of Hepatic Glucose Production," Diabetes, Apr. 12, 2014 (Apr. 12, 2014), vol. 63, pp. 1779-1788.

* cited by examiner

*Primary Examiner* — Gyan Chandra
(74) *Attorney, Agent, or Firm* — Reichel Stohry Dean LLP; Mark C. Reichel; Natalie J. Dean

(57) ABSTRACT

The present disclosure relates generally to compositions of insulin-Fc (e.g., proinsulin-Fc) fusion proteins and their use to treat autoimmune disease, e.g., autoimmune diabetes, e.g., Type 1 diabetes.

17 Claims, 20 Drawing Sheets

Specification includes a Sequence Listing.

NO TREATMENT

SEQ ID NO: 3

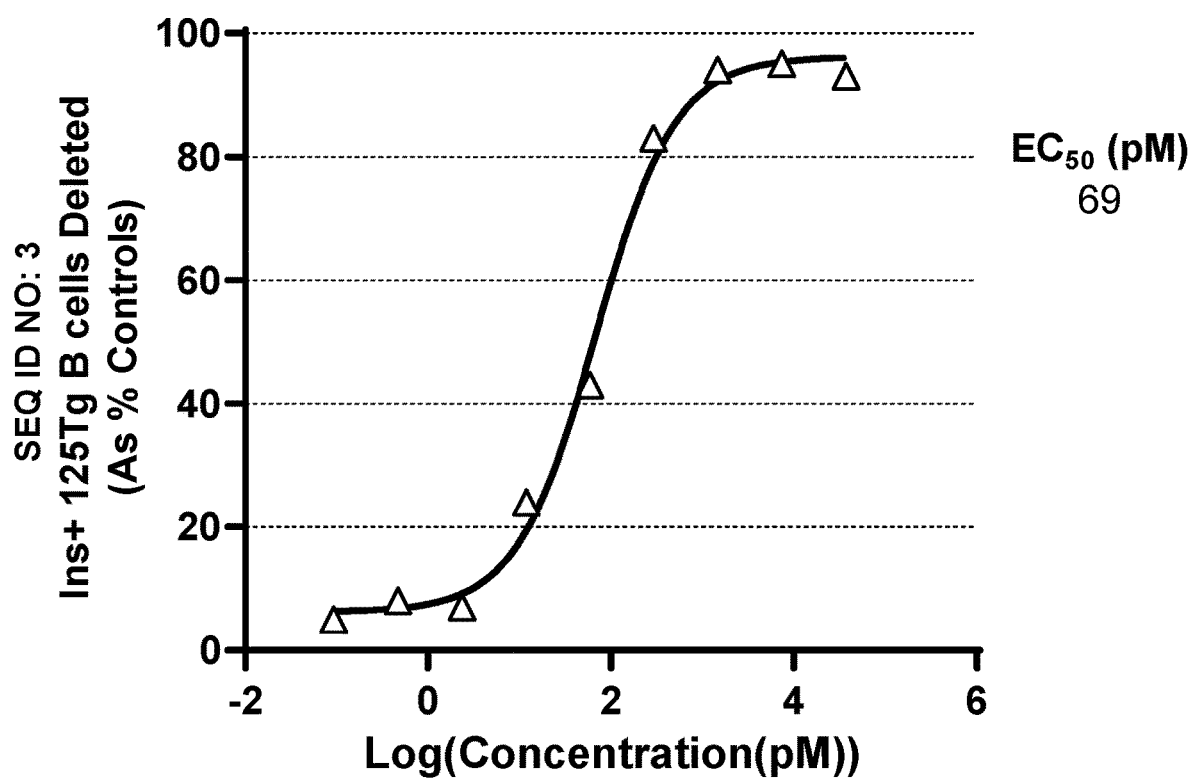
FIGURE 6C (CONTD.)

FIGURE 7C (CONTD.)
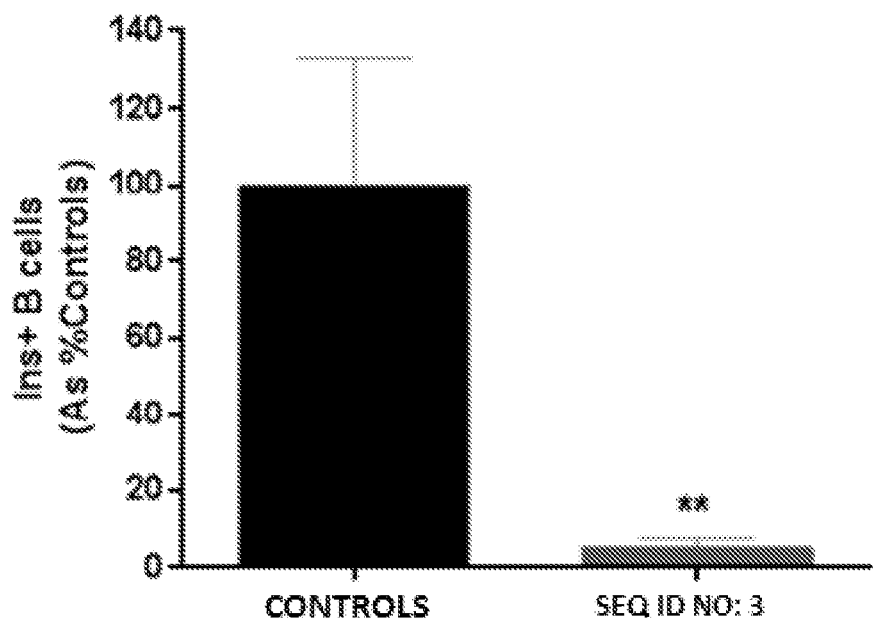
FIGURE 7D
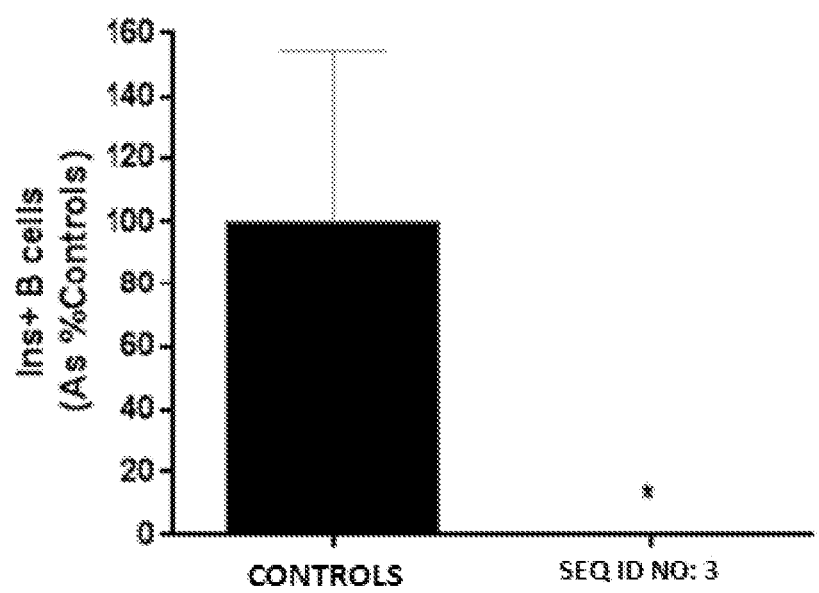

FIGURE 7E (CONTD.)
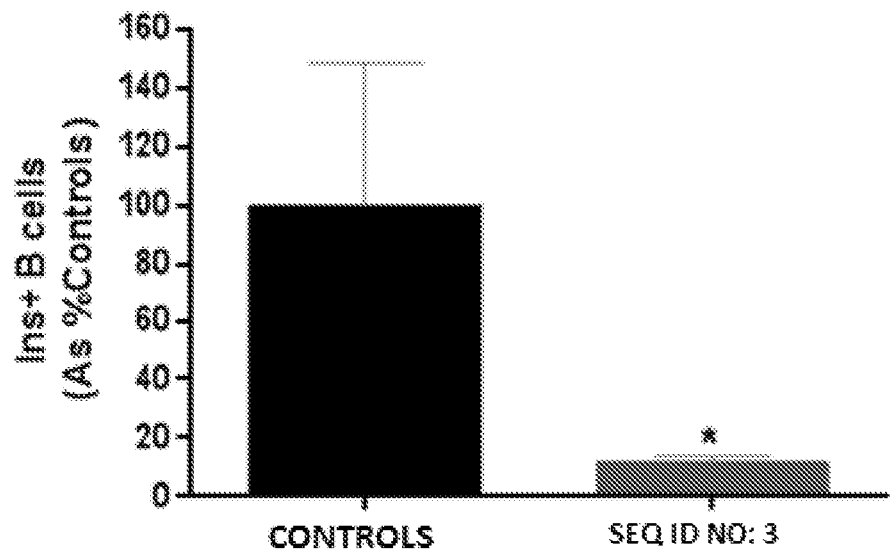
FIGURE 7F
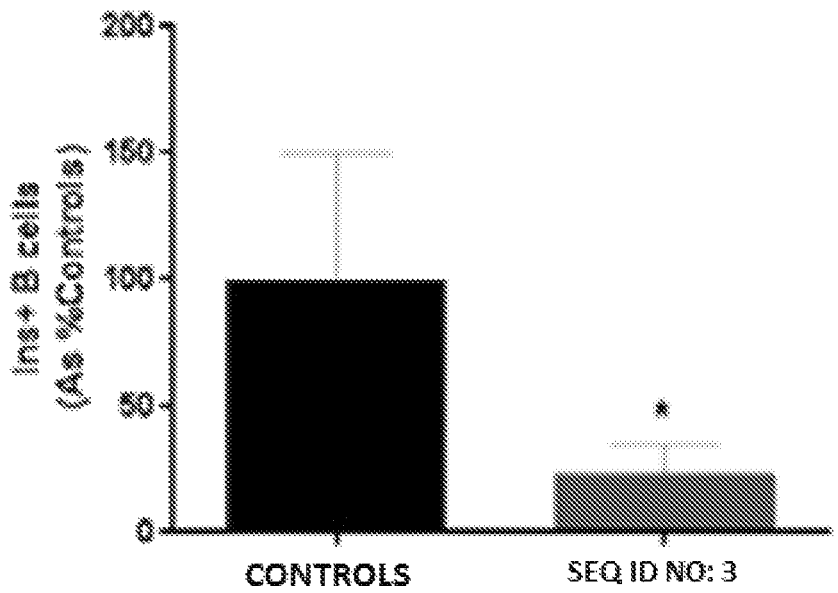

FIGURE 7G (CONTD.)
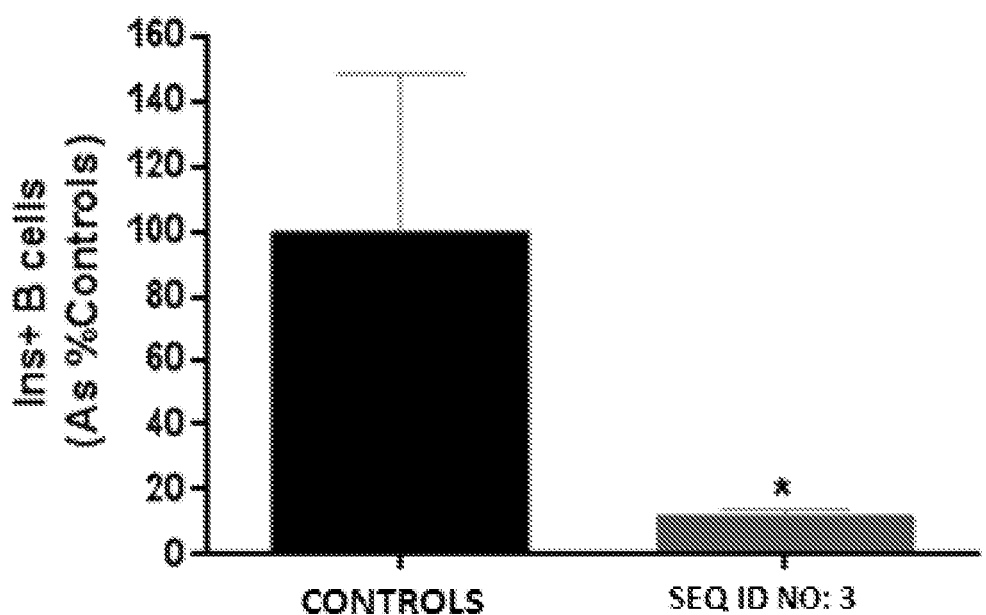
FIGURE 7H
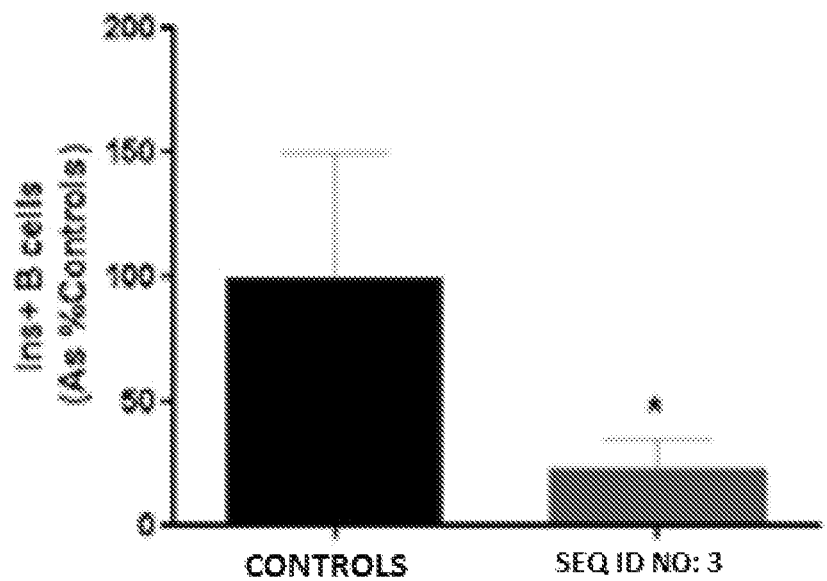

SEQUENCE LISTING

<160> NUMBER OF SEQ ID NOS: 36

<210> SEQ ID NO 1
<211> LENGTH: 1005
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1

```
atggaatgga gctgggtctt tctcttcttc ctgtcagtaa cgactggtgt ccactccttc      60
gtgaagcagc acctgtgcgg ccctcacctg gtggaagctc tgtatctcgt gtgcggcgag     120
cggggcttct tctacacccc caagtctcgg agagaggtgg aagatcccca ggtggaacag     180
```

```
ctggaactgg gcggctctcc tggcgatctg cagacactgg ccctggaagt ggcccggcag    240
aaacggggca tcgtggacca gtgctgcacc tccatctgct ccctgtacca gctggaaaac    300
tactgcaatg gtggaggcgg tggagtgccc agagattgtg gatgtaagcc ttgcatatgt    360
acagtcccag aagtatcatc tgtcttcatc ttccccccaa agcccaagga tgtgctcacc    420
attactctga ctcctaaggt cacgtgtgtt gtggtagaca tcagcaagga tgatcccgag    480
gtccagttca gctggtttgt agatgatgtg gaggtgcaca cagctcagac gcaaccccgg    540
gaggagcagt tcaacagcac tttccgctca gtcagtgaac ttcccatcat gcaccaggac    600
tggctcaatg gcaaggagtt caaatgcagg gtcaacagtg cagctttccc tgcccccatc    660
gagaaaacca tctccaaaac caaggcagac cgaaggctc acaggtgta caccattcca    720
cctcccaagg agcagatggc caaggataaa gtcagtctga cctgcatgat aacagacttc    780
ttccctgaag acattactgt ggagtggcag tggaatgggc agccagcgga gaactacaag    840
aacactcagc ccatcatgga cacagatggc tcttacttcg tctacagcaa gctcaatgtg    900
cagaagagca actgggaggc aggaaatact ttcacctgct ctgtgttaca tgagggcctg    960
cacaaccacc atactgagaa gagcctctcc cactctcctg gttag              1005
```

<210> SEQ ID NO 2
<211> LENGTH: 288
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 2

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Ala Ala Lys
            20                  25                  30

Gly Ile Val Glu Gln Cys Cys Thr Ser Ile Cys Ser Leu Tyr Gln Leu
        35                  40                  45

Glu Asn Tyr Cys Asn Gly Gly Gly Ala Gly Gly Gly Gly Asp Lys
    50                  55                  60

Thr His Thr Cys Pro Pro Cys Pro Ala Pro Glu Leu Leu Gly Gly Pro
65                  70                  75                  80

Ser Val Phe Leu Phe Pro Pro Lys Pro Lys Asp Thr Leu Met Ile Ser
                85                  90                  95

Arg Thr Pro Glu Val Thr Cys Val Val Val Asp Val Ser His Glu Asp
            100                 105                 110

Pro Glu Val Lys Phe Asn Trp Tyr Val Asp Gly Val Glu Val His Asn
        115                 120                 125

Ala Lys Thr Lys Pro Arg Glu Glu Gln Tyr Asn Ser Thr Tyr Arg Val
    130                 135                 140

Val Ser Val Leu Thr Val Leu His Gln Asp Trp Leu Asn Gly Lys Glu
145                 150                 155                 160

Tyr Lys Cys Lys Val Ser Asn Lys Ala Leu Pro Ala Pro Ile Glu Lys
                165                 170                 175

Thr Ile Ser Lys Ala Lys Gly Gln Pro Arg Glu Pro Gln Val Tyr Thr
            180                 185                 190

Leu Pro Pro Ser Arg Asp Glu Leu Thr Lys Asn Gln Val Ser Leu Thr
        195                 200                 205

Cys Leu Val Lys Gly Phe Tyr Pro Ser Asp Ile Ala Val Glu Trp Glu
```

```
            210                 215                 220
Ser Asn Gly Gln Pro Glu Asn Asn Tyr Lys Thr Thr Pro Pro Val Leu
225                 230                 235                 240

Asp Ser Asp Gly Ser Phe Phe Leu Tyr Ser Lys Leu Thr Val Asp Lys
                245                 250                 255

Ser Arg Trp Gln Gln Gly Asn Val Phe Ser Cys Ser Val Met His Glu
            260                 265                 270

Ala Leu His Asn His Tyr Thr Gln Lys Ser Leu Ser Leu Ser Pro Gly
        275                 280                 285

<210> SEQ ID NO 3
<211> LENGTH: 288
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Phe Val Asn Gln His Leu Cys Gly Ser His Leu Val Glu Ala Leu Ala
1               5                   10                  15

Leu Val Cys Gly Glu Arg Gly Phe Phe Tyr Thr Pro Lys Ala Ala Lys
            20                  25                  30

Gly Ile Val Glu Gln Cys Cys Thr Ser Ile Cys Ser Leu Tyr Gln Leu
        35                  40                  45

Glu Asn Tyr Cys Asn Gly Gly Gly Ala Gly Gly Gly Asp Lys
    50                  55                  60

Thr His Thr Cys Pro Pro Cys Pro Ala Pro Glu Leu Leu Gly Gly Pro
65                  70                  75                  80

Ser Val Phe Leu Phe Pro Pro Lys Pro Lys Asp Thr Leu Met Ile Ser
                85                  90                  95

Arg Thr Pro Glu Val Thr Cys Val Val Val Asp Val Ser His Glu Asp
            100                 105                 110

Pro Glu Val Lys Phe Asn Trp Tyr Val Asp Gly Val Glu Val His Asn
        115                 120                 125

Ala Lys Thr Lys Pro Arg Glu Glu Gln Tyr Asn Ser Thr Tyr Arg Val
    130                 135                 140

Val Ser Val Leu Thr Val Leu His Gln Asp Trp Leu Asn Gly Lys Glu
145                 150                 155                 160

Tyr Lys Cys Lys Val Ser Asn Lys Ala Leu Pro Ala Pro Ile Glu Lys
                165                 170                 175

Thr Ile Ser Lys Ala Lys Gly Gln Pro Arg Glu Pro Gln Val Tyr Thr
            180                 185                 190

Leu Pro Pro Ser Arg Asp Glu Leu Thr Lys Asn Gln Val Ser Leu Thr
        195                 200                 205

Cys Leu Val Lys Gly Phe Tyr Pro Ser Asp Ile Ala Val Glu Trp Glu
    210                 215                 220

Ser Asn Gly Gln Pro Glu Asn Asn Tyr Lys Thr Thr Pro Pro Val Leu
225                 230                 235                 240

Asp Ser Asp Gly Ser Phe Phe Leu Tyr Ser Lys Leu Thr Val Asp Lys
                245                 250                 255

Ser Arg Trp Gln Gln Gly Asn Val Phe Ser Cys Ser Val Met His Glu
            260                 265                 270

Ala Leu His Asn His Tyr Thr Gln Lys Ser Leu Ser Leu Ser Pro Gly
        275                 280                 285
```

<210> SEQ ID NO 4
<211> LENGTH: 288
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Phe Val Asn Gln His Leu Cys Gly Ser His Leu Val Gln Ala Leu Tyr
1               5                   10                  15

Leu Val Cys Gly Glu Arg Gly Phe Phe Tyr Thr Pro Lys Ala Ala Lys
            20                  25                  30

Gly Ile Val Glu Gln Cys Cys Thr Ser Ile Cys Ser Leu Tyr Gln Leu
        35                  40                  45

Glu Asn Tyr Cys Asn Gly Gly Gly Ala Gly Gly Gly Gly Asp Lys
    50                  55                  60

Thr His Thr Cys Pro Pro Cys Pro Ala Pro Glu Leu Leu Gly Gly Pro
65                  70                  75                  80

Ser Val Phe Leu Phe Pro Pro Lys Pro Lys Asp Thr Leu Met Ile Ser
                85                  90                  95

Arg Thr Pro Glu Val Thr Cys Val Val Val Asp Val Ser His Glu Asp
            100                 105                 110

Pro Glu Val Lys Phe Asn Trp Tyr Val Asp Gly Val Glu Val His Asn
        115                 120                 125

Ala Lys Thr Lys Pro Arg Glu Glu Gln Tyr Asn Ser Thr Tyr Arg Val
    130                 135                 140

Val Ser Val Leu Thr Val Leu His Gln Asp Trp Leu Asn Gly Lys Glu
145                 150                 155                 160

Tyr Lys Cys Lys Val Ser Asn Lys Ala Leu Pro Ala Pro Ile Glu Lys
                165                 170                 175

Thr Ile Ser Lys Ala Lys Gly Gln Pro Arg Glu Pro Gln Val Tyr Thr
            180                 185                 190

Leu Pro Pro Ser Arg Asp Glu Leu Thr Lys Asn Gln Val Ser Leu Thr
        195                 200                 205

Cys Leu Val Lys Gly Phe Tyr Pro Ser Asp Ile Ala Val Glu Trp Glu
    210                 215                 220

Ser Asn Gly Gln Pro Glu Asn Asn Tyr Lys Thr Thr Pro Pro Val Leu
225                 230                 235                 240

Asp Ser Asp Gly Ser Phe Phe Leu Tyr Ser Lys Leu Thr Val Asp Lys
                245                 250                 255

Ser Arg Trp Gln Gln Gly Asn Val Phe Ser Cys Ser Val Met His Glu
            260                 265                 270

Ala Leu His Asn His Tyr Thr Gln Lys Ser Leu Ser Leu Ser Pro Gly
        275                 280                 285
```

<210> SEQ ID NO 5
<211> LENGTH: 288
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

```
Phe Val Asn Gln His Leu Cys Gly Ser His Leu Val Glu Ala Leu Tyr
1               5                   10                  15
```

Leu Val Cys Gly Glu Glu Gly Phe Phe Tyr Thr Pro Lys Ala Ala Lys
            20                  25                  30

Gly Ile Val Glu Gln Cys Cys Thr Ser Ile Cys Ser Leu Tyr Gln Leu
        35                  40                  45

Glu Asn Tyr Cys Asn Gly Gly Gly Ala Gly Gly Gly Asp Lys
50                  55                  60

Thr His Thr Cys Pro Pro Cys Pro Ala Pro Glu Leu Leu Gly Gly Pro
65                  70                  75                  80

Ser Val Phe Leu Phe Pro Pro Lys Pro Lys Asp Thr Leu Met Ile Ser
                85                  90                  95

Arg Thr Pro Glu Val Thr Cys Val Val Val Asp Val Ser His Glu Asp
            100                 105                 110

Pro Glu Val Lys Phe Asn Trp Tyr Val Asp Gly Val Glu Val His Asn
            115                 120                 125

Ala Lys Thr Lys Pro Arg Glu Glu Gln Tyr Asn Ser Thr Tyr Arg Val
130                 135                 140

Val Ser Val Leu Thr Val Leu His Gln Asp Trp Leu Asn Gly Lys Glu
145                 150                 155                 160

Tyr Lys Cys Lys Val Ser Asn Lys Ala Leu Pro Ala Pro Ile Glu Lys
                165                 170                 175

Thr Ile Ser Lys Ala Lys Gly Gln Pro Arg Glu Pro Gln Val Tyr Thr
            180                 185                 190

Leu Pro Pro Ser Arg Asp Glu Leu Thr Lys Asn Gln Val Ser Leu Thr
            195                 200                 205

Cys Leu Val Lys Gly Phe Tyr Pro Ser Asp Ile Ala Val Glu Trp Glu
210                 215                 220

Ser Asn Gly Gln Pro Glu Asn Asn Tyr Lys Thr Thr Pro Pro Val Leu
225                 230                 235                 240

Asp Ser Asp Gly Ser Phe Phe Leu Tyr Ser Lys Leu Thr Val Asp Lys
                245                 250                 255

Ser Arg Trp Gln Gln Gly Asn Val Phe Ser Cys Ser Val Met His Glu
            260                 265                 270

Ala Leu His Asn His Tyr Thr Gln Lys Ser Leu Ser Leu Ser Pro Gly
            275                 280                 285

<210> SEQ ID NO 6
<211> LENGTH: 288
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Phe Val Asn Gln His Leu Cys Gly Ser His Leu Val Glu Ala Leu Ala
1               5                   10                  15

Leu Val Cys Gly Glu Glu Gly Phe Phe Tyr Thr Pro Lys Ala Ala Lys
            20                  25                  30

Gly Ile Val Glu Gln Cys Cys Thr Ser Ile Cys Ser Leu Tyr Gln Leu
        35                  40                  45

Glu Asn Tyr Cys Asn Gly Gly Gly Ala Gly Gly Gly Asp Lys
    50                  55                  60

Thr His Thr Cys Pro Pro Cys Pro Ala Pro Glu Leu Leu Gly Gly Pro
65                  70                  75                  80

Ser Val Phe Leu Phe Pro Pro Lys Pro Lys Asp Thr Leu Met Ile Ser
                85                  90                  95

```
Arg Thr Pro Glu Val Thr Cys Val Val Val Asp Val Ser His Glu Asp
            100                 105                 110

Pro Glu Val Lys Phe Asn Trp Tyr Val Asp Gly Val Glu Val His Asn
            115                 120                 125

Ala Lys Thr Lys Pro Arg Glu Glu Gln Tyr Asn Ser Thr Tyr Arg Val
130                 135                 140

Val Ser Val Leu Thr Val Leu His Gln Asp Trp Leu Asn Gly Lys Glu
145                 150                 155                 160

Tyr Lys Cys Lys Val Ser Asn Lys Ala Leu Pro Ala Pro Ile Glu Lys
                165                 170                 175

Thr Ile Ser Lys Ala Lys Gly Gln Pro Arg Glu Pro Gln Val Tyr Thr
            180                 185                 190

Leu Pro Pro Ser Arg Asp Glu Leu Thr Lys Asn Gln Val Ser Leu Thr
            195                 200                 205

Cys Leu Val Lys Gly Phe Tyr Pro Ser Asp Ile Ala Val Glu Trp Glu
            210                 215                 220

Ser Asn Gly Gln Pro Glu Asn Asn Tyr Lys Thr Thr Pro Pro Val Leu
225                 230                 235                 240

Asp Ser Asp Gly Ser Phe Phe Leu Tyr Ser Lys Leu Thr Val Asp Lys
                245                 250                 255

Ser Arg Trp Gln Gln Gly Asn Val Phe Ser Cys Ser Val Met His Glu
            260                 265                 270

Ala Leu His Asn His Tyr Thr Gln Lys Ser Leu Ser Leu Ser Pro Gly
            275                 280                 285

<210> SEQ ID NO 7
<211> LENGTH: 279
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Phe Val Asn Gln His Leu Cys Gly Ser His Leu Val Glu Ala Leu Ala
1               5                   10                  15

Leu Val Cys Gly Glu Arg Gly Phe Phe Tyr Thr Pro Lys Ala Ala Lys
            20                  25                  30

Gly Ile Val Glu Gln Cys Cys Thr Ser Ile Cys Ser Leu Tyr Gln Leu
        35                  40                  45

Glu Asn Tyr Cys Asn Asp Lys Thr His Thr Cys Pro Pro Cys Pro Ala
    50                  55                  60

Pro Glu Leu Leu Gly Gly Pro Ser Val Phe Leu Phe Pro Pro Lys Pro
65                  70                  75                  80

Lys Asp Thr Leu Met Ile Ser Arg Thr Pro Glu Val Thr Cys Val Val
                85                  90                  95

Val Asp Val Ser His Glu Asp Pro Glu Val Lys Phe Asn Trp Tyr Val
            100                 105                 110

Asp Gly Val Glu Val His Asn Ala Lys Thr Lys Pro Arg Glu Glu Gln
        115                 120                 125

Tyr Asn Ser Thr Tyr Arg Val Val Ser Val Leu Thr Val Leu His Gln
    130                 135                 140

Asp Trp Leu Asn Gly Lys Glu Tyr Lys Cys Lys Val Ser Asn Lys Ala
145                 150                 155                 160

Leu Pro Ala Pro Ile Glu Lys Thr Ile Ser Lys Ala Lys Gly Gln Pro
```

```
                    165                 170                 175
Arg Glu Pro Gln Val Tyr Thr Leu Pro Pro Ser Arg Asp Glu Leu Thr
                180                 185                 190
Lys Asn Gln Val Ser Leu Thr Cys Leu Val Lys Gly Phe Tyr Pro Ser
            195                 200                 205
Asp Ile Ala Val Glu Trp Glu Ser Asn Gly Gln Pro Glu Asn Asn Tyr
        210                 215                 220
Lys Thr Thr Pro Pro Val Leu Asp Ser Asp Gly Ser Phe Phe Leu Tyr
225                 230                 235                 240
Ser Lys Leu Thr Val Asp Lys Ser Arg Trp Gln Gln Gly Asn Val Phe
                245                 250                 255
Ser Cys Ser Val Met His Glu Ala Leu His Asn His Tyr Thr Gln Lys
                260                 265                 270
Ser Leu Ser Leu Ser Pro Gly
                275

<210> SEQ ID NO 8
<211> LENGTH: 288
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Phe Val Asn Gln His Leu Cys Gly Ser His Leu Val Glu Ala Leu Ala
1               5                   10                  15
Leu Val Cys Gly Glu Arg Gly Phe Phe Tyr Thr Pro Lys Ala Ala Lys
                20                  25                  30
Gly Ile Val Glu Gln Cys Cys Thr Ser Ile Cys Ser Leu Tyr Gln Leu
            35                  40                  45
Glu Asn Tyr Cys Asn Gly Gly Gly Ser Gly Gly Gly Gly Asp Lys
        50                  55                  60
Thr His Thr Cys Pro Pro Cys Pro Ala Pro Glu Leu Leu Gly Gly Pro
65                  70                  75                  80
Ser Val Phe Leu Phe Pro Pro Lys Pro Lys Asp Thr Leu Met Ile Ser
                85                  90                  95
Arg Thr Pro Glu Val Thr Cys Val Val Val Asp Val Ser His Glu Asp
                100                 105                 110
Pro Glu Val Lys Phe Asn Trp Tyr Val Asp Gly Val Glu Val His Asn
            115                 120                 125
Ala Lys Thr Lys Pro Arg Glu Glu Gln Tyr Asn Ser Thr Tyr Arg Val
        130                 135                 140
Val Ser Val Leu Thr Val Leu His Gln Asp Trp Leu Asn Gly Lys Glu
145                 150                 155                 160
Tyr Lys Cys Lys Val Ser Asn Lys Ala Leu Pro Ala Pro Ile Glu Lys
                165                 170                 175
Thr Ile Ser Lys Ala Lys Gly Gln Pro Arg Glu Pro Gln Val Tyr Thr
                180                 185                 190
Leu Pro Pro Ser Arg Asp Glu Leu Thr Lys Asn Gln Val Ser Leu Thr
            195                 200                 205
Cys Leu Val Lys Gly Phe Tyr Pro Ser Asp Ile Ala Val Glu Trp Glu
        210                 215                 220
Ser Asn Gly Gln Pro Glu Asn Asn Tyr Lys Thr Thr Pro Pro Val Leu
225                 230                 235                 240
```

```
Asp Ser Asp Gly Ser Phe Phe Leu Tyr Ser Lys Leu Thr Val Asp Lys
            245                 250                 255

Ser Arg Trp Gln Gln Gly Asn Val Phe Ser Cys Ser Val Met His Glu
        260                 265                 270

Ala Leu His Asn His Tyr Thr Gln Lys Ser Leu Ser Leu Ser Pro Gly
        275                 280                 285

<210> SEQ ID NO 9
<211> LENGTH: 289
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Phe Val Asn Gln His Leu Cys Gly Ser His Leu Val Glu Ala Leu Ala
1               5                   10                  15

Leu Val Cys Gly Glu Arg Gly Phe Phe Tyr Thr Pro Lys Ala Ala Ala
            20                  25                  30

Lys Gly Ile Val Glu Gln Cys Cys Thr Ser Ile Cys Ser Leu Tyr Gln
        35                  40                  45

Leu Glu Asn Tyr Cys Asn Gly Gly Gly Ala Gly Gly Gly Gly Gly Asp
    50                  55                  60

Lys Thr His Thr Cys Pro Pro Cys Pro Ala Pro Glu Leu Leu Gly Gly
65                  70                  75                  80

Pro Ser Val Phe Leu Phe Pro Pro Lys Pro Lys Asp Thr Leu Met Ile
                85                  90                  95

Ser Arg Thr Pro Glu Val Thr Cys Val Val Val Asp Val Ser His Glu
            100                 105                 110

Asp Pro Glu Val Lys Phe Asn Trp Tyr Val Asp Gly Val Glu Val His
        115                 120                 125

Asn Ala Lys Thr Lys Pro Arg Glu Glu Gln Tyr Asn Ser Thr Tyr Arg
    130                 135                 140

Val Val Ser Val Leu Thr Val Leu His Gln Asp Trp Leu Asn Gly Lys
145                 150                 155                 160

Glu Tyr Lys Cys Lys Val Ser Asn Lys Ala Leu Pro Ala Pro Ile Glu
                165                 170                 175

Lys Thr Ile Ser Lys Ala Lys Gly Gln Pro Arg Glu Pro Gln Val Tyr
            180                 185                 190

Thr Leu Pro Pro Ser Arg Asp Glu Leu Thr Lys Asn Gln Val Ser Leu
        195                 200                 205

Thr Cys Leu Val Lys Gly Phe Tyr Pro Ser Asp Ile Ala Val Glu Trp
    210                 215                 220

Glu Ser Asn Gly Gln Pro Glu Asn Asn Tyr Lys Thr Thr Pro Pro Val
225                 230                 235                 240

Leu Asp Ser Asp Gly Ser Phe Phe Leu Tyr Ser Lys Leu Thr Val Asp
                245                 250                 255

Lys Ser Arg Trp Gln Gln Gly Asn Val Phe Ser Cys Ser Val Met His
            260                 265                 270

Glu Ala Leu His Asn His Tyr Thr Gln Lys Ser Leu Ser Leu Ser Pro
        275                 280                 285

Gly

<210> SEQ ID NO 10
<211> LENGTH: 290
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Phe Val Asn Gln His Leu Cys Gly Ser His Leu Val Glu Ala Leu Ala
1               5                   10                  15

Leu Val Cys Gly Glu Arg Gly Phe Phe Tyr Thr Pro Lys Ala Ala Ala
            20                  25                  30

Ala Lys Gly Ile Val Glu Gln Cys Cys Thr Ser Ile Cys Ser Leu Tyr
        35                  40                  45

Gln Leu Glu Asn Tyr Cys Asn Gly Gly Gly Ala Gly Gly Gly Gly
    50                  55                  60

Asp Lys Thr His Thr Cys Pro Pro Cys Pro Ala Pro Glu Leu Leu Gly
65                  70                  75                  80

Gly Pro Ser Val Phe Leu Phe Pro Pro Lys Pro Lys Asp Thr Leu Met
                85                  90                  95

Ile Ser Arg Thr Pro Glu Val Thr Cys Val Val Val Asp Val Ser His
            100                 105                 110

Glu Asp Pro Glu Val Lys Phe Asn Trp Tyr Val Asp Gly Val Glu Val
        115                 120                 125

His Asn Ala Lys Thr Lys Pro Arg Glu Glu Gln Tyr Asn Ser Thr Tyr
    130                 135                 140

Arg Val Val Ser Val Leu Thr Val Leu His Gln Asp Trp Leu Asn Gly
145                 150                 155                 160

Lys Glu Tyr Lys Cys Lys Val Ser Asn Lys Ala Leu Pro Ala Pro Ile
                165                 170                 175

Glu Lys Thr Ile Ser Lys Ala Lys Gly Gln Pro Arg Glu Pro Gln Val
            180                 185                 190

Tyr Thr Leu Pro Pro Ser Arg Asp Glu Leu Thr Lys Asn Gln Val Ser
        195                 200                 205

Leu Thr Cys Leu Val Lys Gly Phe Tyr Pro Ser Asp Ile Ala Val Glu
    210                 215                 220

Trp Glu Ser Asn Gly Gln Pro Glu Asn Asn Tyr Lys Thr Thr Pro Pro
225                 230                 235                 240

Val Leu Asp Ser Asp Gly Ser Phe Phe Leu Tyr Ser Lys Leu Thr Val
                245                 250                 255

Asp Lys Ser Arg Trp Gln Gln Gly Asn Val Phe Ser Cys Ser Val Met
            260                 265                 270

His Glu Ala Leu His Asn His Tyr Thr Gln Lys Ser Leu Ser Leu Ser
        275                 280                 285

Pro Gly
    290

<210> SEQ ID NO 11
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys
            20                  25

<210> SEQ ID NO 12
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Phe Val Asn Gln His Leu Cys Gly Ser His Leu Val Glu Ala Leu Ala
1               5                   10                  15

Leu Val Cys Gly Glu Arg Gly Phe Phe Tyr Thr Pro Lys
            20                  25

<210> SEQ ID NO 13
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Phe Val Asn Gln His Leu Cys Gly Ser His Leu Val Gln Ala Leu Tyr
1               5                   10                  15

Leu Val Cys Gly Glu Arg Gly Phe Phe Tyr Thr Pro Lys
            20                  25

<210> SEQ ID NO 14
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Phe Val Asn Gln His Leu Cys Gly Ser His Leu Val Glu Ala Leu Tyr
1               5                   10                  15

Leu Val Cys Gly Glu Glu Gly Phe Phe Tyr Thr Pro Lys
            20                  25

<210> SEQ ID NO 15
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Phe Val Asn Gln His Leu Cys Gly Ser His Leu Val Glu Ala Leu Ala
1               5                   10                  15

Leu Val Cys Gly Glu Glu Gly Phe Phe Tyr Thr Pro Lys
            20                  25

<210> SEQ ID NO 16
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 16

Ala Ala Lys
1

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ala Ala Ala Lys
1

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ala Ala Ala Ala Lys
1               5

<210> SEQ ID NO 19
<211> LENGTH: 21
<212> TYPE: PRT
<213> ORGANISM: Homo sapiens

<400> SEQUENCE: 19

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Gly Gly Gly Ala Gly Gly Gly Gly
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Gly Gly Gly Ser Gly Gly Gly Gly
1               5

<210> SEQ ID NO 22
<211> LENGTH: 226
```

```
<212> TYPE: PRT
<213> ORGANISM: Homo sapiens

<400> SEQUENCE: 22

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225

<210> SEQ ID NO 23
<211> LENGTH: 227
<212> TYPE: PRT
<213> ORGANISM: Homo sapiens

<400> SEQUENCE: 23

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110
```

```
Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
    210                 215                 220

Pro Gly Lys
225

<210> SEQ ID NO 24
<211> LENGTH: 86
<212> TYPE: PRT
<213> ORGANISM: Homo sapiens

<400> SEQUENCE: 24

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85

<210> SEQ ID NO 25
<211> LENGTH: 30
<212> TYPE: PRT
<213> ORGANISM: Homo sapiens

<400> SEQUENCE: 25

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 26
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Met Glu Trp Ser Trp Val Phe Leu Phe Phe Leu Ser Val Thr Thr Gly
1               5                   10                  15

Val His Ser
```

```
<210> SEQ ID NO 27
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
atggaatgga gctgggtctt tctcttcttc ctgtcagtaa cgactggtgt ccactcc        57

<210> SEQ ID NO 28
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Glu or Gln
<220> FEATURE:
<221> NAME/KEY: MOD_RES
<222> LOCATION: (16)..(16)
<223> OTHER INFORMATION: Tyr or Ala
<220> FEATURE:
<221> NAME/KEY: MOD_RES
<222> LOCATION: (22)..(22)
<223> OTHER INFORMATION: Arg or Glu
<220> FEATURE:
<223> OTHER INFORMATION: See specification as filed for detailed
      description of substitutions and preferred embodiments

<400> SEQUENCE: 28

Phe Val Asn Gln His Leu Cys Gly Ser His Leu Val Xaa Ala Leu Xaa
1               5                   10                  15

Leu Val Cys Gly Glu Xaa Gly Phe Phe Tyr Thr Pro Lys
            20                  25

<210> SEQ ID NO 29
<211> LENGTH: 924
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
atggaatgga gctgggtctt tctcttcttc ctgtcagtaa cgactggtgt ccactccttc        60
gtgaaccagc acctgtgcgg ctcccacctg gtggaagctc tggctctcgt gtgcggcgag       120
cggggcttct tctacacccc caaggccgct aaaggcatcg tgaacagtg ctgcacctcc        180 atctgctccc tgtaccagct ggaaaactac tgcaatggcg aggtggtgc aggaggcggt       240 ggagacaaaa ctcacacatg cccaccgtgc ccagcacctg aactcctggg gggaccgtca       300
gtcttcctct tccccccaaa acccaaggac accctcatga tctcccggac ccctgaggtc       360
acatgcgtgg tggtggacgt gagccacgaa gaccctgagg tcaagttcaa ctggtacgtg       420
gacggcgtgg aggtgcataa tgccaagaca agccgcggg aggagcagta caacagcacg        480
taccgtgtgg tcagcgtcct caccgtcctg caccaggact ggctgaatgg caaggagtac       540
aagtgcaagg tctccaacaa agccctccca gccccatcg agaaaaccat ctccaaagcc       600
aaagggcagc cccgagaacc acaggtgtac accctgcccc catcccggga tgagctgacc       660
```

| | |
|---|---:|
| aagaaccagg tcagcctgac ctgcctggtc aaaggcttct atcccagcga catcgccgtg | 720 |
| gagtgggaga gcaatgggca gccggagaac aactacaaga ccacgcctcc cgtgctggac | 780 |
| tccgacggct ccttcttcct ctacagcaag ctcaccgtgg acaagagcag gtggcagcag | 840 |
| gggaacgtct tctcatgctc cgtgatgcat gaggctctgc acaaccacta cacgcagaag | 900 |
| agcctctccc tgtctccggg ttag | 924 |

<210> SEQ ID NO 30
<211> LENGTH: 924
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 30

| | |
|---|---:|
| atggaatgga gctgggtctt tctcttcttc ctgtcagtaa cgactggtgt ccactccttc | 60 |
| gtgaaccagc acctgtgcgg ctcccacctg gtgcaagctc tgtatctcgt gtgcggcgag | 120 |
| cggggcttct tctacacccc caaggccgct aaaggcatcg tggaacagtg ctgcacctcc | 180 |
| atctgctccc tgtaccagct ggaaaactac tgcaatggcg gaggtggtgc aggaggcggt | 240 |
| ggagacaaaa ctcacacatg cccaccgtgc ccagcacctg aactcctggg gggaccgtca | 300 |
| gtcttcctct tccccccaaa acccaaggac accctcatga tctcccggac ccctgaggtc | 360 |
| acatgcgtgg tggtggacgt gagccacgaa gaccctgagg tcaagttcaa ctggtacgtg | 420 |
| gacggcgtgg aggtgcataa tgccaagaca aagccgcggg aggagcagta caacagcacg | 480 |
| taccgtgtgg tcagcgtcct caccgtcctg caccaggact ggctgaatgg caaggagtac | 540 |
| aagtgcaagg tctccaacaa agccctccca gcccccatcg agaaaaccat ctccaaagcc | 600 |
| aaagggcagc cccgagaacc acaggtgtac accctgcccc catcccggga tgagctgacc | 660 |
| aagaaccagg tcagcctgac ctgcctggtc aaaggcttct atcccagcga catcgccgtg | 720 |
| gagtgggaga gcaatgggca gccggagaac aactacaaga ccacgcctcc cgtgctggac | 780 |
| tccgacggct ccttcttcct ctacagcaag ctcaccgtgg acaagagcag gtggcagcag | 840 |
| gggaacgtct tctcatgctc cgtgatgcat gaggctctgc acaaccacta cacgcagaag | 900 |
| agcctctccc tgtctccggg ttag | 924 |

<210> SEQ ID NO 31
<211> LENGTH: 924
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 31

| | |
|---|---:|
| atggaatgga gctgggtctt tctcttcttc ctgtcagtaa cgactggtgt ccactccttc | 60 |
| gtgaaccagc acctgtgcgg ctcccacctg gtggaagctc tgtatctcgt gtgcggcgag | 120 |
| gagggcttct tctacacccc caaggccgct aaaggcatcg tggaacagtg ctgcacctcc | 180 |
| atctgctccc tgtaccagct ggaaaactac tgcaatggcg gaggtggtgc aggaggcggt | 240 |
| ggagacaaaa ctcacacatg cccaccgtgc ccagcacctg aactcctggg gggaccgtca | 300 |
| gtcttcctct tccccccaaa acccaaggac accctcatga tctcccggac ccctgaggtc | 360 |
| acatgcgtgg tggtggacgt gagccacgaa gaccctgagg tcaagttcaa ctggtacgtg | 420 |
| gacggcgtgg aggtgcataa tgccaagaca aagccgcggg aggagcagta caacagcacg | 480 |

```
taccgtgtgg tcagcgtcct caccgtcctg caccaggact ggctgaatgg caaggagtac    540
aagtgcaagg tctccaacaa agccctccca gcccccatcg agaaaaccat ctccaaagcc    600
aaagggcagc cccgagaacc acaggtgtac accctgcccc catcccggga tgagctgacc    660
aagaaccagg tcagcctgac ctgcctggtc aaaggcttct atcccagcga catcgccgtg    720
gagtgggaga gcaatgggca gccggagaac aactacaaga ccacgcctcc cgtgctggac    780
tccgacggct ccttcttcct ctacagcaag ctcaccgtgg acaagagcag gtggcagcag    840
gggaacgtct tctcatgctc cgtgatgcat gaggctctgc acaaccacta cacgcagaag    900
agcctctccc tgtctccggg ttag                                           924

<210> SEQ ID NO 32
<211> LENGTH: 924
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
atggaatgga gctgggtctt tctcttcttc ctgtcagtaa cgactggtgt ccactccttc     60
gtgaaccagc acctgtgcgg ctcccacctg gtggaagctc tggctctcgt gtgcggcgag    120
gagggcttct tctacacccc caaggccgct aaaggcatcg tggaacagtg ctgcacctcc    180
atctgctccc tgtaccagct ggaaaactac tgcaatggcg aggtggtgc aggaggcggt    240 ggagacaaaa ctcacacatg cccaccgtgc ccagcacctg aactcctggg gggaccgtca    300
gtcttcctct tccccccaaa acccaaggac accctcatga tctcccggac ccctgaggtc    360
acatgcgtgg tggtggacgt gagccacgaa gaccctgagg tcaagttcaa ctggtacgtg    420
gacggcgtgg aggtgcataa tgccaagaca aagccgcggg aggagcagta caacagcacg    480
taccgtgtgg tcagcgtcct caccgtcctg caccaggact ggctgaatgg caaggagtac    540
aagtgcaagg tctccaacaa agccctccca gcccccatcg agaaaaccat ctccaaagcc    600
aaagggcagc cccgagaacc acaggtgtac accctgcccc catcccggga tgagctgacc    660
aagaaccagg tcagcctgac ctgcctggtc aaaggcttct atcccagcga catcgccgtg    720
gagtgggaga gcaatgggca gccggagaac aactacaaga ccacgcctcc cgtgctggac    780
tccgacggct ccttcttcct ctacagcaag ctcaccgtgg acaagagcag gtggcagcag    840
gggaacgtct tctcatgctc cgtgatgcat gaggctctgc acaaccacta cacgcagaag    900
agcctctccc tgtctccggg ttag                                           924

<210> SEQ ID NO 33
<211> LENGTH: 897
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
atggaatgga gctgggtctt tctcttcttc ctgtcagtaa cgactggtgt ccactccttc     60
gtgaaccagc acctgtgcgg ctcccacctg gtggaagctc tggctctcgt gtgcggcgag    120
cggggcttct tctacacccc caaggccgct aaaggcatcg tggaacagtg ctgcacctcc    180
atctgctccc tgtaccagct ggaaaactac tgcaatgaca aaaactcacac atgcccaccg    240
```

```
tgcccagcac ctgaactcct ggggggaccg tcagtcttcc tcttccccc aaaacccaag      300 gacaccctca tgatctcccg gacccctgag gtcacatgcg tggtggtgga cgtgagccac      360
gaagaccctg aggtcaagtt caactggtac gtggacggcg tggaggtgca taatgccaag      420
acaaagccgc gggaggagca gtacaacagc acgtaccgtg tggtcagcgt cctcaccgtc      480
ctgcaccagg actggctgaa tggcaaggag tacaagtgca aggtctccaa caaagccctc      540
ccagccccca tcgagaaaac catctccaaa gccaaagggc agccccgaga accacaggtg      600
tacaccctgc ccccatcccg ggatgagctg accaagaacc aggtcagcct gacctgcctg      660
gtcaaaggct tctatcccag cgacatcgcc gtggagtggg agagcaatgg gcagccggag      720
aacaactaca agaccacgcc tcccgtgctg gactccgacg gctccttctt cctctacagc      780
aagctcaccg tggacaagag caggtggcag caggggaacg tcttctcatg ctccgtgatg      840
catgaggctc tgcacaacca ctacacgcag aagagcctct ccctgtctcc gggttag       897

<210> SEQ ID NO 34
<211> LENGTH: 924
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
atggaatgga gctgggtctt tctcttcttc ctgtcagtaa cgactggtgt ccactccttc       60
gtgaaccagc acctgtgcgg ctcccacctg gtggaagctc tggctctcgt gtgcggcgag      120
cggggcttct tctacacccc caaggccgct aaaggcatcg tggaacagtg ctgcacctcc      180
atctgctccc tgtaccagct ggaaaactac tgcaatggcg aggtggttc aggaggcggt      240 ggagacaaaa ctcacacatg cccaccgtgc ccagcacctg aactcctggg gggaccgtca      300
gtcttcctct tccccccaaa acccaaggac accctcatga tctcccggac ccctgaggtc      360
acatgcgtgg tggtggacgt gagccacgaa gaccctgagg tcaagttcaa ctggtacgtg      420
gacggcgtgg aggtgcataa tgccaagaca aagccgcggg aggagcagta caacagcacg      480
taccgtgtgg tcagcgtcct caccgtcctg caccaggact ggctgaatgg caaggagtac      540
aagtgcaagg tctccaacaa agccctccca gcccccatcg agaaaaccat ctccaaagcc      600
aaagggcagc cccgagaacc acaggtgtac accctgcccc catcccggga tgagctgacc      660
aagaaccagg tcagcctgac ctgcctggtc aaaggcttct atcccagcga catcgccgtg      720
gagtgggaga gcaatgggca gccggagaac aactacaaga ccacgcctcc cgtgctggac      780
tccgacggct ccttcttcct ctacagcaag ctcaccgtgg acaagagcag gtggcagcag      840
gggaacgtct tctcatgctc cgtgatgcat gaggctctgc acaaccacta cacgcagaag      900
agcctctccc tgtctccggg ttag                                            924

<210> SEQ ID NO 35
<211> LENGTH: 927
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
atggaatgga gctgggtctt tctcttcttc ctgtcagtaa cgactggtgt ccactccttc       60
gtgaaccagc acctgtgcgg ctcccacctg gtggaagctc tggctctcgt gtgcggcgag      120
```

```
cggggcttct tctacacccc caaggccgct gcaaaaggca tcgtggaaca gtgctgcacc        180
tccatctgct ccctgtacca gctggaaaac tactgcaatg gcggaggtgg tgcaggaggc        240
ggtggagaca aaactcacac atgcccaccg tgcccagcac ctgaactcct gggggaccg        300 tcagtcttcc tcttccccc aaacccaag gacacccta tgatctcccg gacccctgag        360
gtcacatgcg tggtggtgga cgtgagccac gaagaccctg aggtcaagtt caactggtac        420
gtggacggcg tggaggtgca taatgccaag acaaagccgc gggaggagca gtacaacagc        480
acgtaccgtg tggtcagcgt cctcaccgtc ctgcaccagg actggctgaa tggcaaggag        540
tacaagtgca aggtctccaa caaagccctc cagccccca tcgagaaaac catctccaaa        600 gccaagggc agccccgaga accacaggtg tacaccctgc cccatcccg ggatgagctg        660 accaagaacc aggtcagcct gacctgcctg gtcaaaggct tctatcccag cgacatcgcc        720
gtggagtggg agagcaatgg gcagccggag aacaactaca agaccacgcc tcccgtgctg        780
gactccgacg gctccttctt cctctacagc aagctcaccg tggacaagag caggtggcag        840
caggggaacg tcttctcatg ctccgtgatg catgaggctc tgcacaacca ctacacgcag        900
aagagcctct ccctgtctcc gggttag                                            927

<210> SEQ ID NO 36
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
atggaatgga gctgggtctt tctcttcttc ctgtcagtaa cgactggtgt ccactccttc         60
gtgaaccagc acctgtgcgg ctcccacctg gtggaagctc tggctctcgt gtgcggcgag        120
cggggcttct tctacacccc caaggccgct gcagctaaag gcatcgtgga acagtgctgc        180
acctccatct gctccctgta ccagctggaa aactactgca atggcggagg tggtgcagga        240
ggcggtggag acaaaactca cacatgccca ccgtgcccag cacctgaact cctggggga        300 ccgtcagtct tcctcttccc cccaaaaccc aaggacaccc tcatgatctc ccggacccct        360
gaggtcacat gcgtggtggt ggacgtgagc cacgaagacc ctgaggtcaa gttcaactgg        420
tacgtggacg gcgtggaggt gcataatgcc aagacaaagc cgcgggagga gcagtacaac        480
agcacgtacc gtgtggtcag cgtcctcacc gtcctgcacc aggactggct gaatggcaag        540
gagtacaagt gcaaggtctc caacaaagcc ctcccagccc ccatcgagaa aaccatctcc        600
aaagccaaag gcagccccg agaaccacag gtgtacaccc tgcccccatc ccgggatgag        660
ctgaccaaga accaggtcag cctgacctgc ctggtcaaag gcttctatcc cagcgacatc        720
gccgtggagt gggagagcaa tgggcagccg gagaacaact acaagaccac gcctcccgtg        780
ctggactccg acggctcctt cttcctctac agcaagctca ccgtggacaa gagcaggtgg        840
cagcagggga acgtcttctc atgctccgtg atgcatgagg ctctgcacaa ccactacacg        900
cagaagagcc tctccctgtc tccgggttag                                         930
```

US 10,597,435 B2

INSULIN-FC FUSIONS AND METHODS OF USE

PRIORITY AND CROSS-REFERENCE TO RELATED APPLICATIONS

The present application is related to, claims the priority benefit of, and is a U.S. continuation patent application of, U.S. patent application Ser. No. 16/468,182, filed Jun. 10, 2019, which is related to, claims the priority benefit of, and is a U.S. 35 U.S.C. 371 national stage patent application of, International Patent Application Serial No. PCT/US2017/065456, filed Dec. 8, 2017, which is related to and claims the benefit of and priority to U.S. Provisional Patent Application Ser. No. 62/432,268, filed Dec. 9, 2016, U.S. Provisional Patent Application Ser. No. 62/514,427, filed Jun. 2, 2017, U.S. Provisional Patent Application Ser. No. 62/514,449, filed Jun. 2, 2017, and U.S. Provisional Patent Application Ser. No. 62/514,460, filed on Jun. 2, 2017, the contents of which are incorporated herein by reference in their entireties. This application claims the benefit of and priority to U.S. Application No. 62/432,268, filed Dec. 9, 2016, U.S. Application No. 62/514,427, filed Jun. 2, 2017, U.S. Application No. 62/514,449, filed Jun. 2, 2017, and U.S. Application No. 62/514,460, filed on Jun. 2, 2017, the contents of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Jan. 16, 2019, is named 116603-0130_SL.txt and is 45,990 bytes in size.

TECHNICAL FIELD

The present technology relates to compositions of insulin-Fc (e.g., proinsulin-Fc) fusion proteins and their use to treat autoimmune disease, e.g., autoimmune diabetes, e.g., Type 1 diabetes.

BACKGROUND

The following description of the background of the present technology is provided simply as an aid in understanding the present technology and is not admitted to describe or constitute prior art to the present technology.

Autoimmune diabetes, e.g., Type 1 diabetes (T1D), is a form of diabetes in which the immune system attacks and destroys the insulin producing β-cells of the pancreas. The resulting lack of insulin leads to increased levels of glucose in the blood and urine of patients, which contributes to a number of serious long term complications including heart disease, kidney disease, stroke, neuropathy, skin ulcers, and blindness (*Diabetes Care* (2013) 36, 1033-1044). The global prevalence of diabetes is estimated to be roughly 9% among adults over 18 years of age, and is expected to rise to 10% of the worldwide adult population by 2030 (*Diabetes Voice*, Global Perspective on Diabetes, 2011). In the United States, more than 15,000 children and 15,000 adults are diagnosed with Type I diabetes each year. It has been estimated that T1D accounts for nearly 9% of the economic burden of diagnosed diabetes including Type 1 and Type 2 in the United States (Dall, T. M. et al, *Popul Health Manag* (2009) 12, 103-110), or approximately $20 billion per year in direct medical and indirect costs (*Diabetes Care* 36 (2013), 1033-1044).

Current treatment fails to normalize blood glucose levels, leading to a host of diabetic complications. Therefore, there is a need for more cost effective and less burdensome treatment options for this disease.

SUMMARY OF THE PRESENT TECHNOLOGY

In one aspect, the present disclosure provides an insulin-Fc fusion protein comprising an insulin polypeptide fused to a Fc domain, wherein the insulin polypeptide comprises a B-chain peptide, a C-chain peptide, and an A-chain peptide, and wherein the amino acid sequence of the C-chain peptide is AAK (SEQ ID NO: 16). In some embodiments, the insulin-Fc fusion protein binds human insulin receptor at an $IC_{50}$>5,000 nM in a competitive binding assay. Additionally or alternatively, in some embodiments, the insulin-Fc fusion protein inhibits in vitro binding of insulin$^+$ B cell receptors to insulin at an $IC_{50}$≤100 nM. Additionally or alternatively, in some embodiments, the insulin-Fc fusion protein activates T-cells to secrete IL-2 levels that are reduced compared to that observed in T-cells activated by recombinant human insulin. In some embodiments, the insulin-Fc fusion protein activates T-cells to secrete IL-2 levels that are less than 3,000 pg/ml.

In certain embodiments, the insulin polypeptide is a proinsulin polypeptide or a preproinsulin polypeptide. In some embodiments of the insulin-Fc fusion protein, the amino acid sequence of the A-chain peptide comprises SEQ ID NO: 19. The insulin polypeptide may be fused to the Fc fragment via a peptide linker. Examples of peptide linkers include SEQ ID NO: 20 and SEQ ID NO: 21. Alternatively, no peptide linker may be present between the insulin polypeptide and the Fc domain of the insulin-Fc fusion protein (e.g., the C-terminal region of the insulin polypeptide is covalently linked (e.g., via a peptide bond) to the N-terminal region of the Fc domain or the N-terminal region of the insulin polypeptide is covalently linked (e.g., via a peptide bond) to the C-terminal region of the Fc domain, e.g., SEQ ID NO: 7). Additionally or alternatively, in some embodiments of the insulin-Fc fusion protein, the Fc domain comprises a wild-type Fc fragment of human $IgG_1$. In certain embodiments, the amino acid sequence of the Fc domain comprises SEQ ID NO: 22.

Additionally or alternatively, in any of the above embodiments of the insulin-Fc fusion protein, the orientation of the insulin polypeptide from N- to C-termini is: (N-terminus)-B-chain peptide-C-chain peptide-A-chain peptide-(C-terminus). The insulin polypeptide may be located at the N-terminus or C-terminus of the Fc domain.

Additionally or alternatively, in any of the above embodiments of the insulin-Fc fusion protein, the B-chain peptide comprises the amino acid sequence FVNQHLCGSHLVX$_1$ALX$_2$LVCGEX$_3$GFFYTPK (SEQ ID NO: 28), wherein X$_1$ is E or Q, X$_2$ is Y or A, and X$_3$ is R or E. In certain embodiments, X$_2$ is A.

In one aspect, the present disclosure provides an insulin-Fc fusion protein comprising an insulin polypeptide fused to a Fc domain, wherein the insulin polypeptide comprises a B-chain peptide, a C-chain peptide, and an A-chain peptide, wherein the B-chain peptide comprises the amino acid sequence FVNQHLCGSHLVX$_1$ALX$_2$LVCGEX$_3$GFFYTPK (SEQ ID NO: 28), wherein X$_1$ is E or Q, X$_2$ is Y or A, and X$_3$ is R or E; and wherein the amino acid sequence of the C-chain peptide is AAK (SEQ ID NO: 16). In some embodiments, $X_2$ is A.

In certain embodiments of the insulin-Fc fusion protein, the insulin polypeptide is a proinsulin polypeptide or a preproinsulin polypeptide. In some embodiments of the insulin-Fc fusion protein, the amino acid sequence of the A-chain peptide comprises SEQ ID NO: 19. The insulin polypeptide may be fused to the Fc fragment via a peptide linker. Examples of peptide linkers include SEQ ID NO: 20 and SEQ ID NO: 21. Alternatively, no peptide linker may be present between the insulin polypeptide and the Fc domain of the insulin-Fc fusion protein. Additionally or alternatively, in some embodiments of the insulin-Fc fusion protein, the Fc domain comprises a wild-type Fc fragment of human $IgG_1$. In certain embodiments, the amino acid sequence of the Fc domain comprises SEQ ID NO: 22.

Additionally or alternatively, in some embodiments, the amino acid sequence of the insulin-Fc fusion protein is SEQ ID NO: 2, SEQ ID NO: 3, SEQ ID NO: 4, SEQ ID NO: 5, SEQ ID NO: 6, SEQ ID NO: 7, or SEQ ID NO: 8.

Additionally or alternatively, in any of the above embodiments of the insulin-Fc fusion protein, the orientation of the insulin polypeptide from N- to C-termini is: (N-terminus)-B-chain peptide-C-chain peptide-A-chain peptide-(C-terminus). The insulin polypeptide may be located at the N-terminus or C-terminus of the Fc domain.

In another aspect, the present disclosure provides a recombinant nucleic acid sequence (e.g., mRNA, cDNA, DNA) encoding an insulin-Fc fusion protein selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10 or the nucleic acid sequence of SEQ ID NO: 1, SEQ ID NO: 29, SEQ ID NO: 30, SEQ ID NO: 31, SEQ ID NO: 32, SEQ ID NO: 33, SEQ ID NO: 34, SEQ ID NO: 35, and SEQ ID NO: 36.

In one aspect, the present disclosure provides vectors comprising the recombinant nucleic acid sequences disclosed herein, as well as engineered eukaryotic cells that comprise such vectors (e.g., transfected with a recombinant nucleic acid sequence (e.g., mRNA, cDNA, DNA) encoding an insulin-Fc fusion protein described herein.

In another aspect, the present disclosure provides methods for treating or preventing autoimmune diabetes in a subject in need thereof comprising administering to the subject an effective amount of the insulin-Fc fusion proteins of the present technology. Autoimmune diabetes may comprise Type 1 diabetes, juvenile diabetes, insulin-dependent diabetes, or latent autoimmune diabetes.

In some embodiments of the methods disclosed herein, the subject has been diagnosed with or is at risk for autoimmune diabetes. In some embodiments, the subject has been diagnosed with autoimmune diabetes for less than 3 months, less than 6 months, less than 9 months, less than 1 year, or less than 1.5 years.

Additionally or alternatively, in some embodiments of the methods disclosed herein, the subject has detectable levels of at least one autoimmune antibody but does not have hyperglycemia. In some embodiments, the at least one autoimmune antibody is selected from the group consisting of an insulin autoantibody (IAA), an anti-glutamic acid decarboxylase (GAD) antibody, and an anti-islet antigen-2 (IA-2) antibody. In other embodiments, the subject lacks detectable levels of insulin autoantibody (IAA), anti-glutamic acid decarboxylase (GAD) antibody, and anti-islet antigen-2 (IA-2) antibody.

Additionally or alternatively, in some embodiments of the methods disclosed herein, the subject has detectable levels of a pathogenic B cell population or a disease-causing B cell population (e.g., anti-insulin B cells, insulin-specific B cells, or insulin$^+$ B cells). In other embodiments, the subject lacks detectable levels of a pathogenic B cell population or a disease-causing B cell population (e.g., anti-insulin B cells, insulin-specific B cells, or insulin$^+$ B cells).

Additionally or alternatively, in some embodiments of the methods disclosed herein, the subject harbors one or more human leukocyte antigen (HLA) haplotypes selected from the group consisting of: (a) DRB1*0301-DQA1*0501-DQB1*0201; (b) DRB1*0405-DQA1*0301-DQB1*0302; (c) DRB1*0401-DQA1*0301-DQB*0302; (d) DRB1*0402-DQA1*0301-DQB1*0302; (e) DRB1*0404-DQA1*0301-DQB1*0302; and (f) DRB1*0801-DQB1*0401-DQB1*0402.

Additionally or alternatively, in some embodiments of the methods disclosed herein, the insulin-Fc fusion protein is administered parenterally, intravenously or subcutaneously. In some embodiments, the insulin-Fc fusion protein is administered as an injectable depot formulation. In other embodiments, the insulin-Fc fusion protein is administered as a bolus infusion or an intravenous push. In certain embodiments, the insulin-Fc fusion protein is administered through syringe injection, pump, pen, needle, or indwelling catheter. The insulin-Fc fusion protein may be administered as a single dose or in multiple doses. In certain embodiments, the insulin-Fc fusion protein is administered daily, twice daily, twice weekly, or at least weekly to the subject.

Additionally or alternatively, in some embodiments of the methods disclosed herein, administration of the insulin-Fc fusion protein results in a reduced number of anti-insulin B cells in the subject (e.g., in blood or spleen) compared to that observed in the subject prior to administration (e.g., reduction by at least 5%, e.g., at least 5%, 10%, 15%, 20%, 30%, 40%, 50%, 60%, 70%, 80%, 90%, 100%, 2-fold, 3-fold, 4-fold, 5-fold, 10-fold, or more). The insulin-Fc fusion protein may be administered once or multiple times. In certain embodiments, administration of the insulin-Fc fusion protein does not substantially reduce the number of B cells other than anti-insulin B cells. In some embodiments of the methods disclosed herein, the subject displays a reduction in the number of anti-insulin B cells 1 day, 2 days, 3 days, 4 days, 5 days, 6 days, 7 days, 8 days, 9 days, 10 days, 11 days, 12 days, 13 days, 2 weeks, 3 weeks, or more than 3 weeks after administration of the insulin-Fc fusion protein compared to that observed in the subject prior to administration.

Additionally or alternatively, in some embodiments of the methods disclosed herein, administration of the insulin-Fc fusion protein results in decreased levels of insulin autoantibody in the subject (e.g., circulating IAA) compared to that observed in the subject prior to administration (e.g., a decrease of at least 5%). In some embodiments of the methods disclosed herein, the subject displays decreased levels of insulin autoantibody 1 day, 2 days, 3 days, 4 days, 5 days, 6 days, 7 days, 8 days, 9 days, 10 days, 11 days, 12 days, 13 days, 2 weeks, 3 weeks, or more than 3 weeks after administration of the insulin-Fc fusion protein compared to that observed in the subject prior to administration. The insulin-Fc fusion protein may be administered once or multiple times.

Additionally or alternatively, in some embodiments of the methods disclosed herein, the blood glucose levels of the subject after administration of the insulin-Fc fusion protein are comparable to that observed in the subject prior to administration. In some embodiments of the methods disclosed herein, the blood glucose levels of the subject 1 day, 2 days, 3 days, 4 days, 5 days, 6 days, 7 days, 8 days, 9 days, 10 days, 11 days, 12 days, 13 days, 2 weeks, 3 weeks, or more than 3 weeks after administration of the insulin-Fc fusion protein are comparable to that observed in the subject prior to administration. The insulin-Fc fusion protein may be administered once or multiple times.

In any of the above embodiments, the subject has an endogenous C-peptide level, e.g., before the administration of the insulin-Fc fusion protein, that is (i) greater than or equal to 0.25 nmol/L (e.g., greater than or equal to 0.4, 0.6, 1, 1.5 nmol/L or greater); and/or (ii) greater than or equal to about 90%, 50%, 25%, or 10% relative to a reference standard e.g., before treatment with an insulin-Fc fusion protein described herein. In some embodiments, the glucose lowering activity of the insulin-Fc fusion protein is lower than a reference standard, such as human insulin.

Also disclosed herein are kits comprising the insulin-Fc fusion protein of the present technology, and instructions for use.

BRIEF DESCRIPTION OF THE DRAWINGS

FIG. 6C shows a dose response curve of an exemplary insulin-Fc protein (SEQ ID NO: 3) and its corresponding activity in deleting insulin$^+$ B cells from 125Tg splenocyte/rat AM co-cultures.

FIGS. 7A-7H are a series of graphs showing in vivo cell reduction data following a two-week dosing regimen of an exemplary insulin-Fc fusion protein (SEQ ID NO: 3) in VH125 NOD mice. FIG. 7A is a graph showing the insulin$^+$ B cells in blood as a percent of vehicle-treated controls; FIG. 7B is a graph showing the insulin(−) B cells in blood as a percent of controls; FIG. 7C is a graph showing the insulin$^+$ B cells in spleen (all splenic compartments) as a percent of controls; FIG. 7D shows the insulin$^+$ B cells in the marginal zone spleen population ($CD21^{High}$ $CD23^{High}$); FIG. 7E shows the insulin$^+$ B cells in the follicular spleen population ($IgM^{M1d}$ $CD21^{mid}$); FIG. 7F shows the insulin$^+$ B cells in the T1 spleen population ($CD21^{Low}$ $CD23^{Low}$); FIG. 7G shows the insulin$^+$ B cells in the T2 spleen population ($IgM^{High}$ $CD21^{Mid}$); and FIG. 7H shows the insulin$^+$ B cells in the pre-marginal zone spleen population ($IgM^{High}$ $CD21^{High}$).

FIG. 8A shows in vivo $IgM^{HI}$ insulin$^+$ B cell reduction data in the bone marrow compartment following a 34-week dosing regimen of an exemplary insulin-Fc fusion protein (SEQ ID NO: 3) in VH125 NOD mice; FIG. 8B show in vivo $IgM^{HI}$ insulin$^+$ B cell reduction data in the lymph node compartment following a 34-week dosing regimen of an exemplary insulin-Fc fusion protein (SEQ ID NO: 3) in VH125 NOD mice.

DETAILED DESCRIPTION

Figure 1A:
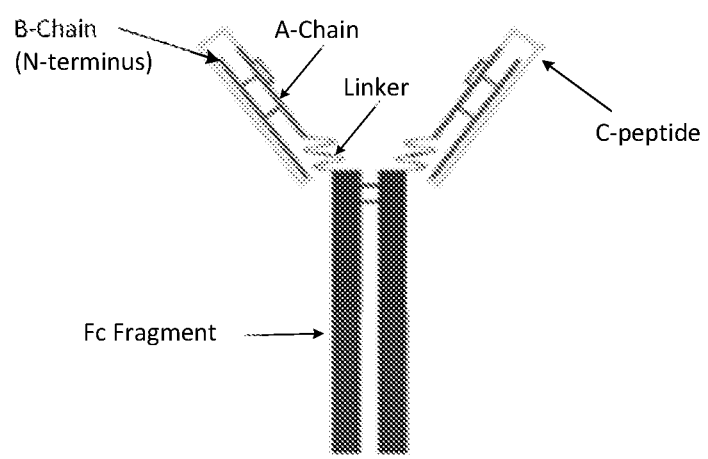
FIG. 1A shows a schematic representation of an exemplary insulin-Fc fusion protein. Each insulin-Fc fusion protein comprises a proinsulin-like insulin molecule containing an insulin B chain and an insulin A chain that are optionally connected between the B chain-C-terminal region and the A chain-$NH_2$ terminus with a linker peptide, and the A chain-C-terminal region and Fc-chain amino terminus with a linker, and the insulin-Fc fusion protein sequence terminating in the Fc-$CH_3$—C-terminal region.

It is to be appreciated that certain aspects, modes, embodiments, variations and features of the present methods are described below in various levels of detail in order to provide a substantial understanding of the present technology.

In practicing the present methods, many conventional techniques in molecular biology, protein biochemistry, cell biology, immunology, microbiology and recombinant DNA are used. See, e.g., Sambrook and Russell eds. (2001) *Molecular Cloning: A Laboratory Manual*, 3rd edition; the series Ausubel et al. eds. (2007) *Current Protocols in Molecular Biology*; the series *Methods in Enzymology* (Academic Press, Inc., N.Y.); MacPherson et al. (1991) *PCR 1: A Practical Approach* (IRL Press at Oxford University Press); MacPherson et al. (1995) *PCR 2: A Practical Approach*; Harlow and Lane eds. (1999) *Antibodies, A Laboratory Manual*; Freshney (2005) *Culture of Animal Cells: A Manual of Basic Technique,* 5th edition; Gait ed. (1984) *Oligonucleotide Synthesis*; U.S. Pat. No. 4,683,195; Hames and Higgins eds. (1984) *Nucleic Acid Hybridization;* Anderson (1999) *Nucleic Acid Hybridization*; Hames and Higgins eds. (1984) *Transcription and Translation; Immobilized Cells and Enzymes* (IRL Press (1986)); Perbal (1984) *A Practical Guide to Molecular Cloning*; Miller and Cabs eds. (1987) *Gene Transfer Vectors for Mammalian Cells* (Cold Spring Harbor Laboratory); Makrides ed. (2003) *Gene Transfer and Expression in Mammalian Cells*; Mayer and Walker eds. (1987) *Immunochemical Methods in Cell and Molecular Biology* (Academic Press, London); and Herzenberg et al. eds (1996) *Weir's Handbook of Experimental Immunology.*

The present disclosure relates to compositions of insulin-Fc fusion proteins (e.g., proinsulin-Fc fusion proteins) and their use to treat or prevent autoimmune disease, e.g., autoimmune diabetes, e.g., type 1 diabetes. As described herein, the insulin-Fc fusion proteins of the present technology selectively bind to autoantigen-specific B cells (e.g., insulin-specific B cells), thus avoiding drawbacks associated with the non-specific global elimination of all B cells (e.g., immunocompromisation). Additionally, the insulin-Fc fusion proteins of the present technology avoid non-specifically deleting all cells that express the insulin hormone receptor as they lack binding affinity for insulin that is bound to an insulin hormone receptor. Without wishing to be bound by theory, it is believed that in some embodiments, the fusion proteins described herein bind to autoantigen-specific BCRs (e.g., insulin-specific BCRs).

The insulin-Fc fusion proteins of the present technology do not interfere with the binding of biotin labelled-insulin to the IM-9 insulin-hormone receptor, and therefore bind the insulin receptor present on IM-9 cells very weakly or not at all, which minimizes their chances of lowering blood sugar in vivo. This is an advantageous property for treating patients with an autoimmune disease (e.g., pre-diabetic patients, patients with insulin autoantibodies, or recent-onset type 1 diabetic patients), who may have normal or slightly elevated blood sugar levels and would be susceptible to the risk of potential hypoglycemia (e.g. low blood sugar) induced by therapy with insulin-Fc fusion proteins that are able to bind the insulin receptor with $IC_{50}$ values <3,000 nM or proteins with even higher binding affinities with $IC_{50}$ values <1,000 nM in the in vitro binding assay described herein). Accordingly, the insulin-Fc fusion proteins of the present technology are useful for treating or preventing autoimmune Type 1 diabetes in subjects without lowering their in vivo blood glucose levels.

Definitions

Unless defined otherwise, all technical and scientific terms used herein generally have the same meaning as commonly understood by one of ordinary skill in the art to which this technology belongs. As used in this specification and the appended claims, the singular forms "a", "an" and "the" include plural referents unless the content clearly dictates otherwise. For example, reference to "a cell" includes a combination of two or more cells, and the like. Generally, the nomenclature used herein and the laboratory procedures in cell culture, molecular genetics, organic chemistry, analytical chemistry and nucleic acid chemistry and hybridization described below are those well-known and commonly employed in the art.

The terms "insulin$^+$", "Ins$^+$", "insulin-specific" and "anti-insulin" are used interchangeably herein.

As used herein, $EC_{50}$ refers to the concentration of an insulin-Fc fusion protein at which half-maximal response for in vitro insulin-specific B cell deletion is observed (e.g., concentration at which the insulin$^+$ B cell receptors are reduced by half).

As used herein, $IC_{50}$ refers to the concentration of an insulin-Fc fusion protein at which a given biological function or biochemical process (e.g., binding) is inhibited by half. In some embodiments, $IC_{50}$ refers to the concentration of an insulin-Fc fusion protein where the binding of insulin to the human insulin receptor is reduced by half. In some embodiments, the $IC_{50}$ refers to the concentration of an insulin-Fc fusion protein where the binding of insulin to insulin-specific B cell is reduced by half. In some embodiments, the $IC_{50}$ is the concentration of an insulin-Fc fusion protein where the T cell activation induced by a reference standard is reduced by half.

As used herein, the term "about" in reference to a number is generally taken to include numbers that fall within a range of 1%, 5%, 10%, or 20% in either direction (greater than or less than) of the number unless otherwise stated or otherwise evident from the context (except where such number would be less than 0% or exceed 100% of a possible value).

As used herein, the "administration" of an agent or drug to a subject includes any route of introducing or delivering to a subject a compound to perform its intended function. Administration can be carried out by any suitable route, including but not limited to, orally, intranasally, parenterally (intravenously, intramuscularly, intraperitoneally, or subcutaneously), rectally, intrathecally, transdermally, or topically. Administration includes self-administration and the administration by another.

As used herein, the term "analog" refers to a compound or conjugate (e.g., a compound, conjugate as described herein, e.g., insulin) having a chemical structure similar to that of another compound or conjugate, but differing from it in at least one aspect.

As used herein, the term "autoantibody" refers to an antibody that targets and/or reacts with one or more of an individual's own proteins, cells, tissues, or organs. The term "autoantigen" as used herein refers to an antigen comprised of normal tissue, cells, protein, peptides, or DNA that is the target of an immune response (e.g., a humoral or cell-mediated immune response). An autoantigen may be targeted by or react with an autoantibody in the case of an autoimmune disease.

As used herein, "autoimmune diabetes" refers to diabetes that is characterized by the destruction of the insulin-producing β-cells of the pancreas.

As used herein, the term "cell surface receptor" refers to a molecule such as a protein, generally found on the external surface of a cell membrane and which interacts with soluble molecules, e.g., that circulate in the blood supply. Cell surface receptors may also be secreted in a soluble form into the extracellular space or may be shed from the external surface of a cell. In some embodiments, a cell surface receptor may include an antigen, or an antigen receptor. In other embodiments, B lymphocytes, also termed B cells, have cell surface receptors that are referred to as "B cell receptors", or "BCR", or in some cases "IgM" receptor.

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease, a positive control (a compound or composition known to exhibit the desired therapeutic effect) and a negative control (a subject or a sample that does not receive the therapy or receives a placebo) are typically employed.

As used herein, the term "effective amount" refers to a quantity sufficient to achieve a desired therapeutic and/or prophylactic effect, e.g., an amount which results in the prevention of, or a decrease in a disease or condition described herein or one or more signs or symptoms associated with a disease or condition described herein. In the context of therapeutic or prophylactic applications, the amount of a composition administered to the subject will vary depending on the composition, the degree, type, and severity of the disease and on the characteristics of the individual, such as general health, age, sex, body weight and tolerance to drugs. The skilled artisan will be able to determine appropriate dosages depending on these and other factors. The compositions can also be administered in combination with one or more additional therapeutic compounds. In the methods described herein, the pharmaceutical compositions may be administered to a subject having one or more signs or symptoms of an autoimmune disease (e.g., autoimmune diabetes, e.g., Type 1 diabetes). As used herein, a "therapeutically effective amount" of a composition refers to composition levels in which the physiological effects of a disease or condition described herein are ameliorated or eliminated. A therapeutically effective amount can be given in one or more administrations. As used herein, a "prophylactically effective amount" of a composition refers to composition levels that prevent or delay the onset of at least one symptom of a disease or condition described herein. A prophylactically effective amount can be given in one or more administrations.

As used herein, the term "endogenous C-peptide" level refers to the level of C-peptide in the subject prior to a treatment, e.g., an insulin-Fc fusion protein treatment described herein.

As used herein, the term "fusion protein", e.g., "insulin-Fc fusion" protein refers to a protein comprising more than one domain, e.g., typically from different sources (e.g., different proteins, polypeptides, cells, etc.), that are covalently linked through peptide bonds. In some embodiments, a fusion protein is produced recombinantly. In some embodiments, the domains of a fusion protein are covalently linked by connecting the gene sequences that encode each domain into a single nucleic acid molecule. In some embodiments, an insulin-Fc fusion protein is a protein, e.g., a single polypeptide, comprising an insulin polypeptide (e.g., proinsulin polypeptide) and an Fc fragment polypeptide, where the insulin and Fc fragment polypeptides are joined by peptide bonds to form a single polypeptide.

As used herein, the term "insulin" encompasses mature insulin, preproinsulin, and proinsulin, as well as naturally occurring insulin or analogs thereof (e.g., proinsulin analogs). In some embodiments, an insulin polypeptide, e.g., proinsulin polypeptide, can be a full-length insulin (e.g., full-length proinsulin) polypeptide or a fragment thereof. In some embodiments, an insulin polypeptide (e.g., proinsulin polypeptide) comprises one or more fragments or domains from a naturally occurring insulin (e.g., proinsulin) and/or one or more fragments or domains from a non-naturally occurring insulin (e.g., proinsulin).

As used herein, the terms "individual", "patient", or "subject" can be an individual organism, a vertebrate, a mammal, or a human. In some embodiments, the individual, patient or subject is a human. Exemplary human subjects include a human patient having a disorder, e.g., a disorder described herein, or a normal subject.

The terms "parenteral administration" and "administered parenterally" as used herein refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The term "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable carrier" as used herein means a pharmaceutically acceptable material, composition or vehicle, such as a liquid or solid filler, diluent, excipient, solvent or encapsulating material, involved in carrying or transporting the insulin-Fc fusion proteins of the present technology from one organ, or portion of the body, to another organ, or portion of the body. Each carrier must be "acceptable" in the sense of being compatible with the other ingredients of the formulation and not injurious to the patient.

As used herein, "prevention" or "preventing" of a disorder or condition refers to a compound that, in a statistical sample, reduces the occurrence of the disorder or condition in the treated sample relative to an untreated control sample, or delays the onset of one or more symptoms of the disorder or condition relative to the untreated control sample. As used herein, preventing an autoimmune disease (e.g., autoimmune diabetes, e.g., Type 1 diabetes), includes preventing or delaying the initiation of symptoms of an autoimmune disease (e.g., autoimmune diabetes, e.g., Type 1 diabetes). As used herein, prevention of an autoimmune disease (e.g., autoimmune diabetes, e.g., Type 1 diabetes) also includes preventing a recurrence of one or more signs or symptoms of an autoimmune disease (e.g., autoimmune diabetes, e.g., Type 1 diabetes).

As used herein, the term "sample" means biological sample material derived from living cells of a subject. Biological samples may include tissues, cells, protein or membrane extracts of cells, and biological fluids (e.g., ascites fluid or cerebrospinal fluid (CSF)) isolated from a subject, as well as tissues, cells and fluids (blood, plasma, saliva, urine, serum, etc.) present within a subject.

As used herein, the term "separate" therapeutic use refers to an administration of at least two active ingredients at the same time or at substantially the same time by different routes.

As used herein, the terms "sequence identity" or "identical" in the context of an amino acid or nucleotide sequence mean that the same nucleotides or amino acid residues are found within a particular query sequence and a reference sequence when a specified, contiguous segment of the nucleotide sequence or amino acid sequence of the query sequence is aligned and compared to the nucleotide sequence or amino acid sequence of the reference sequence. Methods for sequence alignment and for determining identity between sequences are known in the art. See, e.g., Ausubel et al., eds. (1995) *Current Protocols in Molecular Biology*, Chapter 19 (Greene Publishing and Wiley-Interscience, New York); and the ALIGN program (Dayhoff (1978) in *Atlas of Polypeptide Sequence and Structure* 5: Suppl. 3 (National Biomedical Research Foundation, Washington, D.C.)). With respect to optimal alignment of two nucleotide sequences, the contiguous segment of the query nucleotide sequence may have additional nucleotides or deleted nucleotides with respect to the reference nucleotide sequence. Likewise, for purposes of optimal alignment of two amino acid sequences, the contiguous segment of the query amino acid sequence may have additional amino acid residues or deleted amino acid residues with respect to the reference amino acid sequence. In some embodiments, the contiguous segment used for comparison to the reference nucleotide sequence or reference amino acid sequence will comprise at least 6, 10, 15, or 20 contiguous nucleotides, or amino acid residues, and may be 30, 40, 50, 100, or more nucleotides or amino acid residues. Corrections for increased sequence identity associated with inclusion of gaps in the query nucleotide sequence or amino acid sequence can be made by assigning gap penalties. Methods of sequence alignment are known in the art.

In certain embodiments, the determination of percent identity between two sequences is accomplished using a mathematical algorithm. For example, the percent identity of an amino acid sequence is determined using the Smith-Waterman homology search algorithm using an affine 6 gap search with a gap open penalty of 12 and a gap extension penalty of 2, BLOSUM matrix 62. The Smith-Waterman homology search algorithm is described in Smith and Waterman (1981) *Adv. Appl. Math* 2:482-489, herein incorporated by reference. In some embodiments, the percent identity of a nucleotide sequence is determined using the Smith-Waterman homology search algorithm using a gap open penalty of 25 and a gap extension penalty of 5. Such a determination of sequence identity can be performed using, for example, the DeCypher Hardware Accelerator from TimeLogic.

As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

As used herein, the term "simultaneous" therapeutic use refers to the administration of at least two active ingredients by the same route and at the same time or at substantially the same time.

As used herein, "specifically binds" or "selectively binds" refers to the non-covalent interactions of the type which occur between (i) an immunoglobulin molecule (e.g., anti-insulin immunoglobulin) and an insulin or an insulin-Fc fusion protein of the present technology, (ii) a B cell receptor (e.g., anti-insulin immunoglobulin) and an insulin or insulin-Fc fusion protein of the present technology, or (iii) a B cell expressing a B cell receptor (e.g., anti-insulin immuno- globulin) and an insulin or insulin-Fc fusion protein of the present technology. The strength, or affinity of the binding interactions, e.g., immunological binding interactions or specific binding interactions, can be expressed in terms of the dissociation constant ($K_d$) of the interaction, wherein a smaller $K_d$ represents a higher affinity. Immunological or specific binding properties of selected polypeptides can be quantified using methods known in the art. One such method entails measuring the rates of ligand/ligand-receptor complex (e.g., antigen/antigen receptor complex; insulin antibody/insulin complex; or insulin antibody/insulin-Fc fusion protein complex) formation and dissociation, wherein those rates depend on the concentrations of the complex partners, the affinity of the interaction, and geometric parameters that equally influence the rate in both directions. Thus, both the "on rate constant" ($k_{on}$) and the "off rate constant" ($k_{off}$) can be determined by calculation of the concentrations and the actual rates of association and dissociation. See, e.g., *Nature* 361:186-87 (1993). The ratio of $k_{off}/k_{on}$ enables the cancellation of all parameters not related to affinity, and is equal to the dissociation constant $K_d$. (See, generally, Davies et al. (1990) *Annual Rev Biochem* 59:439-473). In some embodiments, a fusion protein described herein specifically binds an anti-insulin antibody immunoglobulin, a BCR (e.g., a BCR comprising an anti-insulin immunoglobulin), and/or a B cell, e.g., autoantigen-specific B cell such as an insulin-specific B cell, when the equilibrium binding constant ($K_d$) is less than or equal to 1 μM, e.g., less than or equal to 100 nM, less than or equal to 10 nM, less than or equal to 100 pM, or less than or equal to about 1 pM, e.g., as measured by assays such as radioligand binding assays, ELISAs, surface plasmon resonance, equilibrium binding assays, or similar assays known to those skilled in the art.

The terms "systemic administration," "administered systemically," "peripheral administration" and "administered peripherally" as used herein mean the administration of the insulin-Fc fusion protein other than directly into the central nervous system, such that it enters the patient's system and, thus, is subject to metabolism and other like processes, for example, subcutaneous administration.

"Treating" or "treatment" as used herein covers the treatment of a disease or disorder described herein, in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder. In some embodiments, treatment means that the symptoms associated with the disease are, e.g., alleviated, reduced, cured, or placed in a state of remission.

It is also to be appreciated that the various modes of treatment of a disease or disorder as described herein are intended to mean "substantial," which includes total but also less than total treatment, and wherein some biologically or medically relevant result is achieved. The treatment may be a continuous prolonged treatment for a chronic disease or a single, or few time administrations for the treatment of an acute condition.

Management of Type I Diabetes

There are three main approaches to reducing or eliminating the hardships associated with T1D: 1) better disease management, e.g., improved insulins, smart pumps, and continuous glucose monitors; 2) disease reversal, e.g., pancreas or islet transplants, β-cell regeneration, systemic or T cell specific immunomodulation; and 3) disease prevention, e.g., avoidance of environmental triggers, antigen-specific vaccination, non-antigen specific immunomodulation therapy). As T1D patients develop autoimmunity, their β-cell function declines and so does the potential therapeutic benefit of intervention (Rewers, M and Gottlieb, P. *Diabetes Care* (2009), 32, 1769-1782). Additionally, once the autoimmune process has begun it might become more progressively difficult to alter. For these reasons and the estimated cost benefit relative to late stage intervention, disease prevention at the earliest possible stage of T1D is ideal for the long term.

Effective disease prevention requires an in-depth understanding of the T1D autoimmune process as well as tools that can accurately diagnose or predict the risk of developing T1D well before the onset of overt hyperglycemia. After initiation of islet autoimmunity, most T1D patients have a long preclinical period that offers an opportunity for treatments to halt progression to clinical diabetes. A major hallmark of the onset of islet autoimmunity is the presence of circulating antibodies specific for islet-autoantigens including insulin, isoform 65 of glutamate decarboxylase (anti-GAD65), protein tyrosine phosphatase-like protein (IA2), and the zinc transporter 8 (ZnT8). In fact, at diagnosis greater than 90% of T1D patients present at least one islet-specific antibody, and in the prospective Diabetes Autoimmunity Study in the Young (DAISY) cohort, 89% of children who progressed to diabetes expressed two or more islet-specific autoantibodies. Although $CD4^+$ and $CD8^+$ T cells contribute to the ultimate attack on β-cells, the pathogenic role of B cells (e.g., anti-insulin B cells, insulin-specific B cells, or $insulin^+$ B cells) has emerged in recent years, which may help explain why antibodies and T cells are specific for the same islet-specific autoantigens, as well as the lag in timing between the appearance of islet-specific autoantibodies and complete T cell mediated β-cell destruction. B cells can take up islet antigens, present them to helper T cells, and differentiate into antibody secreting plasma cells which enhance antigen uptake by antigen-presenting cells ultimately leading to the activation of cytotoxic T cells for β-cell destruction.

Global B cell depletion, e.g., by a B cell antigen antibody such as rituximab, has been proposed as a treatment for autoimmune disease, e.g., T1D. See, e.g., Pescovitz et al., *N. England J. Med.* 361.22(2009):2143-52. However, global B cell depletion has been shown to cause immunocompromisation in subjects due to the nonspecific elimination of healthy/non-autoimmune B cells that are normally required by the immune system for normal function (e.g., clearance of pathogens).

Thus, there is a need for treatments and prophylaxes for autoimmune diseases such as T1D that avoid adverse effects caused by the destruction of healthy cells.

Fc Domains

The term "Fc region", "Fc domain", "Fc fragment" as used herein refers to a C-terminal region of an immunoglobulin heavy chain, which is capable of binding to a mammalian Fc(gamma) or Fc(Rn) receptor, e.g., human Fc(gamma) or Fc(Rn) receptor. An Fc receptor (FcR) refers to a receptor that binds to an Fc fragment or the Fc region of an antibody. In certain embodiments, the FcR is a native human FcR sequence. In some embodiments, the FcR binds an IgG antibody a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are described in Ravetch and Kinet, 1991, *Ann. Rev. Immunol.*, 9:457-92; Capel et al., 1994, *Immunomethods*, 4:25-34; and de Haas et al., 1995, *J. Lab. Clin. Med.*, 126:330-41. "FcR" also includes the neonatal receptor, FcRn, which is responsible for the transfer of maternal IgGs to the fetus (Guyer et al., 1976 *J. Immunol.*, 117:587; and Kim et al., 1994, *J. Immunol.*, 24:249) and contributes to the prolonged in vivo elimination half-lives of antibodies and Fc-fusion proteins in vivo.

The Fc fragment, region, or domain may be a native sequence Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat. Kabat et al., Sequences of Proteins of immunological Interest, 5th Ed. Public Health Service, National Institutes of Health, Bethesda, Md., 1991. The Fc region of an immunoglobulin generally comprises two constant domains, CH2 and CH3.

In some embodiments, the Fc fragment comprises or consists of the Fc region (e.g., CH2 domain and CH3 domain) of a mammalian IgG, e.g., human IgG. In certain embodiments, the Fc fragment comprises or consists of the Fc region (e.g., CH2 domain and CH3 domain) of human $IgG_1$. In some embodiments, the Fc fragment comprises or consists of an amino acid sequence having at least 80% (e.g., at least 80%, 85%, 90%, 95%, 97%, 99%, or more) identity to the Fc region (e.g., CH2 domain and CH3 domain) of human $IgG_1$.

In some embodiments, the Fc region of a human $IgG_1$ comprises the following amino acid sequence: DKTHTCPPCPAPELLGGPSVFLFPPKPKDTLMISRTPEVTCVVVDVSHEDPEVKFNWYV DGVEVHNAKTKPREEQYNSTYRVVS VLTVLHQDWLNGKEYKCKVSNKALPAPIEKTIS KAKGQPREPQVYTLPPSRDELTKNQVSLTCLVKGFYPSDIAVEWESNGQPENNYKTTPP VLDSDGSFFLYSKLTVDKSRWQQGNVFSCSVMHEALHNHYTQKSLSLSPG (SEQ ID NO: 22).

In certain embodiments, the Fc region of a human $IgG_1$ comprises an additional amino acid at one or both termini. In some embodiments, this additional amino acid comprises a charged side chain (e.g., a positively charged amino acid, e.g., lysine or arginine). In certain embodiments, the Fc region of a human $IgG_1$ comprises the following amino acid sequence: DKTHTCPPCPAPELLGGPSVFLFPPKPKDTLMISRTPEVTCVVVDVSHEDPEVKFNWYV DGVEVHNAKTKPREEQYNSTYRVVSVLTVLHQDWLNGKEYKCKVSNKALPAPIEKTIS KAKGQPREPQVYTLPPSRDELTKNQVSLTCLVKGFYPSDIAVEWESNGQPENNYKTTPP VLDSDGSFFLYSKLTVDKSRWQQGNVFSCSVMHEALHNHYTQKSLSLSPGK (SEQ ID NO: 23).

Insulin and Insulin Analogs

Insulin is a peptide hormone produced by β-cells in the islets of Langerhans within the pancreas. Insulin functions by regulating the absorption of glucose from the blood. When exposed to a stimulus, such as increased protein and glucose levels, insulin is released from β-cells and binds to the insulin receptor, initiating a signaling cascade that affects many aspects of human metabolism. Disruption of this process is directly related to several diseases, autoimmune diabetes (e.g., Type 1 diabetes), insulinoma, insulin resistance, metabolic syndromes, and polycystic ovary syndrome. The amino acid sequence of insulin is strongly conserved throughout evolution, particularly in vertebrates, and consists of two polypeptide chains, termed the A and B chains, that are linked through disulfide bonds. The sequence of human proinsulin is represented by the amino acid sequence: FVNQHLCGSHLVEALYLVCGERGFFYT-PKTRREAEDLQVGQVELGGGPGAGSLQPLAL EGSLQKRGIVEQCCTSICSLYQLENYCN (SEQ ID NO: 24).

Insulin is initially synthesized as an inactive precursor called preproinsulin. Through a series of highly coordinated, enzyme-regulated steps, preproinsulin is converted into mature insulin. Cleavage of the signal peptide of preproinsulin in the endoplasmic reticulum followed by oxidation and chaperone-assisted folding yields proinsulin, which is transported to the trans-Golgi network. Proinsulin is then subjected to further proteolytic processing steps, resulting in the release of a fragment called the C-peptide and formation of mature insulin, which is stored within zinc ($Zn^{2+}$) and calcium ($Ca^{2+}$)-rich secretory vesicles in β-cells as an inactive hexamer. After exposure to a stimulus, the secretory vesicles fuse with the plasma membrane, releasing the insulin and promoting the dissociation of the hexamers into active insulin monomers. In some embodiments, the insulin of the present disclosure is a monomer. In some embodiments, the insulin is a non-covalent multimer (e.g., a dimer, tetramer, hexamer, or higher order multimer, e.g., a trimer of dimers). In some embodiments, the insulin may be a monomer or a non-covalent multimer (e.g., a dimer, tetramer, hexamer, or higher order multimer, e.g., a trimer of dimers).

In some embodiments, the insulin described herein is a single chain insulin. In some embodiments, the insulin is a preproinsulin or a proinsulin, e.g., a prohormone precursor to mature insulin. All salt forms and non-salt forms of insulin and insulin analogs (e.g. proinsulin and proinsulin analogs) are encompassed by the scope of the present disclosure.

In some embodiments, the insulin of the present disclosure comprises an insulin analog (e.g., proinsulin analog). Several analogs of human insulin are commercially available for therapeutic use. In some embodiments, the insulin analog of the present technology is a monomer. In some embodiments, the insulin analog is a non-covalent multimer (e.g., a dimer, tetramer, hexamer, or higher order multimer, e.g., a trimer of dimers).

The insulin analogs may be closely related to the structure of human insulin, yet contain a modification (e.g. a structural modification) to enhance a certain functional aspect. In some embodiments, the insulin analog may differ from the structure of human insulin by amino acid substitutions only. In some embodiments, the insulin analog may differ from the structure of human insulin by amino acid deletions only. In some embodiments, the insulin analog may differ from the structure of human insulin by amino acid additions only. In some embodiments, the insulin analog comprises a variant or mutant of insulin the sequence of insulin as described by SEQ ID NO: 24). In some embodiments, the insulin analog comprises an amino acid substitution, deletion, or addition relative to insulin (e.g., the sequence of insulin as described by SEQ ID NO: 24). In some embodiments, the insulin analog comprises at least 2, at least 3, at least 4, at least 5, at least 6, at least 7, at least 8, at least 9, at least 10, at least 12, at least 15, at least 20, at least 25, at least 30, at least 40, or at least 50 amino acid substitutions, deletions, or additions relative to insulin (e.g., the sequence of insulin as described by SEQ ID NO: 24).

In some embodiments, the insulin or insulin analog is a three-chain peptide comprising elements of an A chain, a B chain, and a C chain. In some embodiments, the insulin or insulin analog comprises a wild-type insulin B, A, and/or C chain peptide, e.g., from a mammal (e.g., human or mouse).

The sequences of the human insulin A chain and B chain are represented by SEQ ID NO: 19 and SEQ ID NO: 25, respectively: Human insulin A chain: GIVEQCCTSICSLY-QLENYCN (SEQ ID NO: 19); Human insulin B chain: FVNQHLCGSHLVEALYLVCGERGFFYTPKT (SEQ ID NO: 25).

In some embodiments, modifications to the sequence of the insulin or insulin analog (e.g., amino acid substitutions, deletions, or additions or chemical modifications) may be to either the A chain of insulin, the B chain of insulin, or any combination thereof. In some embodiments, when the insulin or insulin analog is a non-covalent multimer comprising more than one A chain, B chain, and/or C chain, modifications to the sequence of insulin (e.g., amino acid substitutions, deletions, or additions or chemical modifications) may be to either the A chain, B chain, or both in the non-covalent multimer.

Insulin-Fc Fusion Proteins of the Present Technology

In one aspect, the present disclosure provides an insulin-Fc fusion protein comprising an insulin polypeptide fused to a Fc domain, wherein the insulin polypeptide comprises a B-chain peptide, a C-chain peptide, and an A-chain peptide, and wherein the amino acid sequence of the C-chain peptide is AAK (SEQ ID NO: 16). Additionally or alternatively, in some embodiments, the insulin-Fc fusion protein binds human insulin receptor at an $IC_{50}>5,000$ nM in a competitive binding assay. In some embodiments, the insulin-Fc fusion proteins described herein have low bioactivity or are substantially metabolically inactive, e.g., they do not substantially lower blood glucose levels in a subject upon administration.

Additionally or alternatively, in some embodiments, the insulin-Fc fusion protein inhibits in vitro binding of insulin$^+$ B cell receptors to insulin at an $IC_{50}<300$ nM, <200 nM, <150 nM, <100 nM, or <75 nM. Additionally or alternatively, in some embodiments, the insulin-Fc fusion protein activates T-cells to secrete IL-2 levels that are reduced compared to that observed in T-cells activated by recombinant human insulin. In some embodiments, the the insulin-Fc fusion protein activates T-cells to secrete IL-2 levels that are less than 3,000 pg/ml, less than 1,000 pg/mL, less than 500 pg/mL, less than 300 pg/mL, or less than 100 pg/ml.

In certain embodiments, the insulin polypeptide is a proinsulin polypeptide or a preproinsulin polypeptide. In some embodiments of the insulin-Fc fusion protein, the amino acid sequence of the A-chain peptide comprises SEQ ID NO: 19. The insulin polypeptide may be fused to the Fc fragment via a peptide linker. Examples of peptide linkers include SEQ ID NO: 20 and SEQ ID NO: 21. Alternatively, no peptide linker may be present between the insulin polypeptide and the Fc domain of the insulin-Fc fusion protein (e.g., the C-terminal region of the insulin polypeptide is covalently linked (e.g., via a peptide bond) to the N-terminal region of the Fc domain or the N-terminal region of the insulin polypeptide is covalently linked (e.g., via a peptide bond) to the C-terminal region of the Fc domain). Additionally or alternatively, in some embodiments of the insulin-Fc fusion protein, the Fc domain comprises a wild-type Fc fragment of human IgG$_1$. In certain embodiments, the amino acid sequence of the Fc domain comprises SEQ ID NO: 22.

Additionally or alternatively, in any of the above embodiments of the insulin-Fc fusion protein, the orientation of the insulin polypeptide from N- to C-termini is: (N-terminus)-B-chain peptide-C-chain peptide-A-chain peptide-(C-terminus). The insulin polypeptide may be located at the N-terminus or C-terminus of the Fc domain.

Additionally or alternatively, in any of the above embodiments of the insulin-Fc fusion protein, the B-chain peptide comprises the amino acid sequence FVNQHLCGSHLVX$_1$ALX$_2$LVCGEX$_3$GFFYTPK (SEQ ID NO: 28), wherein X$_1$ is E or Q, X$_2$ is Y or A, and X$_3$ is R or E. In certain embodiments, X$_2$ is A.

In one aspect, the present disclosure provides an insulin-Fc fusion protein comprising an insulin polypeptide fused to a Fc domain, wherein the insulin polypeptide comprises a B-chain peptide, a C-chain peptide, and an A-chain peptide, wherein the B-chain peptide comprises the amino acid sequence FVNQHLCGSHLVX$_1$ALX$_2$LVCGEX$_3$GFFYTPK (SEQ ID NO: 28), wherein X$_1$ is E or Q, X$_2$ is Y or A, and X$_3$ is R or E; and wherein the amino acid sequence of the C-chain peptide is AAK (SEQ ID NO: 16). In some embodiments, X$_2$ is A.

In certain embodiments of the insulin-Fc fusion protein, the insulin polypeptide is a proinsulin polypeptide or a preproinsulin polypeptide. In some embodiments of the insulin-Fc fusion protein, the amino acid sequence of the A-chain peptide comprises SEQ ID NO: 19. The insulin polypeptide may be fused to the Fc fragment via a peptide linker. Examples of peptide linkers include SEQ ID NO: 20 and SEQ ID NO: 21. Alternatively, no peptide linker may be present between the insulin polypeptide and the Fc domain of the insulin-Fc fusion protein. Additionally or alternatively, in some embodiments of the insulin-Fc fusion protein, the Fc domain comprises a wild-type Fc fragment of human IgG$_1$. In certain embodiments, the amino acid sequence of the Fc domain comprises SEQ ID NO: 22. Additionally or alternatively, in some embodiments, the amino acid sequence of the insulin-Fc fusion protein is SEQ ID NO: 2, SEQ ID NO: 3, SEQ ID NO: 4, SEQ ID NO: 5, SEQ ID NO: 6, SEQ ID NO: 7, or SEQ ID NO: 8.

Figure 1B:
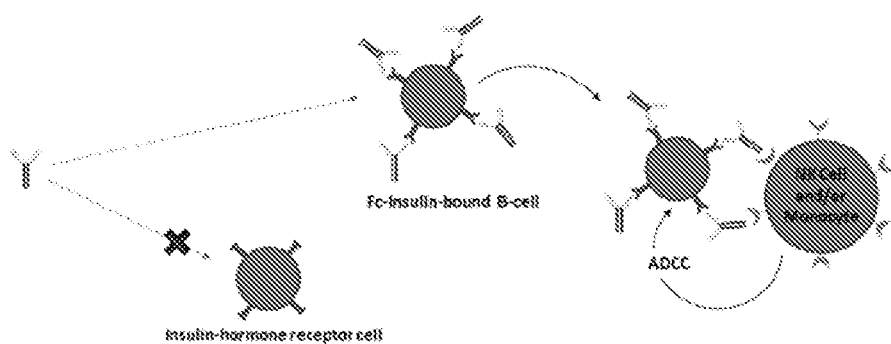
FIG. 1B shows an illustration depicting an insulin-Fc fusion protein that does not interact with the insulin-hormone receptor but is capable of binding insulin-specific B cell receptors and directing their destruction through antibody-dependent cell-mediated cytotoxicity (ADCC).

FIG. 1A shows a schematic representation of an exemplary insulin-Fc fusion protein of the present technology. The insulin-Fc fusion proteins described herein have an advantage of specifically binding to one or more of: (i) soluble anti-insulin antibodies (e.g., anti-insulin antibodies not bound to a cell); (ii) anti-insulin immunoglobulins bound to a B cell receptor (BCR), e.g., on a B cell (e.g., an anti-insulin B cell); and/or (iii) anti-insulin B cells, but do not interact with the insulin-hormone receptor. See FIG. 1B.

In one aspect, the present disclosure provides an insulin-Fc fusion protein comprising an insulin polypeptide fused to an Fc domain. In certain embodiments, the insulin polypeptide of the insulin-Fc fusion protein of the present technology comprises domains in the following orientation from N- to C-termini: (N-terminus)-B-chain peptide-C-chain peptide-A-chain peptide-(C-terminus). Additionally or alternatively, in some embodiments, the insulin-Fc fusion protein comprises domains in the following orientation from N- to C-termini: (N-terminus)-insulin polypeptide-optional linker-Fc domain-(C-terminus) (e.g., (N-terminus)-B-chain peptide-C-chain peptide-A-chain peptide-optional linker-Fc domain-(C-terminus)). In certain embodiments, a linker (e.g., a peptide linker described herein) is located between the insulin polypeptide and the Fc domain. In other embodiments, no linker (e.g., peptide linker) is present between the insulin polypeptide and the Fc domain. Exemplary linkers (e.g., peptide linkers) are described in greater detail in the Linkers section herein.

Exemplary insulin-Fc fusion proteins (e.g., proinsulin-Fc fusion proteins) and their domain sequences are shown in Table A. In some embodiments, the insulin-Fc fusion proteins include modified mutants, e.g., that lead to properties such as anti-insulin B cell removal and/or inhibition of insulin-specific T cell activation.

The insulin-Fc fusion proteins of the present technology comprise a C chain peptide that is about 3-5 amino acids in length and comprises amino acids selected from among alanine and lysine. In some embodiments, the C chain peptide of the insulin-Fc fusion proteins does not comprise amino acids other than alanine and lysine. In certain embodiments, the C chain peptide of the insulin-Fc fusion proteins comprises or consists of the amino acid sequence of: AAK (SEQ ID NO: 16). See Table A.

Additionally or alternatively, in some embodiments, the A chain peptide of the insulin-Fc fusion protein comprises or consists of the amino acid sequence of the A chain peptide of wild type human proinsulin, or an amino acid sequence having at least 80% (e.g., at least 80%, 85%, 90%, 95%, 97%, 99% or more) identity to the amino acid sequence of the A chain peptide of wild type human proinsulin. In some embodiments, the A chain peptide of the insulin-Fc fusion protein comprises or consists of the amino acid sequence of GIVEQCCTSICSLYQLENYCN (SEQ ID NO: 19) or an amino acid sequence having at least 80% (e.g., at least 80%, 85%, 90%, 95%, 97%, 99% or more) identity to SEQ ID NO: 19.

Additionally or alternatively, in some embodiments, the B chain peptide of the insulin-Fc fusion protein comprises or consists of the amino acid sequence of the B chain peptide of wild type human proinsulin or an amino acid sequence having at least 80% (e.g., at least 80%, 85%, 90%, 95%, 97%, 99% or more) identity to the amino acid sequence of the B chain peptide of wild type human proinsulin. In some embodiments, the B-chain peptide of the insulin-Fc fusion protein comprises or consists of the amino acid sequence of a B-chain peptide listed in Table A or an amino acid sequence having at least 80% (e.g., at least 80%, 85%, 90%, 95%, 97%, 99%, or more) identity to a B-chain peptide listed in Table A. In some embodiments, the B chain peptide of the insulin-Fc fusion protein comprises or consists of the amino acid sequence of FVNQHLCGSHLVEALYLVCGERGFFYTPKT (SEQ ID NO: 25) or an amino acid sequence having at least 80% (e.g., at least 80%, 85%, 90%, 95%, 97%, 99% or more) identity to SEQ ID NO: 25.

Additionally or alternatively, in some embodiments, mutations may be introduced to the B chain peptide of the insulin-Fc fusion protein, e.g., to vary the sequence and/or length. Mutations at specific amino acid residues of the B chain of insulin have been shown to abrogate T-cell stimulation in non-obese diabetic (NOD) mice (Nakayama, M. et al. Science (2005) 435:220-223; Nakayama, M. et al *Ann NY Acad Sci* (2006) 1079:122-129). Without being bound by theory, it is believed that certain insulin mutants may disrupt the recognition of the insulin peptide epitope-MHC-II complex by the T-cell receptor, which in turn prevents T cell activation toward the pancreatic islet cells. Exemplary modifications to the sequence of insulin or an insulin analog may include for example, an amino acid substitution at residue 16 (e.g., a Y16A substitution) of SEQ ID NO: 25. Thus, in some embodiments, an insulin-Fc fusion protein comprising at least 1 amino acid substitution, deletion, or addition (e.g., relative to SEQ ID NO. 25) on the B chain of insulin or an insulin analog may result in reduced affinity of T cells for an MHC-II complex bearing the insulin fragment or insulin analog fragment, and/or reduced T cell activation in vivo. Accordingly, in certain embodiments, the B-chain peptide of the insulin-Fc fusion protein comprises a mutated B-chain having a mutation at amino acid residue 16 (e.g., a Y16A substitution). In certain embodiments, the B-chain peptide of the insulin-Fc fusion protein has the sequence of any one of SEQ ID NOs: 11-15.

Provided herein are insulin-Fc fusion proteins comprising an insulin polypeptide operably linked to an Fc domain. In certain embodiments, the insulin-fusion protein comprises an Fc domain described herein. In some embodiments of the insulin-Fc fusion protein, the Fc domain comprises or consists of the amino acid sequence of SEQ ID NO: 22; or an amino acid sequence having at least 80% (e.g., at least 80%, 85%, 90%, 95%, 97%, 99%, or more) identity to SEQ ID NO: 22. In other embodiments of the insulin-Fc fusion protein, the Fc domain comprises or consists of the amino acid sequence of SEQ ID NO: 23; or an amino acid sequence having at least 80% (e.g., at least 80%, 85%, 90%, 95%, 97%, 99%, or more) identity to SEQ ID NO: 23.

The full length sequences of the insulin-Fc fusion proteins of the present technology are provided below:

SEQ ID NO: 2
FVNQHLCGSHLVEALYLVCGERGFFYTPKAAKGIVEQCCTSICSLYQLENY
CNGGGGAGGGGDKTHTCPPCPAPELLGGPSVFLFPPKPKDTLMISRTPEVT
CVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSRDELTKNQ
VSLTCLVKGFYPSDIAVEWESNGQPENNYKTTPPVLDSDGSFFLYSKLTVD
KSRWQQGNVFSCSVMHEALHNHYTQKSLSLSPG

SEQ ID NO: 3
FVNQHLCGSHLVEALALVCGERGFFYTPKAAKGIVEQCCTSICSLYQLENY
CNGGGGAGGGGDKTHTCPPCPAPELLGGPSVFLFPPKPKDTLMISRTPEVT
CVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSRDELTKNQ
VSLTCLVKGFYPSDIAVEWESNGQPENNYKTTPPVLDSDGSFFLYSKLTVD
KSRWQQGNVFSCSVMHEALHNHYTQKSLSLSPG

SEQ ID NO: 4
FVNQHLCGSHLVQALYLVCGERGFFYTPKAAKGIVEQCCTSICSLYQLENY
CNGGGGAGGGGDKTHTCPPCPAPELLGGPSVFLFPPKPKDTLMISRTPEVT
CVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSRDELTKNQ
VSLTCLVKGFYPSDIAVEWESNGQPENNYKTTPPVLDSDGSFFLYSKLTVD
KSRWQQGNVFSCSVMHEALHNHYTQKSLSLSPG

SEQ ID NO: 5
FVNQHLCGSHLVEALYLVCGEEGFFYTPKAAKGIVEQCCTSICSLYQLENY
CNGGGGAGGGGDKTHTCPPCPAPELLGGPSVFLFPPKPKDTLMISRTPEVT
CVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSRDELTKNQ
VSLTCLVKGFYPSDIAVEWESNGQPENNYKTTPPVLDSDGSFFLYSKLTVD
KSRWQQGNVFSCSVMHEALHNHYTQKSLSLSPG

SEQ ID NO: 6
FVNQHLCGSHLVEALALVCGEEGFFYTPKAAKGIVEQCCTSICSLYQLENY
CNGGGGAGGGGDKTHTCPPCPAPELLGGPSVFLFPPKPKDTLMISRTPEVT
CVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSRDELTKNQ
VSLTCLVKGFYPSDIAVEWESNGQPENNYKTTPPVLDSDGSFFLYSKLTVD
KSRWQQGNVFSCSVMHEALHNHYTQKSLSLSPG

SEQ ID NO: 7
FVNQHLCGSHLVEALALVCGERGFFYTPKAAKGIVEQCCTSICSLYQLENY
CNDKTHTCPPCPAPELLGGPSVFLFPPKPKDTLMISRTPEVTCVVVDVSHE
DPEVKFNWYVDGVEVHNAKTKPREEQYNSTYRVVSVLTVLHQDWLNGKEYK
CKVSNKALPAPIEKTISKAKGQPREPQVYTLPPSRDELTKNQVSLTCLVKG
FYPSDIAVEWESNGQPENNYKTTPPVLDSDGSFFLYSKLTVDKSRWQQGNV
FSCSVMHEALHNHYTQKSLSLSPG

SEQ ID NO: 8
FVNQHLCGSHLVEALALVCGERGFFYTPKAAKGIVEQCCTSICSLYQLENY
CNGGGGSGGGGDKTHTCPPCPAPELLGGPSVFLFPPKPKDTLMISRTPEVT
CVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSRDELTKNQ
VSLTCLVKGFYPSDIAVEWESNGQPENNYKTTPPVLDSDGSFFLYSKLTVD
KSRWQQGNVFSCSVMHEALHNHYTQKSLSLSPG

SEQ ID NO: 9
FVNQHLCGSHLVEALALVCGERGFFYTPKAAAKGIVEQCCTSICSLYQLEN
YCNGGGGAGGGGDKTHTCPPCPAPELLGGPSVFLFPPKPKDTLMISRTPEV
TCVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSRDELTKN
QVSLTCLVKGFYPSDIAVEWESNGQPENNYKTTPPVLDSDGSFFLYSKLTV
DKSRWQQGNVFSCSVMHEALHNHYTQKSLSLSPG

SEQ ID NO: 10
FVNQHLCGSHLVEALALVCGERGFFYTPKAAAKGIVEQCCTSICSLYQLE
NYCNGGGGAGGGGDKTHTCPPCPAPELLGGPSVFLFPPKPKDTLMISRTPE
VTCVVVDVSHEDPEVKFNWYVDGVEVHNAKTKPREEQYNSTYRVVSVLTVL
HQDWLNGKEYKCKVSNKALPAPIEKTISKAKGQPREPQVYTLPPSRDELTK
NQVSLTCLVKGFYPSDIAVEWESNGQPENNYKTTPPVLDSDGSFFLYSKLT
VDKSRWQQGNVFSCSVMHEALHNHYTQKSLSLSPG

TABLE A

| Sequence | B Chain | C Peptide | A Chain | Linker | Fc Domain |
|---|---|---|---|---|---|
| SEQ ID NO: 2 | SEQ ID NO: 11 FVNQHLCGSHLVEALYLVCGERGFFYTPK | SEQ ID NO: 16 AAK | SEQ ID NO: 19 GIVEQCCTSICSLYQLENYCN | SEQ ID NO: 20 GGGGAGGGG | SEQ ID NO: 22 DKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG |
| SEQ ID NO: 3 | SEQ ID NO: 12 FVNQHLCGSHLVEALALVCGERGFFYTPK | SEQ ID NO: 16 AAK | SEQ ID NO: 19 GIVEQCCTSICSLYQLENYCN | SEQ ID NO: 20 GGGGAGGGG | SEQ ID NO: 22 DKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG |
| SEQ ID NO: 4 | SEQ ID NO: 13 FVNQHLCGSHLVQALYLVCGERGFFYTPK | SEQ ID NO: 19 AAK | SEQ ID NO: 16 GIVEQCCTSICSLYQLENYCN | SEQ ID NO: 20 GGGGAGGGG | SEQ ID NO: 22 DKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG |
| SEQ ID NO: 5 | SEQ ID NO: 14 FVNQHLCGSHLVEALYLVCGEEGFFYTPK | SEQ ID NO: 16 AAK | SEQ ID NO: 19 GIVEQCCTSICSLYQLENYCN | SEQ ID NO: 20 GGGGAGGGG | SEQ ID NO: 22 DKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG |
| SEQ ID NO: 6 | SEQ ID NO: 15 FVNQHLCGSHLVEALALVCGEEGFFYTPK | SEQ ID NO: 16 AAK | SEQ ID NO: 19 GIVEQCCTSICSLYQLENYCN | SEQ ID NO: 20 GGGGAGGGG | SEQ ID NO: 22 DKTHTCPPCPAPELLGGPSVFLFPPKPKDTLMISRTPEVTCVVVDVSHEDPEVKFNWYVDGVEVHNAKTKPREEQ |

TABLE A-continued

| Sequence | B Chain | C Peptide | A Chain | Linker | Fc Domain |
|---|---|---|---|---|---|
| | | | | | YNSTYRVVSVLTVLH QDWLNGKEYKCKVS NKALPAPIEKTISKAK GQPREPQVYTLPPSR DELTKNQVSLTCLVK GFYPSDIAVEWESNG QPENNYKTTPPVLDS DGSFFLYSKLTVDKS RWQQGNVFSCSVMH EALHNHYTQKSLSLS PG |
| SEQ ID NO: 7 | SEQ ID NO: 12 FVNQHLCG SHLVEALA LVCGERGF FYTPK | SEQ ID NO: 16 AAK | SEQ ID NO: 19 GIVEQCCT SICSLYQL ENYCN | | SEQ ID NO: 22 DKTHTCPPCPAPELL GGPSVFLFPPKPKDTL MISRTPEVTCVVVDV SHEDPEVKFNWYVD GVEVHNAKTKPREEQ YNSTYRVVSVLTVLH QDWLNGKEYKCKVS NKALPAPIEKTISKAK GQPREPQVYTLPPSR DELTKNQVSLTCLVK GFYPSDIAVEWESNG QPENNYKTTPPVLDS DGSFFLYSKLTVDKS RWQQGNVFSCSVMH EALHNHYTQKSLSLS PG |
| SEQ ID NO: 8 | SEQ ID NO: 12 FVNQHLCG SHLVEALA LVCGERGF FYTPK | SEQ ID NO: 19 AAK | SEQ ID NO: 16 GIVEQCCT SICSLYQL ENYCN | SEQ ID NO: 21 GGGGSG GGG | SEQ ID NO: 22 DKTHTCPPCPAPELL GGPSVFLFPPKPKDTL MISRTPEVTCVVVDV SHEDPEVKFNWYVD GVEVHNAKTKPREEQ YNSTYRVVSVLTVLH QDWLNGKEYKCKVS NKALPAPIEKTISKAK GQPREPQVYTLPPSR DELTKNQVSLTCLVK GFYPSDIAVEWESNG QPENNYKTTPPVLDS DGSFFLYSKLTVDKS RWQQGNVFSCSVMH EALHNHYTQKSLSLS PG |
| SEQ ID NO: 9 | SEQ ID NO: 12 FVNQHLCG SHLVEALA LVCGERGF FYTPK | SEQ ID NO: 17 AAAK | SEQ ID NO: 19 GIVEQCCT SICSLYQL ENYCN | SEQ ID NO: 20 GGGGAG GGG | SEQ ID NO: 22 DKTHTCPPCPAPELL GGPSVFLFPPKPKDTL MISRTPEVTCVVVDV SHEDPEVKFNWYVD GVEVHNAKTKPREEQ YNSTYRVVSVLTVLH QDWLNGKEYKCKVS NKALPAPIEKTISKAK GQPREPQVYTLPPSR DELTKNQVSLTCLVK GFYPSDIAVEWESNG QPENNYKTTPPVLDS DGSFFLYSKLTVDKS RWQQGNVFSCSVMH EALHNHYTQKSLSLS PG |
| SEQ ID NO: 10 | SEQ ID NO: 12 FVNQHLCG SHLVEALA LVCGERGF FYTPK | SEQ ID NO: 18 AAAAK | SEQ ID NO: 19 GIVEQCCT SICSLYQL ENYCN | SEQ ID NO: 20 GGGGAG GGG | SEQ ID NO: 22 DKTHTCPPCPAPELL GGPSVFLFPPKPKDTL MISRTPEVTCVVVDV SHEDPEVKFNWYVD GVEVHNAKTKPREEQ YNSTYRVVSVLTVLH QDWLNGKEYKCKVS NKALPAPIEKTISKAK GQPREPQVYTLPPSR DELTKNQVSLTCLVK GFYPSDIAVEWESNG |

TABLE A-continued

| Sequence | B Chain | C Peptide | A Chain | Linker | Fc Domain |
|---|---|---|---|---|---|
| | | | | | QPENNYKTTPPVLDS DGSFFLYSKLTVDKS RWQQGNVFSCSVMH EALHNHYTQKSLSLS PG |

Table A does not include a leader sequence. In some embodiments, an insulin-Fc fusion protein described herein does not include a leader sequence at the N-terminus. In other embodiments, an insulin-Fc fusion protein described herein includes a leader sequence, e.g., at the N-terminus. An exemplary leader sequence includes the amino acid sequence MEWSWVFLFFLSVTTGVHS (SEQ ID NO: 26). In some embodiments, an insulin-Fc fusion protein described herein is encoded by a nucleic acid molecule comprising a leader sequence, e.g., for expression (e.g., recombinant expression) in cells (e.g., eukaryotic, e.g., mammalian cells). In certain embodiments, the leader sequence is cleaved off, e.g., in the cell culture, during expression. An exemplary nucleic acid sequence encoding a leader sequence includes the nucleic acid sequence ATG-GAATGGAGCTGGGTCTTTCTCTTCTTCCTGTCAG-TAACGACTGGTGTCCACTCC (SEQ ID NO: 27). In other embodiments, a fusion protein described herein is encoded by a nucleic acid molecule not comprising a leader sequence.

Also disclosed herein are nucleic acid sequences (e.g., mRNA, cDNA, DNA) encoding the insulin-Fc fusion proteins of SEQ ID NOs: 2-10.

In some embodiments, the nucleic acid sequence is:

(SEQ ID NO: 1)
ATGGAATGGAGCTGGGTCTTTCTCTTCTTCCTGTCAGTAACGACTGGTGT

CCACTCCTTCGTGAAGCAGCACCTGTGCGGCCCTCACCTGGTGGAAGCTC

TGTATCTCGTGTGCGGCGAGCGGGGCTTCTTCTACACCCCCAAGTCTCGG

AGAGAGGTGGAAGATCCCCAGGTGGAACAGCTGGAACTGGGCGGCTCTCC

TGGCGATCTGCAGACACTGGCCCTGGAAGTGGCCCGGCAGAAACGGGGCA

TCGTGGACCAGTGCTGCACCTCCATCTGCTCCCTGTACCAGCTGGAAAAC

TACTGCAATGGTGGAGGCGGTGGAGTGCCCAGAGATTGTGGATGTAAGCC

TTGCATATGTACAGTCCCAGAAGTATCATCTGTCTTCATCTTCCCCCCAA

AGCCCAAGGATGTGCTCACCATTACTCTGACTCCTAAGGTCACGTGTGTT

GTGGTAGACATCAGCAAGGATGATCCCGAGGTCCAGTTCAGCTGGTTTGT

AGATGATGTGGAGGTGCACACAGCTCAGACGCAACCCCGGGAGGAGCAGT

TCAACAGCACTTTCCGCTCAGTCAGTGAACTTCCCATCATGCACCAGGAC

TGGCTCAATGGCAAGGAGTTCAAATGCAGGGTCAACAGTGCAGCTTTCCC

TGCCCCCATCGAGAAAACCATCTCCAAAACCAAAGGCAGACCGAAGGCTC

CACAGGTGTACACCATTCCACCTCCCAAGGAGCAGATGGCCAAGGATAAA

GTCAGTCTGACCTGCATGATAACAGACTTCTTCCCTGAAGACATTACTGT

GGAGTGGCAGTGGAATGGGCAGCCAGCGGAGAACTACAAGAACACTCAGC

CCATCATGGACACAGATGGCTCTTACTTCGTCTACAGCAAGCTCAATGTG

CAGAAGAGCAACTGGGAGGCAGGAAATACTTTCACCTGCTCTGTGTTACA

TGAGGGCCTGCACAACCACCATACTGAGAAGAGCCTCTCCCACTCTCCTG

GTTAG.

In some embodiments, the nucleic acid sequence is:

(SEQ ID NO: 29)
ATGGAATGGAGCTGGGTCTTTCTCTTCTTCCTGTCAGTAACGACTGGTGT

CCACTCCTTCGTGAACCAGCACCTGTGCGGCTCCCACCTGGTGGAAGCTC

TGGCTCTCGTGTGCGGCGAGCGGGGCTTCTTCTACACCCCCAAGGCCGCT

AAAGGCATCGTGGAACAGTGCTGCACCTCCATCTGCTCCCTGTACCAGCT

GGAAAACTACTGCAATGGCGGAGGTGGTGCAGGAGGCGGTGGAGACAAAA

CTCACACATGCCCACCGTGCCCAGCACCTGAACTCCTGGGGGGACCGTCA

GTCTTCCTCTTCCCCCCAAAACCCAAGGACACCCTCATGATCTCCCGGAC

CCCTGAGGTCACATGCGTGGTGGTGGACGTGAGCCACGAAGACCCTGAGG

TCAAGTTCAACTGGTACGTGGACGGCGTGGAGGTGCATAATGCCAAGACA

AAGCCGCGGGAGGAGCAGTACAACAGCACGTACCGTGTGGTCAGCGTCCT

CACCGTCCTGCACCAGGACTGGCTGAATGGCAAGGAGTACAAGTGCAAGG

TCTCCAACAAAGCCCTCCCAGCCCCCATCGAGAAAACCATCTCCAAAGCC

AAAGGGCAGCCCCGAGAACCACAGGTGTACACCCTGCCCCCATCCCGGGA

TGAGCTGACCAAGAACCAGGTCAGCCTGACCTGCCTGGTCAAAGGCTTCT

ATCCCAGCGACATCGCCGTGGAGTGGGAGAGCAATGGGCAGCCGGAGAAC

AACTACAAGACCACGCCTCCCGTGCTGGACTCCGACGGCTCCTTCTTCCT

CTACAGCAAGCTCACCGTGGACAAGAGCAGGTGGCAGCAGGGGAACGTCT

TCTCATGCTCCGTGATGCATGAGGCTCTGCACAACCACTACACGCAGAAG

AGCCTCTCCCTGTCTCCGGGTTAG.

In some embodiments, the nucleic acid sequence is:

(SEQ ID NO: 30)
ATGGAATGGAGCTGGGTCTTTCTCTTCTTCCTGTCAGTAACGACTGGTGT

CCACTCCTTCGTGAACCAGCACCTGTGCGGCTCCCACCTGGTGCAAGCTC

TGTATCTCGTGTGCGGCGAGCGGGGCTTCTTCTACACCCCCAAGGCCGCT

AAAGGCATCGTGGAACAGTGCTGCACCTCCATCTGCTCCCTGTACCAGCT

GGAAAACTACTGCAATGGCGGAGGTGGTGCAGGAGGCGGTGGAGACAAAA

CTCACACATGCCCACCGTGCCCAGCACCTGAACTCCTGGGGGGACCGTCA

GTCTTCCTCTTCCCCCCAAAACCCAAGGACACCCTCATGATCTCCCGGAC

CCCTGAGGTCACATGCGTGGTGGTGGACGTGAGCCACGAAGACCCTGAGG

```
TCAAGTTCAACTGGTACGTGGACGGCGTGGAGGTGCATAATGCCAAGACA
AAGCCGCGGGAGGAGCAGTACAACAGCACGTACCGTGTGGTCAGCGTCCT
CACCGTCCTGCACCAGGACTGGCTGAATGGCAAGGAGTACAAGTGCAAGG
TCTCCAACAAAGCCCTCCCAGCCCCATCGAGAAAACCATCTCCAAAGCC
AAAGGGCAGCCCCGAGAACCACAGGTGTACACCCTGCCCCCATCCCGGGA
TGAGCTGACCAAGAACCAGGTCAGCCTGACCTGCCTGGTCAAAGGCTTCT
ATCCCAGCGACATCGCCGTGGAGTGGGAGAGCAATGGGCAGCCGGAGAAC
AACTACAAGACCACGCCTCCCGTGCTGGACTCCGACGGCTCCTTCTTCCT
CTACAGCAAGCTCACCGTGGACAAGAGCAGGTGGCAGCAGGGGAACGTCT
TCTCATGCTCCGTGATGCATGAGGCTCTGCACAACCACTACACGCAGAAG
AGCCTCTCCCTGTCTCCGGGTTAG.
```

In some embodiments, the nucleic acid sequence is:

```
                                            (SEQ ID NO: 31)
ATGGAATGGAGCTGGGTCTTTCTCTTCTTCCTGTCAGTAACGACTGGTGT
CCACTCCTTCGTGAACCAGCACCTGTGCGGCTCCCACCTGGTGGAAGCTC
TGTATCTCGTGTGCGGCGAGGAGGGCTTCTTCTACACCCCCAAGGCCGCT
AAAGGCATCGTGGAACAGTGCTGCACCTCCATCTGCTCCCTGTACCAGCT
GGAAAACTACTGCAATGGCGGAGGTGGTGCAGGAGGCGGTGGAGACAAAA
CTCACACATGCCCACCGTGCCCAGCACCTGAACTCCTGGGGGGACCGTCA
GTCTTCCTCTTCCCCCCAAAACCCAAGGACACCCTCATGATCTCCCGGAC
CCCTGAGGTCACATGCGTGGTGGTGGACGTGAGCCACGAAGACCCTGAGG
TCAAGTTCAACTGGTACGTGGACGGCGTGGAGGTGCATAATGCCAAGACA
AAGCCGCGGGAGGAGCAGTACAACAGCACGTACCGTGTGGTCAGCGTCCT
CACCGTCCTGCACCAGGACTGGCTGAATGGCAAGGAGTACAAGTGCAAGG
TCTCCAACAAAGCCCTCCCAGCCCCATCGAGAAAACCATCTCCAAAGCC
AAAGGGCAGCCCCGAGAACCACAGGTGTACACCCTGCCCCCATCCCGGGA
TGAGCTGACCAAGAACCAGGTCAGCCTGACCTGCCTGGTCAAAGGCTTCT
ATCCCAGCGACATCGCCGTGGAGTGGGAGAGCAATGGGCAGCCGGAGAAC
AACTACAAGACCACGCCTCCCGTGCTGGACTCCGACGGCTCCTTCTTCCT
CTACAGCAAGCTCACCGTGGACAAGAGCAGGTGGCAGCAGGGGAACGTCT
TCTCATGCTCCGTGATGCATGAGGCTCTGCACAACCACTACACGCAGAAG
AGCCTCTCCCTGTCTCCGGGTTAG.
```

In some embodiments, the nucleic acid sequence is:

```
                                            (SEQ ID NO: 32)
ATGGAATGGAGCTGGGTCTTTCTCTTCTTCCTGTCAGTAACGACTGGTGT
CCACTCCTTCGTGAACCAGCACCTGTGCGGCTCCCACCTGGTGGAAGCTC
TGGCTCTCGTGTGCGGCGAGGAGGGCTTCTTCTACACCCCCAAGGCCGCT
AAAGGCATCGTGGAACAGTGCTGCACCTCCATCTGCTCCCTGTACCAGCT
GGAAAACTACTGCAATGGCGGAGGTGGTGCAGGAGGCGGTGGAGACAAAA
CTCACACATGCCCACCGTGCCCAGCACCTGAACTCCTGGGGGGACCGTCA
GTCTTCCTCTTCCCCCCAAAACCCAAGGACACCCTCATGATCTCCCGGAC
CCCTGAGGTCACATGCGTGGTGGTGGACGTGAGCCACGAAGACCCTGAGG
TCAAGTTCAACTGGTACGTGGACGGCGTGGAGGTGCATAATGCCAAGACA
AAGCCGCGGGAGGAGCAGTACAACAGCACGTACCGTGTGGTCAGCGTCCT
CACCGTCCTGCACCAGGACTGGCTGAATGGCAAGGAGTACAAGTGCAAGG
TCTCCAACAAAGCCCTCCCAGCCCCATCGAGAAAACCATCTCCAAAGCC
AAAGGGCAGCCCCGAGAACCACAGGTGTACACCCTGCCCCCATCCCGGGA
TGAGCTGACCAAGAACCAGGTCAGCCTGACCTGCCTGGTCAAAGGCTTCT
ATCCCAGCGACATCGCCGTGGAGTGGGAGAGCAATGGGCAGCCGGAGAAC
AACTACAAGACCACGCCTCCCGTGCTGGACTCCGACGGCTCCTTCTTCCT
CTACAGCAAGCTCACCGTGGACAAGAGCAGGTGGCAGCAGGGGAACGTCT
TCTCATGCTCCGTGATGCATGAGGCTCTGCACAACCACTACACGCAGAAG
AGCCTCTCCCTGTCTCCGGGTTAG.
```

In some embodiments, the nucleic acid sequence is:

```
                                            (SEQ ID NO: 33)
ATGGAATGGAGCTGGGTCTTTCTCTTCTTCCTGTCAGTAACGACTGGTGT
CCACTCCTTCGTGAACCAGCACCTGTGCGGCTCCCACCTGGTGGAAGCTC
TGGCTCTCGTGTGCGGCGAGCGGGCTTCTTCTACACCCCCAAGGCCGCT
AAAGGCATCGTGGAACAGTGCTGCACCTCCATCTGCTCCCTGTACCAGCT
GGAAAACTACTGCAATGACAAAACTCACACATGCCCACCGTGCCCAGCAC
CTGAACTCCTGGGGGGACCGTCAGTCTTCCTCTTCCCCCCAAAACCCAAG
GACACCCTCATGATCTCCCGGACCCCTGAGGTCACATGCGTGGTGGTGGA
CGTGAGCCACGAAGACCCTGAGGTCAAGTTCAACTGGTACGTGGACGGCG
TGGAGGTGCATAATGCCAAGACAAAGCCGCGGGAGGAGCAGTACAACAGC
ACGTACCGTGTGGTCAGCGTCCTCACCGTCCTGCACCAGGACTGGCTGAA
TGGCAAGGAGTACAAGTGCAAGGTCTCCAACAAAGCCCTCCCAGCCCCCA
TCGAGAAAACCATCTCCAAAGCCAAAGGGCAGCCCCGAGAACCACAGGTG
TACACCCTGCCCCCATCCCGGGATGAGCTGACCAAGAACCAGGTCAGCCT
GACCTGCCTGGTCAAAGGCTTCTATCCCAGCGACATCGCCGTGGAGTGGG
AGAGCAATGGGCAGCCGGAGAACAACTACAAGACCACGCCTCCCGTGCTG
GACTCCGACGGCTCCTTCTTCCTCTACAGCAAGCTCACCGTGGACAAGAG
CAGGTGGCAGCAGGGGAACGTCTTCTCATGCTCCGTGATGCATGAGGCTC
TGCACAACCACTACACGCAGAAGAGCCTCTCCCTGTCTCCGGGTTAG.
```

In some embodiments, the nucleic acid sequence is:

```
                                            (SEQ ID NO: 34)
ATGGAATGGAGCTGGGTCTTTCTCTTCTTCCTGTCAGTAACGACTGGTGT
CCACTCCTTCGTGAACCAGCACCTGTGCGGCTCCCACCTGGTGGAAGCTC
TGGCTCTCGTGTGCGGCGAGCGGGGCTTCTTCTACACCCCCAAGGCCGCT
AAAGGCATCGTGGAACAGTGCTGCACCTCCATCTGCTCCCTGTACCAGCT
GGAAAACTACTGCAATGGCGGAGGTGGTTCAGGAGGCGGTGGAGACAAAA
```

```
-continued
CTCACACATGCCCACCGTGCCCAGCACCTGAACTCCTGGGGGACCGTCA

GTCTTCCTCTTCCCCCCAAAACCCAAGGACACCCTCATGATCTCCCGGAC

CCCTGAGGTCACATGCGTGGTGGTGGACGTGAGCCACGAAGACCCTGAGG

TCAAGTTCAACTGGTACGTGGACGGCGTGGAGGTGCATAATGCCAAGACA

AAGCCGCGGGAGGAGCAGTACAACAGCACGTACCGTGTGGTCAGCGTCCT

CACCGTCCTGCACCAGGACTGGCTGAATGGCAAGGAGTACAAGTGCAAGG

TCTCCAACAAAGCCCTCCCAGCCCCCATCGAGAAAACCATCTCCAAAGCC

AAAGGGCAGCCCCGAGAACCACAGGTGTACACCCTGCCCCCATCCCGGGA

TGAGCTGACCAAGAACCAGGTCAGCCTGACCTGCCTGGTCAAAGGCTTCT

ATCCCAGCGACATCGCCGTGGAGTGGGAGAGCAATGGGCAGCCGGAGAAC

AACTACAAGACCACGCCTCCCGTGCTGGACTCCGACGGCTCCTTCTTCCT

CTACAGCAAGCTCACCGTGGACAAGAGCAGGTGGCAGCAGGGGAACGTCT

TCTCATGCTCCGTGATGCATGAGGCTCTGCACAACCACTACACGCAGAAG

AGCCTCTCCCTGTCTCCGGGTTAG.
```

In some embodiments, the nucleic acid sequence is:

```
                                           (SEQ ID NO: 35)
ATGGAATGGAGCTGGGTCTTTCTCTTCTTCCTGTCAGTAACGACTGGTGT

CCACTCCTTCGTGAACCAGCACCTGTGCGGCTCCCACCTGGTGGAAGCTC

TGGCTCTCGTGTGCGGCGAGCGGGCTTCTTCTACACCCCCAAGGCCGCT

GCAAAAGGCATCGTGGAACAGTGCTGCACCTCCATCTGCTCCCTGTACCA

GCTGGAAAACTACTGCAATGGCGGAGGTGGTGCAGGAGGCGGTGGAGACA

AAACTCACACATGCCCACCGTGCCCAGCACCTGAACTCCTGGGGGACCG

TCAGTCTTCCTCTTCCCCCCAAAACCCAAGGACACCCTCATGATCTCCCG

GACCCCTGAGGTCACATGCGTGGTGGTGGACGTGAGCCACGAAGACCCTG

AGGTCAAGTTCAACTGGTACGTGGACGGCGTGGAGGTGCATAATGCCAAG

ACAAAGCCGCGGGAGGAGCAGTACAACAGCACGTACCGTGTGGTCAGCGT

CCTCACCGTCCTGCACCAGGACTGGCTGAATGGCAAGGAGTACAAGTGCA

AGGTCTCCAACAAAGCCCTCCCAGCCCCCATCGAGAAAACCATCTCCAAA

GCCAAAGGGCAGCCCCGAGAACCACAGGTGTACACCCTGCCCCCATCCCG

GGATGAGCTGACCAAGAACCAGGTCAGCCTGACCTGCCTGGTCAAAGGCT

TCTATCCCAGCGACATCGCCGTGGAGTGGGAGAGCAATGGGCAGCCGGAG

AACAACTACAAGACCACGCCTCCCGTGCTGGACTCCGACGGCTCCTTCTT

CCTCTACAGCAAGCTCACCGTGGACAAGAGCAGGTGGCAGCAGGGGAACG

TCTTCTCATGCTCCGTGATGCATGAGGCTCTGCACAACCACTACACGCAG

AAGAGCCTCTCCCTGTCTCCGGGTTAG.
```

In some embodiments, the nucleic acid sequence is:

```
                                           (SEQ ID NO: 36)
ATGGAATGGAGCTGGGTCTTTCTCTTCTTCCTGTCAGTAACGACTGGTGT

CCACTCCTTCGTGAACCAGCACCTGTGCGGCTCCCACCTGGTGGAAGCTC

TGGCTCTCGTGTGCGGCGAGCGGGCTTCTTCTACACCCCCAAGGCCGCT
```

```
-continued
GCAGCTAAAGGCATCGTGGAACAGTGCTGCACCTCCATCTGCTCCCTGTA

CCAGCTGGAAAACTACTGCAATGGCGGAGGTGGTGCAGGAGGCGGTGGAG

ACAAAACTCACACATGCCCACCGTGCCCAGCACCTGAACTCCTGGGGGA

CCGTCAGTCTTCCTCTTCCCCCCAAAACCCAAGGACACCCTCATGATCTC

CCGGACCCCTGAGGTCACATGCGTGGTGGTGGACGTGAGCCACGAAGACC

CTGAGGTCAAGTTCAACTGGTACGTGGACGGCGTGGAGGTGCATAATGCC

AAGACAAAGCCGCGGGAGGAGCAGTACAACAGCACGTACCGTGTGGTCAG

CGTCCTCACCGTCCTGCACCAGGACTGGCTGAATGGCAAGGAGTACAAGT

GCAAGGTCTCCAACAAAGCCCTCCCAGCCCCCATCGAGAAAACCATCTCC

AAAGCCAAAGGGCAGCCCCGAGAACCACAGGTGTACACCCTGCCCCCATC

CCGGGATGAGCTGACCAAGAACCAGGTCAGCCTGACCTGCCTGGTCAAAG

GCTTCTATCCCAGCGACATCGCCGTGGAGTGGGAGAGCAATGGGCAGCCG

GAGAACAACTACAAGACCACGCCTCCCGTGCTGGACTCCGACGGCTCCTT

CTTCCTCTACAGCAAGCTCACCGTGGACAAGAGCAGGTGGCAGCAGGGGA

ACGTCTTCTCATGCTCCGTGATGCATGAGGCTCTGCACAACCACTACACG

CAGAAGAGCCTCTCCCTGTCTCCGGGTTAG.
```

Linkers

In some embodiments, an insulin-Fc fusion protein described herein comprises one or more linkers, e.g., between one or more domains of the insulin-Fc fusion protein, or between the insulin-Fc fusion protein and a conjugated molecule/moiety. For example, an insulin-Fc fusion protein comprises a linker between the insulin polypeptide and the Fc fragment. In other embodiments, an insulin-Fc fusion protein comprises a linker between one or more peptides (e.g., A-chain, B-chain, and/or C-chain peptides) of the insulin polypeptide.

Peptide linkers may comprise natural or unnatural amino acids. In some embodiments, peptide linkers can be encoded by a nucleic acid molecule, e.g., such that a single nucleic acid molecule can encode the various peptides within an insulin polypeptide as well as the peptide linker(s); or can encode the insulin polypeptide, the Fc fragment, and the peptide linker.

In some embodiments, the peptide linker comprises at least 5 amino acid residues, e.g., at least 5, 6, 7, 8, 9, 10, 11, 12, 13, 14, 15, 16, 17, 18, 19, 20 or more amino acid residues. In some embodiments, the peptide linker comprises 5-9 amino acid residues. In some embodiments, the peptide linker comprises four or less amino acids or six or more amino acids in length. In some embodiments, the peptide linker comprises 0 amino acids (e.g. no peptide linker). In some embodiments, the peptide linker comprises 4 or more glycines (e.g., 4, 5, 6, 7, 8, or more glycines). In some embodiments, the peptide linker comprises 4 or more consecutive glycines (e.g., 5 or more consecutive glycines). In some embodiments, the peptide linker comprises the amino acid sequence of GGGGAGGGG (SEQ ID NO: 20) or GGGGSGGGG (SEQ ID NO: 21). In some embodiments, the peptide linker comprises the linker in the etanercept fusion protein. See, e.g., U.S. Pat. No. 8,063,182 B1, incorporated herein by reference. In some embodiments, the peptide linker does not comprise the "hinge" region (or a fragment thereof) of a human immunoglobulin (e.g., an IgG, e.g., IgG$_1$).

The "hinge" region of a human immunoglobulin is often divided into three regions: the upper, middle, and lower hinge. In some embodiments, in an immunoglobulin, the upper hinge is the number of amino acids between the end of the first domain of the heavy chain (CH1) and the first cysteine forming an interheavy chain disulfide bridge. The middle hinge is high in proline and contains the inter-heavy chain cysteine disulfide bridges. The lower hinge connects the middle hinge to the CH2 domain. See Sandlie, I. and Michaelsen, T., Chapter 3: Engineering the Hinge Region to Optimize Complement-induced Cytolysis, In *Antibody Engineering: A Practical Guide*, W. H. Freeman and Co., New York, N.Y.; see also Hamers-Castennan, C., Naturally Occurring Antibodies Devoid of Light Chains, 363 *Nature* 446 (1993) and Terskikh, A. V., "Peptabody": A New Type of High Avidity Binding Protein, 94 *Proc. Natl. Acad. Sci. USA* 1663 (1997).

Functional Features of the Insulin-Fc Fusion Proteins of the Present Technology

Described herein are methods for treating or preventing an autoimmune disease, e.g., autoimmune diabetes comprising the administration of an insulin-Fc fusion protein described herein to a subject, wherein the insulin-Fc fusion protein specifically binds to an anti-insulin antibody, binds to an anti-insulin B cell, decreases T cell interactions (as determined by IL-2 secretion), and/or exhibit weak binding to insulin receptor. Additionally or alternatively, in some embodiments, the insulin-Fc fusion protein binds human insulin receptor at an $IC_{50}$>3,000 nM (e.g., 4,000 nM, 5,000 nM, or higher) in a competitive binding assay.

Additionally or alternatively, in some embodiments, administration of an insulin-Fc fusion protein described herein does not have a substantial effect (e.g., substantial lowering effect) on glucose levels (e.g., blood glucose levels) in a subject. In some embodiments, the glucose lowering activity of the insulin-Fc fusion protein is lower (e.g., at least 10% lower, 20% lower, 30% lower, 40% lower, 50% lower, or at least 2-fold lower, e.g., at least 5-fold lower, 10-fold lower, 15-fold lower, 20-fold lower, 30-fold lower, 40-fold lower, 50-fold lower, etc.) than a reference standard. A reference standard can be a naturally occurring insulin (e.g., proinsulin or mature insulin) from a mammal, e.g., human or mouse. A reference standard can also be a fusion protein described in US 2013/0028918 A1 or CN 103509118A.

In some embodiments, the insulin-Fc fusion proteins described herein specifically target B cells that react with a particular islet autoantigen, e.g., the insulin-Fc fusion proteins do not target B cells that do not react with that particular islet autoantigen. For example, the insulin-Fc fusion proteins described herein specifically target B cells that react with insulin (also called insulin-specific B cells, insulin$^+$ B cells, insulin$^+$ B220$^+$ cells, or anti-insulin B cells). In some embodiments, the insulin-Fc fusion proteins of the present technology do not target non-insulin-specific B cells. Thus, the insulin-Fc fusion proteins described herein advantageously have high specificity for particular B cells, e.g., autoimmune B cells expressing anti-insulin receptors (e.g., anti-insulin BCRs, anti-insulin B cells, or insulin$^+$ B cells).

In some embodiments, the insulin-Fc fusion proteins described herein bind to specific types of B cells, e.g., autoantigen-specific B cells or autoimmune B cells (e.g., anti-insulin B cells, insulin-specific B cells, or insulin$^+$ B cells), and target them for elimination, e.g., via phagocytosis by macrophages or dendritic cells, or via antibody dependent cell-mediated cytotoxicity (ADCC) or complement mediated cytotoxicity (CDC). In some embodiments, the insulin-Fc fusion proteins described herein do not target non-autoantigen-specific B cells or non-autoimmune B cells (e.g., cells other than anti-insulin B cells) for elimination Eliminating autoimmune B cells or autoantigen-specific B cells, e.g., insulin-specific B cells, may decrease the autoimmune response, level of autoantibodies, and ultimately treats or prevents an autoimmune disease, such as autoimmune (e.g., Type I) diabetes.

In some embodiments, the insulin-Fc fusion protein may function by targeting a specific entity, e.g., a B cell, an autoimmune antibody, a specific immunoglobulin B cell receptor, or other protein or cell. In some embodiments, the insulin-Fc fusion protein functions by targeting a B cell, e.g., a B cell that is specific for an islet autoantigen, e.g., a B cell containing a B cell receptor that binds insulin. In some embodiments, the insulin-Fc fusion protein functions by targeting an anti-insulin B cell, e.g., a B cell containing a B cell receptor that binds insulin. In some embodiments, the insulin-Fc fusion protein is a homodimer containing two proinsulin or proinsulin analogs, and is able to simultaneously bind to multiple (e.g. more than one) anti-insulin B cell receptors on the same B cell, which causes the insulin-Fc fusion protein to be endocytosed. In some embodiments, the insulin-Fc fusion protein is a homodimer containing two proinsulin or proinsulin analogs, and is able to simultaneously bind to multiple (e.g. more than one) anti-insulin B cell receptors on the B same cell, which causes a signaling event within the B cell. In some embodiments, the insulin-Fc fusion protein is a homodimer containing two proinsulin or proinsulin analogues, and is able to simultaneously bind to multiple (e.g. more than one) anti-insulin B cell receptors on the same B cell, which causes the B cell to undergo apoptosis. In some embodiments, the insulin-Fc fusion protein is a homodimer containing two proinsulin or proinsulin analogues, and is able to simultaneously bind to multiple (e.g. more than one) anti-insulin B cell receptors on the same B cell, while epitopes on the Fc region of the insulin-Fc fusion protein interact with immune effector cells to elicit an effect on the B cell (e.g. apoptosis through ADCC). In some embodiments, the insulin-Fc fusion protein binds to an anti-insulin B cell that is an early-stage B cell and causes the early B cell to modify its B cell receptor through a process known as receptor editing.

In one aspect, provided herein is a method of treating an autoimmune disease (e.g., autoimmune diabetes), comprising administering to a subject an insulin-Fc fusion protein described herein, wherein administration of the insulin-Fc fusion protein results in a decrease in autoantigen-specific B cell levels in the subject relative to a reference standard or reference treatment. In another aspect, provided herein is a method of treating an autoimmune disease (e.g., autoimmune diabetes), comprising administering to a subject an insulin-Fc fusion protein described herein, wherein administration of the insulin-Fc fusion protein induces autoantigen-specific B cells in the subject to undergo increased receptor editing relative to a reference standard or reference treatment. In some embodiments, the B cell is specific for an autoantigen (e.g., the B cell comprises a BCR comprising an immunoglobulin that binds an autoantigen, e.g., insulin).

In some embodiments, the B cell comprises a disease-causing B cell or a pathogenic B cell (e.g., anti-insulin B cells, insulin-specific B cells, or insulin$^+$ B cells). In some embodiments, the B cell comprises an anti-insulin B cell. In some embodiments, the B cell presents a specific cell surface receptor. In some embodiments, the anti-insulin B cell surface receptor comprises B220, CD19, CD20, CD22, and other similar cell surface receptors and isoforms thereof. In some embodiments, the anti-insulin B cell presents a combination of cell surface receptors comprising B220, CD19, CD20, CD22, and other similar cell surface receptors and isoforms thereof. In some embodiments, the anti-insulin B cell presents a B cell receptor (BCR) specific to insulin, e.g., the BCR comprises an immunoglobulin specific for insulin, e.g., an IgM receptor.

In some embodiments, administration of the insulin-Fc fusion protein leads to elimination of greater than 10% (e.g., greater than 10%, 20%, 30%, 40%, 50%, 60%, 70%, 80%, 90% or more) of the insulin-specific B cells present in the subject (e.g., in blood or spleen) prior to treatment with the insulin-Fc fusion protein. Additionally or alternatively, in some embodiments, administration of the insulin-Fc fusion protein leads to elimination of fewer than 30% (e.g., fewer than 30%, 25%, 20%, 15%, 10%, 5%, 2.5%, 1% or fewer) of the non-insulin-specific/reactive B cells present in the subject prior to treatment with the insulin-Fc fusion protein. In some embodiments, administration of the insulin-Fc fusion protein leads to elimination of fewer than 30% (e.g., fewer than 30%, 25%, 20%, 15%, 10%, 5%, 2.5%, 1% or fewer) of the total number of B cells (which includes both insulin-specific B cells and non-insulin-specific B cells) present in the subject prior to treatment with the insulin-Fc fusion protein.

In some embodiments, administration of the insulin-Fc fusion protein leads to a reduction (e.g., by at least 2-fold, e.g., at least 2, 4, 6, 8, 10, 15, 20, 25, 30, 35, 40, 45, 50, 100, 150, 200, 250, 300, 400, 500, 1000, or 10,000-fold or more) of the number of insulin-specific B cells (compared to that observed prior to treatment with the insulin-Fc fusion protein) for at least 1 day (e.g., at least 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 days or more, e.g., at least 1, 2, 3, 4, 5, 6, 7, 8, 9, 10 weeks or more) after treatment.

In some embodiments, the insulin-Fc fusion protein, e.g., when administered chronically to a subject, leads to a reduction (e.g., by at least 2-fold, e.g., at least 2, 4, 6, 8, 10, 15, 20, 25, 30, 35, 40, 45, 50, 100, 150, 200, 250, 300, 400, 500, 1000, or 10,000-fold or more) of the number of insulin-specific B cells (compared to that observed prior to treatment with the insulin-Fc fusion protein) during the course of the treatment and, in some cases, for a period of time after cessation of the treatment, e.g., at least 1 day (e.g., at least 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 days or more, e.g., at least 1, 2, 3, 4, 5, 6, 7, 8, 9, 10 weeks or more) after cessation of the treatment.

Exemplary methods of determining the number of cells eliminated by insulin-Fc fusion protein treatment are described in the Examples section. For example, a determination of the amount of cells eliminated can be performed using an in vitro co-culture of macrophages (e.g., rat alveolar macrophages) with splenocytes that contain a transgene expressing an anti-insulin antibody fragment (e.g., splenocytes from a VH-125 mouse). See, e.g., Hulbert, et al., *J. Immunol.* 167(2001):5535-38. In another example, a determination of the amount of cells eliminated can be performed by measuring the level of B cells (e.g., autoantigen-specific) in peripheral blood of a subject. For example, a reduction in the number of autoantigen-specific B cells after treatment with an insulin-Fc fusion protein compared to that observed prior to treatment indicates that administration of the insulin-Fc fusion protein leads to elimination of the autoantigen-specific B cells. A small (or no) reduction in the number of total B cells or non-insulin specific B cells indicates that the insulin-Fc fusion protein does not lead to global non-specific elimination of B cells, i.e., the insulin-Fc fusion protein is specific for the autoantigen-specific B cells.

In some embodiments, the insulin-Fc fusion protein has an affinity for an anti-insulin antibody (e.g., soluble, e.g., circulating, or bound to receptor) characterized by a $K_d$ of 1 µM or lower, e.g., 1 µM, 900 nM, 800 nM, 700 nM, 600 nM, 500 nM, 400 nM, 300 nM, 200 nM, 100 nM, 50 nM, 10 nM, 5 nM, 1 nM, 0.1 nM, 0.01 nM, 0.001 nM, or lower). In some embodiments, the insulin-Fc fusion protein has an affinity for an anti-insulin immunoglobulin or a B cell receptor (BCR) (e.g., on an insulin-specific B cell) greater than (e.g., at least 2-fold greater than, e.g., at least 2, 4, 6, 8, 10, 15, 20, 25, 30, 35, 40, 45, 50, 100, 150, 200, 250, 300, 400, 500, 1000, or 10,000-fold or more greater than) that of the insulin hormone receptor.

In some embodiments, the insulin-Fc fusion protein has an affinity for an insulin-specific B cell, characterized by a Kd of 1 µM or lower, e.g., 1 µM, 900 nM, 800 nM, 700 nM, 600 nM, 500 nM 400 nM, 300 nM, 200 nM, 100 nM, 50 nM, 10 nM, 5 nM, 1 nM, 0.1 nM, 0.01 nM, 0.001 nM, or lower). In some embodiments, the insulin-Fc fusion protein has an affinity for the insulin-specific B cell that is lower than (e.g., at least 2-fold greater than, e.g., at least 2, 4, 6, 8, 10, 15, 20, 25, 30, 35, 40, 45, 50, 100, 150, 200, 250, 300, 400, 500, 1000, or 10,000-fold or more lower than) its affinity to a non-insulin specific/reactive B cell.

Additionally or alternatively, in some embodiments, the insulin-Fc fusion protein inhibits in vitro binding of insulin$^+$ B cell receptors to insulin at an $IC_{50}$<300 nM (e.g., 250 nM, 200 nM, 150 nM, 100 nM, 95 nM, 90 nM, 85 nM, 80 nM, 75 nM, 70 nM, 65 nM, 60 nM, 55 nM, 50 nM, 45 nM, 40 nM, 35 nM, 30 nM, 25 nM, 20 nM, 15 nM, 10 nM, 5 nM, 4 nM, 3 nM, 2 nM, 1 nM or lower).

Additionally or alternatively, in some embodiments, the insulin-Fc fusion protein deletes insulin-specific B cells in vitro at an $EC_{50}$ of about 70 pM.

In some embodiments, the insulin-Fc fusion protein is capable of binding to insulin autoantibodies (e.g., in vivo or in vitro) with a binding affinity that is at least 5% of that observed with human insulin. In some embodiments, the insulin-Fc fusion protein is capable of binding to insulin autoantibodies (e.g., in vivo or in vitro) with a binding affinity that is about 5%, about 10%, about 15%, about 20%, about 25%, about 30%, about 35%, about 40%, about 50%, about 55%, about 60%, about 65%, about 70%, about 75%, about 80%, about 85%, about 90%, about 95%, about 99% or about 100% of that observed with human insulin.

In some embodiments, the insulin-Fc fusion protein is capable of binding to a B cell receptor (e.g., in vivo or in vitro) with a binding affinity that is at least 5% of that observed with human insulin. In some embodiments, the insulin-Fc fusion protein is capable of binding to a B cell receptor (e.g., in vivo or in vitro) with a binding affinity that is about 5%, about 10%, about 15%, about 20%, about 25%, about 30%, about 35%, about 40%, about 50%, about 55%, about 60%, about 65%, about 70%, about 75%, about 80%, about 85%, about 90%, about 95%, about 99% or about 100% of that observed with human insulin.

An antigen presenting cell (APC) is a cell that displays an antigen complexed with a major histocompatibility complex molecule (MHC), e.g., an MHCII molecule, on its cell surface through the process of antigen presentation.

In some embodiments, the insulin-Fc fusion proteins of the present technology are capable of being processed by antigen presenting cells (APCs) into peptides. These APC-processed peptides can then be presented onto an APC MHCII receptor in the form of peptide-MHCII complexes that are capable of binding to T cell receptors. In some embodiments, these APC-processed peptide-MHC II complexes are capable of binding to a T cell receptor (e.g., in vivo or in vitro) with a binding affinity that is about 5%, about 10%, about 15%, about 20%, about 25%, about 30%, about 35%, about 40%, about 50%, about 55%, about 60%, about 65%, about 70%, about 75%, about 80%, about 85%, about 90%, about 95%, about 99% or about 100% higher than that observed with human insulin peptide-MHC II complexes, e.g., human insulin B9:23 peptide-MHC II complexes.

In some embodiments, administration of the insulin-Fc fusion protein results in a decrease in the level of insulin autoantibody (IAA) (e.g., circulating IAA) levels in a subject after administration, e.g., a decrease of at least 2-fold, e.g., at least 2, 4, 6, 8, 10, 15, 20, 25, 30, 35, 40, 45, 50, 100, 150, 200, 250, 300, 400, 500, 1000, or 10,000-fold greater. In some embodiments, administration of the insulin-Fc fusion protein results in a reduction in the insulin autoantibody (IAA) (e.g., circulating IAA) levels in a subject compared to that observed with treatment with an insulin or insulin analog that is not fused to an Fc fragment.

In some embodiments, an insulin-Fc fusion protein described herein results in decreased T cell activation in vivo and/or in vitro, e.g., relative to a naturally occurring human insulin, e.g., human proinsulin or human mature insulin. In some embodiments, an insulin-Fc fusion protein described herein, when contacted with B cells in vitro or in vivo, is processed by a B cell and presented as an antigen (e.g., at least the B-chain peptide or a portion of the B-chain peptide is presented) in a MHCII complex to T cells.

In still further embodiments, an insulin-Fc fusion protein described herein, when contacted with antigen presenting cells (e.g., dendritic cells or macrophages) in vitro or in vivo, is processed by an antigen presenting cell and presented as an antigen (e.g., at least the B-chain peptide or a portion of the B-chain peptide is presented) in a MHCII complex to T cells. In some embodiments, where the insulin-Fc fusion protein comprises a B-chain peptide comprising a Y16A mutation, the extent of recognition of this B-chain peptide: MHCII complex by T cells is reduced relative to an insulin-Fc fusion protein comprising a B-chain peptide from wild-type human insulin (e.g., which comprises Y16), where the numbering of the mutation refers to the position in the insulin B chain relative to the N-terminus. In some embodiments, an insulin-Fc fusion protein described herein results in less T cell activation in vivo and/or in vitro compared to a fusion protein described in US 2013/0028918 A1 or CN 103509118A.

Additionally or alternatively, in some embodiments, the insulin-Fc fusion protein activates T-cells to secrete IL-2 levels that are reduced compared to that observed in T-cells activated by recombinant human insulin. In some embodiments, the the insulin-Fc fusion protein activates T-cells to secrete IL-2 levels that are less than 3,000 pg/ml (e.g., 2750 pg/mL, 2500 pg/mL, 2250 pg/mL, 2000 pg/mL, 1750 pg/mL, 1500 pg/mL, 1250 pg/mL, 1000 pg/mL, 750 pg/mL, 500 pg/mL, 250 pg/mL, 200 pg/mL, 175 pg/ml, 150 pg/ml, 125 pg/ml, 100 pg/ml, 95 pg/ml, 90 pg/ml, 85 pg/ml, 80 pg/ml, 75 pg/ml, 70 pg/ml, 65 pg/ml, 60 pg/ml, 55 pg/ml, 50 pg/ml, 45 pg/ml, 40 pg/ml, 35 pg/ml or lower).

In some embodiments, the insulin-Fc fusion protein inhibits T-cell activation induced by a reference standard at an $IC_{50}$ of 100 nM or less (e.g., 100 nM, 95 nM, 90 nM, 85 nM, 80 nM, 75 nM, 70 nM, 65 nM, 60 nM, 55 nM, 50 nM, 45 nM, 40 nM, 35 nM, 30 nM, 25 nM, 20 nM, 15 nM, 10 nM, 9 nM, 8 nM, 7 nM, 6 nM, 5 nM, 4 nM, 3 nM, 2 nM, 1 nM, 0.9 nM, 0.8 nM, 0.7 nM, 0.6 nM, 0.5 nM, 0.4 nM, 0.3 nM, 0.2 nM, 0.1 nM, 0.01 nM, 0.001 nM, or lower), wherein the reference standard is an insulin-Fc protein having the amino acid sequence of SEQ ID NO: 5. In some embodiments, the insulin-Fc fusion protein inhibits T-cell activation induced by a reference standard at an $IC_{50}$ of 5 nM or less, wherein the reference standard is an insulin-Fc protein having the amino acid sequence of SEQ ID NO: 5.

In some embodiments, an insulin-Fc fusion protein described herein, when administered to a subject, decreases the incidence of an autoimmune disease, e.g., autoimmune diabetes, compared to a reference standard. A reference standard can be a naturally occurring insulin (e.g., proinsulin or mature insulin) from a mammal, e.g., human or mouse.

In some embodiments, an insulin-Fc fusion protein described herein has a serum half-life of at least 2 h (e.g., at least 2 h, 5 h, 10 h, 15 h, 20 h, 24 h, 36 h, 1 day, 1.5 days, 2 days, 2.2 days, 2.5 days, 3 days, 5 days, 7 days, or more) when administered to a subject. In some embodiments, an insulin-Fc fusion protein described herein has a longer serum half-life than a reference standard. A reference standard can be a naturally occurring insulin (e.g., proinsulin or mature insulin) from a mammal, e.g., human or mouse. A reference standard can also be a peptide (e.g. an insulin B-chain peptide, or an insulin B-chain peptide containing one or more amino acid mutations). A reference standard can also be a fusion protein described in US 2013/0028918 A1 or CN 103509118A.

Additionally or alternatively, in some embodiments of the methods disclosed herein, administration of the insulin-Fc fusion protein results in a reduced number of anti-insulin B cells in the subject (e.g., in blood or spleen) compared to that observed in the subject prior to administration (e.g., reduction by at least 5%, e.g., at least 5%, 10%, 15%, 20%, 30%, 40%, 50%, 60%, 70%, 80%, 90%, 100%, 2-fold, 3-fold, 4-fold, 5-fold, 10-fold, or more). In certain embodiments, administration of the insulin-Fc fusion protein does not substantially reduce the number of B cells other than anti-insulin B cells. In some embodiments of the methods disclosed herein, the subject displays a reduction in the number of anti-insulin B cells 1 day, 2 days, 3 days, 4 days, 5 days, 6 days, 7 days, 8 days, 9 days, 10 days, 11 days, 12 days, 13 days, 2 weeks, 3 weeks, or more than 3 weeks after administration of the insulin-Fc fusion protein compared to that observed in the subject prior to administration.

Additionally or alternatively, in some embodiments of the methods disclosed herein, administration of the insulin-Fc fusion protein results in decreased levels of insulin autoantibody in the subject (e.g., circulating IAA) compared to that observed in the subject prior to administration (e.g., a decrease of at least 5%). In some embodiments of the methods disclosed herein, the subject displays decreased levels of insulin autoantibody 1 day, 2 days, 3 days, 4 days, 5 days, 6 days, 7 days, 8 days, 9 days, 10 days, 11 days, 12 days, 13 days, 2 weeks, 3 weeks, or more than 3 weeks after administration of the insulin-Fc fusion protein compared to that observed in the subject prior to administration.

Additionally or alternatively, in some embodiments of the methods disclosed herein, the blood glucose levels of the subject after administration of the insulin-Fc fusion protein are comparable to that observed in the subject prior to administration. In some embodiments of the methods disclosed herein, the blood glucose levels of the subject 1 day, 2 days, 3 days, 4 days, 5 days, 6 days, 7 days, 8 days, 9 days, 10 days, 11 days, 12 days, 13 days, 2 weeks, 3 weeks, or more than 3 weeks after administration of the insulin-Fc fusion protein are comparable to that observed in the subject prior to administration.

Insulin-Fc Fusion Protein Production

Various procedures may be used for the production of the insulin-Fc fusion proteins described herein. (See, for example, Antibodies: A Laboratory Manual, Harlow E, and Lane D, 1988, Cold Spring Harbor Laboratory Press, Cold Spring Harbor, N.Y., incorporated herein by reference).

Vectors.

An insulin-Fc fusion protein can be expressed by a vector comprising any of the DNA sequences encoding an insulin-Fc fusion protein of the present technology as described herein. These can include nucleic acid vectors, liposomes, naked DNA, adjuvant-assisted DNA, gene gun, catheters, etc. Vectors can include chemical conjugates such as described in WO 93/64701, which has targeting moiety (e.g. a ligand to a cellular surface receptor) and a nucleic acid binding moiety (e.g. polylysine), viral vectors (e.g. a DNA or RNA viral vectors), plasmids, phages, etc. The vectors can be chromosomal, non-chromosomal or synthetic.

Exemplary vectors include viral vectors, fusion proteins and chemical conjugates. Retroviral vectors include moloney murine leukemia viruses. In some embodiments, the viral vector is a DNA viral vector. Exemplary DNA vectors include pox vectors such as orthopox or avipox vectors, herpesvirus vectors such as a herpes simplex I virus (HSV) vector (see Geller, A. I. et al., J. Neurochem, 64:487 (1995); Lim, F., et al., in DNA Cloning: Mammalian Systems, D. Glover, Ed. (Oxford Univ. Press, Oxford England) (1995); Geller, A. I. et al., Proc Natl. Acad. Sci.: U.S.A. 90:7603 (1993); Geller, A. I., et al., Proc Natl. Acad. Sci. USA 87:1149 (1990), Adenovirus Vectors (see LeGal LaSalle et al., Science, 259:988 (1993); Davidson, et al., Nat. Genet 3:219 (1993); Yang, et al., J. Virol. 69:2004 (1995) and Adeno-associated Virus Vectors (see Kaplitt, M. G. et al., Nat. Genet. 8:148 (1994).

Pox viral vectors introduce the gene into the cell cytoplasm. Avipox virus vectors result in only a short term expression of the nucleic acid. In some embodiments, adenovirus vectors, adeno-associated virus vectors and herpes simplex virus (HSV) vectors are used for introducing the nucleic acid into cells. The adenovirus vector results in a shorter term expression (about 2 months) than adeno-associated virus (about 4 months), which in turn is shorter than HSV vectors. The particular vector chosen will depend upon the target cell and the condition being treated. The introduction can be by standard techniques, e.g. infection, transfection, transduction or transformation. Examples of modes of gene transfer include e.g., naked DNA, $CaPO_4$ precipitation, DEAE dextran, electroporation, protoplast fusion, lipofection, cell microinjection, and viral vectors. These vectors can be used to express the insulin-Fc fusion proteins described herein. In some embodiments, an insulin-Fc fusion protein can be expressed by a vector described in the Examples section.

Cell Lines, Expression and Purification.

Also disclosed herein are host cells that express an insulin-Fc fusion protein of the present technology or a vector comprising any of the DNA sequences encoding an insulin-Fc fusion protein of the present technology.

In some embodiments, an insulin-Fc fusion protein can be expressed recombinantly, e.g., in a eukaryotic cell, e.g., mammalian cell or non-mammalian cell. Exemplary mammalian cells used for expression include HEK cells, e.g., HEK293 cells, or CHO cells, among other cell lines available in the art, e.g., cell lines used for expression of antibody fragments or Fc containing proteins. In some embodiments, non-mammalian cells, such as insect cells are used for expression of the insulin-Fc fusion proteins of the present technology, e.g., SF9 or S2 cells, among other cell lines available in the art, e.g., cell lines used for expression of antibody fragments or Fc containing proteins. In some embodiments, cells are transfected with a nucleic acid molecule, e.g., vector, encoding the insulin-Fc fusion protein (e.g., where the entire insulin-Fc fusion protein is encoded by a single nucleic acid molecule). In other embodiments, cells are transfected with more than one nucleic acid molecule, where each nucleic acid molecule encodes a different domain of the insulin-Fc fusion protein. For example, one nucleic acid molecule can encode the insulin polypeptide, and a different nucleic acid molecule can encode the Fc fragment. Cells can be cultured using standard methods in the art.

In some embodiments, the insulin-Fc fusion protein is purified or isolated from the cells (e.g., by lysis of the cells). In other embodiments, the insulin-Fc fusion protein is secreted by the cells and, e.g., the fusion protein is purified or isolated from the cell culture media in which the cells were grown. Purification of the insulin-Fc fusion protein can include using column chromatography, e.g., affinity chromatography, or using other separation methods that involve size, charge, and/or affinity for certain molecules. In some embodiments, purification of the insulin-Fc fusion protein involves selecting/enriching for proteins with an Fc fragment, e.g., by using Protein A beads or a Protein A column. Other affinity separation methods can be used, e.g., using anti-insulin antibodies or fragments thereof. Additionally or alternatively, other separation methods such as ion exchange chromatography and/or gel filtration chromatography can also be employed. In some embodiments, purification of the insulin-Fc fusion protein further comprises filtering or centrifuging the protein preparation.

The purified fusion protein can be characterized, e.g., for purity, yield, structure, and/or activity, using a variety of methods, e.g., absorbance at 280 nm (e.g., to determine yield), size exclusion or capillary electrophoresis (e.g., to determine the molecular weight and/or purity), mass spectrometry (MS) and/or liquid chromatography (LC)-MS (e.g., to determine purity and/or glycosylation), and/or ELISA (e.g., to determine extent of binding, e.g., affinity, to an anti-insulin antibody). Exemplary methods of characterization are also described in the Examples section.

In some embodiments, expression of an insulin-Fc fusion protein in a cell, e.g., cell culture, generates a yield of at least 50 mg of the insulin-Fc fusion protein (e.g., purified fusion protein) per liter of culture (e.g., at least 50 mg/L, 60 mg/L, 70 mg/L, 80 mg/L, 90 mg/L, 100 mg/L, 110 mg/L, 120 mg/L, or more). In some embodiments, a purified insulin-Fc fusion protein has a purity of at least 80% (e.g., at least 80%, 85%, 90%, 95%, 97%, 99% by weight), e.g., as determined by standard methods.

In some embodiments, expression of an insulin-Fc fusion protein described herein in a cell generates a yield of the insulin-Fc fusion protein (e.g., purified insulin-Fc fusion protein) that is greater than (e.g., at least 1.5-fold, 2-fold, 3-fold, 4-fold, 5-fold, 10-fold, 15-fold, 20-fold, 30-fold, 40-fold, 50-fold, or more) a fusion protein described in US 2013/0028918 A1 or CN 103509118A.

Therapeutic and Prophylactic Methods

The following discussion is presented by way of example only, and is not intended to be limiting.

Described herein are methods for treating or preventing an autoimmune disease (e.g., autoimmune diabetes, e.g., Type 1 diabetes), wherein the method comprises administering to a subject an insulin-Fc fusion protein described herein. In some embodiments of the methods disclosed herein, the autoimmune disease is autoimmune diabetes, e.g., diabetes mellitus type 1 (i.e., Type 1 diabetes (T1D), juvenile diabetes, or insulin-dependent diabetes), or latent autoimmune diabetes of adults (LADA). LADA, also referred to as slow onset Type 1 diabetes, is a form of diabetes mellitus type 1 that occurs in adults and presents with a slower course of onset. It is estimated that up to about 50% of adults diagnosed with non-obesity related Type 2 diabetes may have LADA. In some embodiments of the methods disclosed herein, the autoimmune disease comprises a decreased number of insulin-producing β-cells of the pancreas in a subject relative to a reference standard or normal control subject.

In some embodiments of the methods disclosed herein, the subject has been diagnosed with an autoimmune disease (e.g., autoimmune diabetes, e.g., Type 1 diabetes). In certain embodiments, the subject has been diagnosed with an autoimmune disease (e.g., autoimmune diabetes, e.g., Type 1 diabetes) for less than 3 months, less than 6 months, less than 9 months, less than 1 year, or less than 1.5 years.

Additionally or alternatively, in some embodiments of the methods disclosed herein, the subject has detectable levels of autoimmune antibody but has not developed symptoms of autoimmune disease (e.g., autoimmune diabetes, e.g., Type 1 diabetes), such as hyperglycemia. The autoimmune antibody may be specific for an islet-autoantigen. For example, in some embodiments, the islet-autoantigen comprises insulin, glutamate decarboxylase (e.g., isoform 65, e.g., anti-$GAD_{65}$), protein tyrosine phosphatase-like protein (IA2), or zinc transporter 8 (ZnT8). In other embodiments, the autoimmune antibody is an anti-insulin antibody.

In certain embodiments of the methods disclosed herein, the subject has no detectable levels of insulin autoantibody and has not developed symptoms of autoimmune disease (e.g., autoimmune diabetes, e.g., Type 1 diabetes), e.g., has not developed hyperglycemia.

In some embodiments of the methods disclosed herein, the subject has no detectable levels of a pathogenic B cell population or a disease-causing B cell population (e.g., anti-insulin B cells, insulin-specific B cells, or insulin$^+$ B cells) and has not developed symptoms of autoimmune disease (e.g., autoimmune diabetes, e.g., Type 1 diabetes), e.g., has not developed hyperglycemia.

In certain embodiments of the methods disclosed herein, the subject has detectable levels of a pathogenic B cell population or a disease-causing B cell population (e.g., anti-insulin B cells, insulin-specific B cells, or insulin$^+$ B cells) but has not developed symptoms of autoimmune disease (e.g., autoimmune diabetes, e.g., Type 1 diabetes), e.g., has not developed hyperglycemia. In some embodiments, the B cell population comprises an insulin-specific B cell. In some embodiments, the insulin-specific B cell presents a specific cell surface receptor such as B220, CD19, CD20, CD22, or other similar cell surface receptors and isoforms thereof. In certain embodiments, the insulin-specific B cell expresses two or more cell surface receptors such as B220, CD19, CD20, CD22, and other similar cell surface receptors and isoforms thereof.

Additionally or alternatively, in some embodiments of the methods disclosed herein, the level of endogenous C-peptide in a subject is assessed to aid in the diagnosis and extent of autoimmune diabetes (e.g., Type 1 diabetes or latent autoimmune diabetes). C-peptide is frequently utilized as a biomarker for residual β cell function, as it is produced in equal amounts to insulin and may therefore represent the total amount of insulin secretion in a subject (Jones, A. G. and Hattersley, A. T., *Diabet Med* (2013) 30, 803-817). Measurement of C-peptide in a subject may be useful in directing determination of insulin levels, as any exogenous insulin present in a subject will be also detected in direct insulin assays. A healthy subject (e.g., a subject without autoimmune diabetes) has an endogenous C-peptide level that ranges from about 0.6 nmol/L to about 0.8 nmol/L (e.g., about 0.65 nmol/L). In contrast, a subject with autoimmune diabetes (e.g., Type 1 diabetes or LADA) has an endogenous C-peptide level ranging from undetectable to about 0.6 nmol/L (e.g., about 0.05 nmol/L). In some embodiments, the endogenous C-peptide level does not include any C-peptide that is derived from the C-peptide of an insulin-Fc fusion protein described herein, e.g., after administration of an insulin-Fc fusion protein described herein.

In some embodiments, the subject has been diagnosed with autoimmune diabetes (e.g., Type 1 diabetes) and has an endogenous C-peptide level of equal to or less than about 0.01 nmol/L, about 0.02 nmol/L, about 0.03 nmol/L, about 0.04 nmol/L, about 0.05 nmol/L, about 0.06 nmol/L, about 0.07 nmol/L, about 0.08 nmol/L, about 0.09 nmol/L, about 0.1 nmol/L, about 0.125 nmol/L, about 0.15 nmol/L, about 0.175 nmol/L, about 0.2 nmol/L, about 0.3 nmol/L, about 0.4 nmol/L, or about 0.5 nmol/L, or less than 0.6 nmol/L e.g., before treatment with an insulin-Fc fusion protein described herein.

In some embodiments, the subject has been diagnosed with autoimmune diabetes (e.g., Type 1 diabetes) and has an endogenous C-peptide level of less than or equal to about 0.1 nmol/L, about 0.09 nmol/L, about 0.08 nmol/L, about 0.07 nmol/L, about 0.06 nmol/L, about 0.05 nmol/L, about 0.04 nmol/L, about 0.03 nmol/L, about 0.02 nmol/L, about 0.01 nmol/L, or less, e.g., before treatment with an insulin-Fc fusion protein described herein. In some embodiments, the subject has been diagnosed with autoimmune diabetes (e.g., Type 1 diabetes) and has an endogenous C-peptide level of less than or equal to about 0.01 nmol/L, about 0.009 nmol/L, about 0.008 nmol/L, about 0.007 nmol/L, about 0.006 nmol/L, about 0.005 nmol/L, about 0.004 nmol/L, about 0.003 nmol/L, about 0.002 nmol/L, about 0.001 nmol/L, or less, e.g., before treatment with an insulin-Fc fusion protein described herein. In some embodiments, the subject has been diagnosed with autoimmune diabetes (e.g., Type 1 diabetes) and has an endogenous C-peptide level of less than or equal to about 0.001 nmol/L, about 0.1 pmol/L, about 0.01 pmol/L, about 0.001 pmol/L, or less, e.g., before treatment with an insulin-Fc fusion protein described herein. In certain embodiments, the subject has been diagnosed with autoimmune diabetes (e.g., Type 1 diabetes) and has an undetectable level of endogenous C-peptide, e.g., before treatment with an insulin-Fc fusion protein described herein.

In some embodiments, the subject has been diagnosed with autoimmune diabetes (e.g., Type 1 diabetes) and has an endogenous C-peptide level of about 95% or less relative to a reference standard, e.g., before treatment with an insulin-Fc fusion protein described herein. In some embodiments, the subject has been diagnosed with autoimmune diabetes (e.g., Type 1 diabetes) and has an endogenous C-peptide level of about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, or about 1% or less relative to a reference standard.

In some embodiments, the endogenous C-peptide level may be measured in a subject in a fasting (e.g., deprived of glucose) or fed (e.g., stimulated with glucose) state. By way of example, a subject in a fasting state may abstain from food for about 30 minutes, about 1 hour, about 2 hours, about 4 hours, about 6 hours, about 8 hours, about 12 hours, about 18 hours, about 20 hours, or about 24 hours prior to analysis of the endogenous C-peptide level. In another example, a subject in a fed state may consume food within 12 hours, within 10 hours, within 6 hours, within 4 hours, within 3 hours, within 2 hours, within 1.5 hours, within 1 hour, within 30 minutes, within 15 minutes, or concurrent with analysis of the endogenous C-peptide level.

In some embodiments, the subject is in a fasted (e.g., deprived of glucose) state and has an undetectable level of endogenous C-peptide, e.g., prior to treatment with an insulin-Fc fusion protein described herein. In some embodiments, the subject is in a fasted (e.g., deprived of glucose) state and has an endogenous C-peptide level less than or equal to about 0.06 nmol/L, e.g., prior to treatment with an insulin-Fc fusion protein described herein. In some embodiments, the subject is in a fasted (e.g., deprived of glucose) state and has an endogenous C-peptide level less than or equal to about 0.06 nmol/L, about 0.07 nmol/L, about 0.08 nmol/L, about 0.09 nmol/L, about 0.1 nmol/L, about 0.125 nmol/L, about 0.15 nmol/L, about 0.175 nmol/L, about 0.2 nmol/L, about 0.3 nmol/L, about 0.4 nmol/L, about 0.5 nmol/L, about 0.6 nmol/L, about 0.7 nmol/L, about 0.8 nmol/L, about 0.9 nmol/L, about 1.0 nmol/L or more, e.g., prior to treatment with an insulin-Fc fusion protein described herein. In some embodiments, the subject is in a fasted state and has an endogenous C-peptide level of less than or equal to about 0.2 nmol/L, or less than or equal to about 0.5 nmol/L, or less than or equal to about 1.0 nmol/L, e.g., prior to treatment with an insulin-Fc fusion protein described herein.

In some embodiments, the subject is in a fed (e.g., stimulated with glucose) state and has an undetectable level of endogenous C-peptide, e.g., prior to treatment with an insulin-Fc fusion protein described herein. In some embodiments, the subject is in a fed (e.g., stimulated with glucose) state and has an endogenous C-peptide level less than or equal to about 0.2 nmol/L, e.g., prior to treatment with an insulin-Fc fusion protein described herein. In other embodiments, the subject is in a fed state (e.g., stimulated with glucose) state and has an endogenous C-peptide level less than or equal to about 0.2 nmol/L, about 0.25 nmol/L, about 0.3 nmol/L, about 0.4 nmol/L, about 0.5 nmol/L, about 0.6 nmol/L, about 0.7 nmol/L, about 0.8 nmol/L, about 0.9 nmol/L, about 1.0 nmol/L, or more, e.g., prior to treatment with an insulin-Fc fusion protein described herein. In certain embodiments, the subject is in a fed state and has an endogenous C-peptide level of less than or equal to about 0.6 nmol/L, or less than or equal to about 0.75 nmol/L, or less than or equal to about 1.0 nmol/L, e.g., prior to treatment with an insulin-Fc fusion protein described herein.

In some embodiments, the insulin-Fc fusion protein is administered prophylactically. In some embodiments, the subject has no detectable levels of an autoimmune antibody (e.g., an insulin autoantibody) and the insulin-Fc fusion protein is administered prophylactically. In some embodiments, the subject has no detectable levels of a pathogenic B cell population or a disease-causing B cell population (e.g., anti-insulin B cells, insulin-specific B cells, or insulin$^+$ B cells) and the insulin-Fc fusion protein is administered prophylactically. In some embodiments, the subject has no detectable levels of an autoimmune antibody (e.g., an insulin autoantibody) and no detectable levels of a pathogenic B cell population or a disease-causing B cell population (e.g., anti-insulin B cells, insulin-specific B cells, or insulin$^+$ B cells) and the insulin-Fc fusion protein is administered prophylactically. In some embodiments, the subject has not been diagnosed with an autoimmune disease (e.g., autoimmune diabetes, e.g., Type 1 diabetes). In some embodiments, the subject has not been diagnosed with an autoimmune disease (e.g., autoimmune diabetes, e.g., Type 1 diabetes) and the insulin-Fc fusion protein is administered prophylactically. In some embodiments, the subject is at risk for developing T1D, e.g., the subject has a first degree relative who has been diagnosed with T1D. The subject may be an adult or a child.

In some embodiments, the subject is at risk for developing T1D, e.g., the subject has one or more alleles at the DRB1, DQA1, and/or DQB1 loci (e.g., DR-DQ haplotypes) that are associated with higher risk for developing T1D, e.g., as described in Erlich, et al., Diabetes. 2008 April; 57(4): 1084-1092, incorporated herein by reference. In some embodiments, the subject has one or more of the following human leukocyte antigen (HLA) haplotypes:
  (a) DRB1*0301-DQA1*0501-DQB1*0201
  (b) DRB1*0405-DQA1*0301-DQB1*0302
  (c) DRB1*0401-DQA1*0301-DQB*0302
  (d) DRB1*0402-DQA1*0301-DQB1*0302
  (e) DRB1*0404-DQA1*0301-DQB1*0302; or
  (f) DRB1*0801-DQB1*0401-DQB1*0402.

In some embodiments, upon administration of the insulin-Fc fusion protein, the subject does not develop symptoms of an autoimmune disease (e.g., autoimmune diabetes, e.g., Type 1 diabetes). In some embodiments, upon administration of the insulin-Fc fusion protein, the subject does not develop symptoms of an autoimmune disease (e.g., autoimmune diabetes, e.g., Type 1 diabetes) for at least about 3 months, at least about 6 months, at least about 9 months, at least about 1 year, at least about 1.5 years, at least about 2 years, at least about 3 years, at least about 4 years, at least about 5 years, at least about 10 years, at least about 15 years, at least about 20 years, at least about 25 years, at least about 30 years, at least about 40 years, at least about 50 years or more.

In some embodiments, upon administration of the insulin-Fc fusion protein, the subject does not develop an autoimmune disease (e.g., autoimmune diabetes, e.g., Type 1 diabetes). In some embodiments, upon administration of the insulin-Fc fusion protein, the subject does not develop an autoimmune disease (e.g., autoimmune diabetes, e.g., Type 1 diabetes) for at least about 3 months, at least about 6 months, at least about 9 months, at least about 1 year, at least about 1.5 years, at least about 2 years, at least about 3 years, at least about 4 years, at least about 5 years, at least about 10 years, at least about 15 years, at least about 20 years, at least about 25 years, at least about 30 years, at least about 40 years, at least about 50 years or more.

In some embodiments, upon administration of the insulin-Fc fusion protein, the subject has a delayed rate of onset of the symptoms of autoimmune disease (e.g., autoimmune diabetes, e.g., Type 1 diabetes) compared with a reference standard or reference treatment. In some embodiments, upon administration of the insulin-Fc fusion protein, the rate of onset of autoimmune disease (e.g., autoimmune diabetes, e.g., Type 1 diabetes) is delayed by at least 3 months, at least 6 months, at least 9 months, at least 1 year, at least 1.5 years, at least 2 years, at least 3 years, at least 4 years, at least 5 years, at least 10 years, at least 15 years, at least 20 years, at least 25 years, at least 30 years, at least 40 years, at least 50 years or more, compared with a reference standard or reference treatment. In some embodiments, upon administration of the insulin-Fc fusion protein, the rate of onset of the symptoms of autoimmune disease (e.g., autoimmune diabetes, e.g., Type 1 diabetes) is delayed by about 2%, about 3%, about 4%, about 5%, about 7%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 99% or more compared with a reference standard or reference treatment.

In some embodiments, upon administration of the insulin-Fc fusion protein, the subject has a delayed rate of onset of autoimmune disease (e.g., autoimmune diabetes, e.g., Type 1 diabetes) compared with a reference standard or reference treatment. In some embodiments, upon administration of the insulin-Fc fusion protein, the rate of onset of autoimmune disease (e.g., autoimmune diabetes, e.g., Type 1 diabetes) is delayed by at least 3 months, at least 6 months, at least 9 months, at least 1 year, at least 1.5 years, at least 2 years, at least 3 years, at least 4 years, at least 5 years, at least 10 years, at least 15 years, at least 20 years, at least 25 years, at least 30 years, at least 40 years, at least 50 years or more, compared with a reference standard or reference treatment. In some embodiments, upon administration of the insulin-Fc fusion protein, the rate of onset of autoimmune disease (e.g., autoimmune diabetes, e.g., Type 1 diabetes) is delayed by about 2%, about 3%, about 4%, about 5%, about 7%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 99% or more compared with a reference standard or reference treatment.

In some embodiments, the insulin-Fc fusion protein is administered therapeutically. In some embodiments, the subject has detectable levels of an autoimmune antibody (e.g., an insulin autoantibody) and the insulin-Fc fusion protein is administered therapeutically. In some embodiments, the subject has detectable levels of a pathogenic B cell population or a disease-causing B cell population (e.g., anti-insulin B cells, insulin-specific B cells, or insulin⁺ B cells) and the insulin-Fc fusion protein is administered therapeutically. In some embodiments, the subject has detectable levels of an autoimmune antibody (e.g., an insulin autoantibody) and detectable levels of a pathogenic B cell population or a disease-causing B cell population (e.g., anti-insulin B cells, insulin-specific B cells, or insulin⁺ B cells) and the insulin-Fc fusion protein is administered therapeutically. In some embodiments, the subject has been diagnosed with an autoimmune disease (e.g., autoimmune diabetes, e.g., Type 1 diabetes). In some embodiments, the subject has been diagnosed with an autoimmune disease (e.g., autoimmune diabetes, e.g., Type 1 diabetes) and the insulin-Fc fusion protein is administered therapeutically.

In some embodiments, administration of the insulin-Fc fusion protein treats, reverses, or ameliorates the symptoms of autoimmune disease (e.g., autoimmune diabetes, e.g., Type 1 diabetes) in a subject compared to that observed in the subject prior to administration. In some embodiments, upon administration of the insulin-Fc fusion protein, the symptoms of autoimmune disease (e.g., autoimmune diabetes, e.g., Type 1 diabetes) in a subject are treated, reversed, or ameliorated by at least 3 months, at least 6 months, at least 9 months, at least 1 year, at least 1.5 years, at least 2 years, at least 3 years, at least 4 years, at least 5 years, at least 10 years, at least 15 years, at least 20 years, at least 25 years, at least 30 years, at least 40 years, at least 50 years or more, compared to that observed in the subject prior to administration. In certain embodiments, upon administration of the insulin-Fc fusion protein, the symptoms of autoimmune disease (e.g., autoimmune diabetes, e.g., Type 1 diabetes) in a subject are treated, reversed, or ameliorated by about 2%, about 3%, about 4%, about 5%, about 7%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 99% or more compared to that observed in the subject prior to administration.

In some embodiments, administration of the insulin-Fc fusion protein treats, reverses, or ameliorates an autoimmune disease (e.g., autoimmune diabetes, e.g., Type 1 diabetes) in a subject compared to that observed in the subject prior to administration. In some embodiments, upon administration of the insulin-Fc fusion protein, the autoimmune disease (e.g., autoimmune diabetes, e.g., Type 1 diabetes) in the subject is treated, reversed, or ameliorated by at least 3 months, at least 6 months, at least 9 months, at least 1 year, at least 1.5 years, at least 2 years, at least 3 years, at least 4 years, at least 5 years, at least 10 years, at least 15 years, at least 20 years, at least 25 years, at least 30 years, at least 40 years, at least 50 years or more, compared to that observed in the subject prior to administration. In certain embodiments, upon administration of the insulin-Fc fusion protein, the autoimmune disease (e.g., autoimmune diabetes, e.g., Type 1 diabetes) in the subject is treated, reversed, or ameliorated by about 2%, about 3%, about 4%, about 5%, about 7%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 99% or more compared to that observed in the subject prior to administration.

In some embodiments, the subject receives one course of treatment of an insulin-Fc fusion protein described herein. A course of treatment as used herein refers to a particular dosage amount or regimen as determined by a suitable practitioner provided to a subject until the autoimmune disease (e.g., autoimmune diabetes e.g., Type 1 diabetes) is treated, cured, alleviated, or the symptoms are reduced. In other embodiments, the subject receives more than one course of treatment of a fusion protein. In other embodiments, the subject receives a plurality of courses of treatment of a fusion protein. In still other embodiments, the subject receives a plurality of courses of treatment of a fusion protein, and each course of treatment is separated by a specific length of time (e.g., about 1 day, about 1 week, about 2 weeks, about 1 month, about 2 months, about 3 months, about 6 months, about 1 year, about 1.5 years, about 2 years, about 3 years, about 4 years, about 5 years, about 7.5 years, about 10 years, about 12.5 years, about 15 years, about 20 years or more).

In some embodiments, the subject is an adult (e.g., at least 18 years of age, e.g., at least 19, 20, 21, 22, 23, 24, 25, 25-30, 30-35, 35-40, 40-50, 50-60, 60-70, 70-80, or 80-90 years of age). In some embodiments, the subject is a child (e.g., less than 18 years of age, e.g., less than 17, 16, 15, 14, 13, 12, 11, 10, 9, 8, 7, 6, 5, 4, 3, 2, 1 or less years of age). In some embodiments, the subject is a male or a female.

In some embodiments, a reference treatment used in any method described herein includes but is not limited to an insulin or insulin analog, e.g., an insulin or insulin analog described herein; islet cell transplantation; pancreas transplantation; or antibody (e.g., cytotoxic antibody) against a pan-B cell antigen (e.g., anti-CD20 antibody, anti-CD22 antibody, or anti-CD19 antibody). In some embodiments, a reference treatment can include a naturally occurring insulin (e.g., proinsulin or mature insulin) from a mammal, e.g., human or mouse or compositions described in US 2013/0028918 A1 or CN 103509118A.

In some embodiments, a reference standard used in any method described herein includes an outcome, e.g., outcome described herein, of an autoimmune disease therapy, e.g., type 1 diabetes therapy. In some embodiments, a reference standard is a level of a marker (e.g., blood glucose or level of C peptide) in the subject prior to initiation of a therapy, e.g., an insulin-Fc fusion protein therapy described herein, e.g., where the subject is at risk for developing T1D (e.g., subject is a first degree relative of a T1D patient); where the subject is pre-diabetic (e.g., subject is autoantibody positive); where the subject has experienced a recent onset of T1D (e.g., time from onset of less than 12 months); where the subject has long-standing T1D (e.g., time from onset greater than or equal to 12 months); or where the subject is a healthy subject (e.g., healthy age and/or sex-matched subject). In some embodiments, a reference standard is a measure of presence of/progression of/severity of disease or presence of/severity of symptoms of disease prior to initiation of a therapy, e.g., an insulin-Fc fusion protein therapy described herein, e.g., where the subject is at risk for developing T1D (e.g., subject is a first degree relative of a T1D patient); where the subject is pre-diabetic (e.g., subject is autoantibody positive); where the subject has experienced a recent onset of T1D (e.g., time from onset of less than 12 months); where the subject has long-standing T1D (e.g., time from onset greater than or equal to 12 months); or where the subject is a healthy subject (e.g., healthy age and/or sex-matched subject).

Pharmaceutical Compositions

Provided herein are pharmaceutical compositions containing a fusion protein described herein that can be used to treat or prevent an autoimmune disease, e.g., autoimmune diabetes, e.g., Type 1 diabetes.

The amount and concentration of the fusion protein in pharmaceutical compositions, as well as the quantity of the pharmaceutical composition administered to a subject, can be selected based on clinically relevant factors, such as medically relevant characteristics of the subject (e.g., age, weight, gender, other medical conditions, and the like), the solubility of compounds in the pharmaceutical compositions, the potency and activity of the compounds, and the manner of administration of the pharmaceutical compositions. For further information on Routes of Administration and Dosage Regimes, see Chapter 25.3 in Volume 5 of Comprehensive Medicinal Chemistry (Corwin Hansch; Chairman of Editorial Board), Pergamon Press 1990.

Provided herein are pharmaceutical compositions containing an insulin-Fc fusion protein described herein that can be used to treat or prevent an autoimmune disease, e.g., autoimmune diabetes, e.g., Type 1 diabetes.

While it is possible for an insulin-Fc fusion protein described herein to be administered alone, in some embodiments, the insulin-Fc fusion protein of the present technology may be administered as a pharmaceutical formulation (composition), where the insulin-Fc fusion protein is combined with one or more pharmaceutically acceptable diluents, excipients or carriers. The pharmaceutical compositions having one or more insulin-Fc fusion proteins disclosed herein can include a carrier, which can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thiomerasol, and the like. Glutathione and other antioxidants can be included to prevent oxidation. In many cases, it will be advantageous to include isotonic agents, for example, sugars, polyalcohols such as mannitol, sorbitol, or sodium chloride in the composition. Prolonged absorption of the injectable compositions can be brought about by including in the composition an agent that delays absorption, for example, aluminum monostearate or gelatin.

The insulin-Fc fusion protein may be formulated for administration in any convenient way for use in human medicine. In certain embodiments, the insulin-Fc fusion protein included in the pharmaceutical preparation may be active itself, or may be a prodrug, e.g., capable of being converted to an active compound in a physiological setting. Regardless of the route of administration selected, the insulin-Fc fusion protein of the present technology, which may be used in a suitable hydrated form, and/or the pharmaceutical compositions of the present technology, is formulated into a pharmaceutically acceptable dosage form described herein or by other conventional methods known to those of skill in the art.

In another aspect, the present technology provides pharmaceutically acceptable compositions comprising a therapeutically effective amount or prophylactically effective amount of an insulin-Fc fusion protein described herein, formulated together with one or more pharmaceutically acceptable carriers (additives) and/or diluents. The pharmaceutical compositions described herein can be specially formulated for administration in solid or liquid form, including those adapted for parenteral administration, for example, by subcutaneous, intramuscular or intravenous injection as, for example, a sterile solution or suspension. In certain embodiments, the pharmaceutical compositions can be simply dissolved or suspended in sterile water. In some embodiments, the pharmaceutical preparation is non-pyrogenic, i.e., does not elevate the body temperature of a patient.

Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) cyclodextrins such as Captisol®; and (22) other non-toxic compatible substances employed in pharmaceutical formulations. In some embodiments, the carrier includes phosphate buffered saline (PBS).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

As described herein, certain embodiments of the insulin-Fc fusion proteins of the present technology can contain a basic functional group, such as an amine, and are thus capable of forming pharmaceutically acceptable salts with pharmaceutically acceptable acids. The term "pharmaceutically acceptable salts" in these instances, refers to the relatively non-toxic, inorganic and organic acid addition salts of the insulin-Fc fusion proteins of the present technology. These salts can be prepared in situ during the final isolation and purification of the insulin-Fc fusion protein, or by separately reacting a purified insulin-Fc fusion protein described herein in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (see, for example, Berge et al. (1977) "Pharmaceutical Salts", J. Pharm. Sci. 66:1-19).

In other cases, certain embodiments of the insulin-Fc fusion proteins of the present technology can contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of the insulin-Fc fusion protein. These salts can likewise be prepared in situ during the final isolation and purification of the insulin-Fc fusion protein, or by separately reacting the purified insulin-Fc fusion protein in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Pharmaceutical compositions are typically formulated to be compatible with its intended route of administration. Examples of routes of administration include parenteral (e.g., intravenous, intradermal, intraperitoneal or subcutaneous), oral, inhalation, transdermal (topical), intraocular, iontophoretic, and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. For convenience of the patient or treating physician, the dosing formulation can be provided in a kit containing all necessary equipment (e.g., vials of drug, vials of diluent, syringes and needles) for a treatment course (e.g., 7 days of treatment).

Formulations of the present disclosure include those suitable for parenteral administration. The formulations may conveniently be presented in unit dosage form and may be prepared by any methods well known in the art of pharmacy. The amount of active ingredient which can be combined with a carrier material to produce a single dosage form will vary depending upon the subject being treated and the particular mode of administration. The amount of active ingredient that can be combined with a carrier material to produce a single dosage form will generally be that amount of the compound which produces a therapeutic effect. Generally, out of one hundred percent, this amount will range from about 1 percent to about 99 percent of active ingredient, from about 5 percent to about 70 percent, or from about 10 percent to about 30 percent.

Pharmaceutical compositions of the present technology suitable for parenteral administration comprise insulin-Fc fusion proteins described herein in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the present technology include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants, e.g., Tween-like surfactants. In some embodiments, the pharmaceutical composition (e.g., as described herein) comprises a Tween-like surfactant, e.g., Tween-80. In some embodiments, the pharmaceutical composition (e.g., as described herein) comprises a Tween-like surfactant, e.g., Tween-80, at a concentration between about 0.001% and about 2%, or between about 0.005% and about 0.1%, or between about 0.01% and about 0.5%.

In some embodiments, in order to prolong the effect of the insulin-Fc fusion protein, it may be desirable to slow the absorption of the drug from the subcutaneous or intramuscular injection site. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered form of the insulin-Fc fusion protein is accomplished by dissolving or suspending the insulin-Fc fusion protein in an oil vehicle. Alternatively, absorption of the drug may be delayed through the use of a concentrated form of the insulin-Fc fusion protein.

In some embodiments, the insulin-Fc fusion protein is administered as a bolus infusion or an intravenous push. In some embodiments, the insulin-Fc fusion protein is administered through syringe injection, pump, pen, needle, or indwelling catheter.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (BASF, Parsippany, N.J.) or phosphate buffered saline (PBS). In all cases, a composition for parenteral administration must be sterile and should be fluid to the extent that easy syringability exists. It should be stable under the conditions of manufacture and storage and must be preserved against the contaminating action of microorganisms such as bacteria and fungi.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, typical methods of preparation include vacuum drying and freeze drying, which can yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressurized container or dispenser, which contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal/topical means. For transmucosal or transdermal/topical administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or inhalants. For transdermal/topical administration, the active compounds are formulated into powders, solutions, ointments, lotions, gels, patches, pastes, salves, or creams as generally known in the art. The active compound can be mixed under sterile conditions with a pharmaceutically acceptable carrier, and with any preservatives, buffers, or propellants that may be required. In one embodiment, transdermal administration may be performed by iontophoresis.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

The present technology contemplates formulation of the insulin-Fc fusion protein in any of the aforementioned pharmaceutical compositions and preparations. Furthermore, the present technology contemplates administration via any of the foregoing routes of administration. One of skill in the art can select the appropriate formulation and route of administration based on the condition being treated and the overall health, age, and size of the patient being treated.

Effective Dosages

Dosage, toxicity and therapeutic efficacy of any therapeutic agent can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are advantageous. While compounds that exhibit toxic side effects may be used, care should be taken to design a delivery system that targets such compounds to the site of affected tissue in order to minimize potential damage to unaffected cells and, thereby, reduce side effects.

The data obtained from the cell culture assays and animal studies can be used in formulating a range of dosage for use in humans. The dosage of such compounds may be within a range of circulating concentrations that include the ED50 with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the $IC_{50}$ as determined in cell culture. Such information can be used to determine useful doses in humans accurately. Levels in plasma may be measured, for example, by high performance liquid chromatography.

Actual dosage levels of the insulin-Fc fusion protein in the pharmaceutical compositions described herein can be varied so as to obtain an amount of the active ingredient that is effective to achieve the desired therapeutic or prophylactic response for a particular patient, composition, and mode of administration, without being toxic to the patient.

The selected dosage level will depend upon a variety of factors including the activity of the particular insulin-Fc fusion protein employed, or the ester, salt or amide thereof, the route of administration, the time of administration, the rate of excretion of the particular insulin-Fc fusion protein being employed, the duration of the treatment, other drugs, compounds and/or materials used in combination with the particular insulin-Fc fusion protein employed, the severity of the disease or disorder, previous treatments, the age, sex, weight, condition, general health and prior medical history of the patient being treated, and like factors well known in the medical arts. Moreover, treatment of a subject with a therapeutically or prophylactically effective amount of the pharmaceutical compositions described herein can include a single treatment or a series of treatments.

A physician having ordinary skill in the art can readily determine and prescribe the effective amount of the pharmaceutical composition required. For example, the physician could start doses of the insulin-Fc fusion protein employed in the pharmaceutical composition at levels lower than that required in order to achieve the desired therapeutic or prophylactic effect and gradually increase the dosage until the desired effect is achieved. When the insulin-Fc fusion protein is administered as a pharmaceutical, to a subject, it can be given per se or as a pharmaceutical composition containing, for example, 0.1 to 99.5% (or 0.5 to 90%) of active ingredient in combination with a pharmaceutically acceptable carrier.

In general, a suitable daily dose of an insulin-Fc fusion protein will be that amount of the insulin-Fc fusion protein that is the lowest dose effective to produce a therapeutic effect. Such an effective dose will generally depend upon the factors described above. Typically, an effective amount of the one or more insulin-Fc fusion proteins disclosed herein sufficient for achieving a therapeutic or prophylactic effect, range from about 0.000001 mg per kilogram body weight per day to about 10,000 mg per kilogram body weight per day. Suitably, the dosage ranges are from about 0.0001 mg per kilogram body weight per day to about 100 mg per kilogram body weight per day. For example dosages can be 1 mg/kg body weight or 10 mg/kg body weight every day, every two days or every three days or within the range of 1-10 mg/kg every week, every two weeks or every three weeks. In one embodiment, a single dosage of the therapeutic compound ranges from 0.001-10,000 micrograms per kg body weight. In one embodiment, one or more insulin-Fc fusion protein concentrations in a carrier range from 0.2 to 2000 micrograms per delivered milliliter. An exemplary treatment regime entails administration once per day or once a week. In therapeutic applications, a relatively high dosage at relatively short intervals is sometimes required until progression of the disease is reduced or terminated, or until the subject shows partial or complete amelioration of symptoms of disease. Thereafter, the patient can be administered a prophylactic regime. In some embodiments, a therapeutically effective amount of one or more insulin-Fc fusion proteins may be defined as a concentration of insulin-Fc fusion protein at the target tissue of $10^{-32}$ to $10^{-6}$ molar, e.g., approximately $10^{-7}$ molar. This concentration may be delivered by systemic doses of 0.001 to 100 mg/kg or equivalent dose by body surface area. The schedule of doses would be optimized to maintain the therapeutic concentration at the target tissue, such as by single daily or weekly administration, but also including continuous administration (e.g., parenteral infusion or transdermal application).

Generally, intravenous and subcutaneous doses of the insulin-Fc fusion protein for a patient will range from about 0.0001 to about 100 mg per kilogram of body weight per day, e.g., about 0.0001-about 0.001 mg/kg/day, about 0.001-about 0.01 mg/kg/day, about 0.01-about 0.1 mg/kg/day, about 0.1-about 1 mg/kg/day, about 1-about 10 mg/kg/day, or about 10-about 100 mg/kg/day. In some embodiments, the insulin-Fc fusion protein is administered at a dose greater than or equal to 60 nmol/kg/day. In some embodiments, the insulin-Fc fusion protein is administered at a dose greater than or equal to 75 nmol/kg/day, greater than or equal to 100 nmol/kg/day, greater than or equal to 150 nmol/kg/day, or greater than or equal to 200 nmol/kg/day. In certain embodiments, the insulin-Fc fusion protein is administered at a dose greater than or equal to 1 mg/kg/day, e.g., 2 mg/kg/day, 4 mg/kg/day, 8 mg/kg/day, 16 mg/kg/day, 32 mg/kg/day, 64 mg/kg/day, 100 mg/kg/day, 200 mg/kg/day or greater.

The insulin-Fc fusion protein may be present at a concentration of about 100 mg/mL or less (e.g., 100 mg/mL or less, e.g., 90 mg/mL, 80 mg/mL, 70 mg/mL, 60 mg/mL, 50 mg/mL, 40 mg/mL, 30 mg/mL, 20 mg/mL, 10 mg/mL, 5 mg/mL, 2.5 mg/mL, 1 mg/mL, 0.5 mg/mL, 0.25 mg/mL, 0.1 mg/mL, 0.05 mg/mL, 0.01 mg/mL, or less). In some embodiments, the insulin-Fc fusion protein is present at a concentration of about 0.25 mg/mL to about 1 mg/mL, e.g., about 0.25 mg/mL, about 0.5 mg/mL (e.g., 0.5 mg/mL), about 0.75 mg/mL, or about 1 mg/mL.

If desired, the effective daily dose of the insulin-Fc fusion protein can be administered as two, three, four, five, six or more sub-doses administered separately at appropriate intervals throughout the day, optionally, in unit dosage forms. In some embodiments, the insulin-Fc fusion protein is administered once daily. In some embodiments, the insulin-Fc fusion protein is administered at least twice a week. In some embodiments, the insulin-Fc fusion protein is administered at least once a week. In certain embodiments, the insulin-Fc fusion protein is administered twice weekly.

The insulin-Fc fusion protein can be administered as such or in admixtures with pharmaceutically acceptable and/or sterile carriers and can also be administered in conjunction with antimicrobial agents such as penicillins, cephalosporins, aminoglycosides and glycopeptides. Conjunctive therapy thus includes sequential, simultaneous and separate administration of the insulin-Fc fusion protein in a way that the therapeutic or prophylactic effects of the first administered therapy are still detectable when the subsequent therapy is administered.

Combination Therapy

In some embodiments, one or more insulin-Fc fusion proteins disclosed herein may be combined with one or more additional therapies for the prevention or treatment of an autoimmune disease (e.g., autoimmune diabetes, e.g., Type 1 diabetes).

In any case, the multiple therapeutic agents may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to no more than four weeks. In addition, the combination methods, compositions and formulations are not to be limited to the use of only two agents.

In some embodiments, the at least one additional therapy is administered in a formulation comprising a combination with an insulin-Fc fusion protein described herein to treat or prevent an autoimmune disease (e.g., autoimmune diabetes, e.g., Type 1 diabetes). In certain embodiments, the at least one additional therapy is administered simultaneously with the insulin-Fc fusion protein described herein. In certain embodiments, the at least one additional therapy is administered sequentially (at a different time) than the insulin-Fc fusion protein described herein. In an example, the at least one additional therapy is administered about 5 minutes, about 10 minutes, about 30 minutes, about 1 hour, about 1.5 hours, about 2 hours, about 4 hours, about 6 hours, about 12 hours, about 18 hours, about 24 hours, about 2 days, about 3 days, about 4 days, about 5 days, about 6 days, about 1 week, about 2 weeks, about 3 weeks, about 4 weeks apart from the insulin-Fc fusion protein described herein. The at least one additional therapy may or may not be administered by the same route as the insulin-Fc fusion protein. In an example, the insulin-Fc fusion protein may be administered in one manner (e.g., intravenously or subcutaneously), while the at least one additional therapy may be separately administered in another manner (e.g., orally).

In some embodiments, the at least one additional therapy is an insulin sensitizer. Insulin sensitizers (e.g., biguanides (e.g., metformin) and glitazones (e.g., rosiglitazone and pioglitazone)) act by increasing the response of a subject to a given amount of insulin (or insulin analog). A patient receiving an insulin sensitizer may therefore require a lower dose of an insulin-Fc fusion protein described herein compared with a patient not receiving said insulin sensitizer. Thus, in certain embodiments, the insulin-Fc fusion protein is administered to a subject in combination with an insulin sensitizer. In some embodiments, the insulin-Fc fusion protein may be administered at about 95% of the standard dose required in the absence of the insulin sensitizer, e.g., at about 90%, at about 85%, about 80%, at about 75%, at about 70%, at about 65%, at about 60%, at about 55%, at about 50%, at about 50%, at about 45%, at about 40%, at about 35%, at about 30%, at about 25%, at about 20%, at about 15%, at about 10%, at about 5% or less of the standard dose required in the absence of the insulin sensitizer.

In some embodiments, the at least one additional therapy is administered to prevent full onset of an autoimmune disease (e.g., autoimmune diabetes, e.g., Type 1 diabetes) or the symptoms thereof and results in maintenance of at least about 90% β-cell mass compared with that of a healthy subject. In some embodiments, the at least one additional therapy is administered to prevent full onset of an autoimmune disease (e.g., autoimmune diabetes, e.g., Type 1 diabetes) and results in maintenance of at least about 80%, at least about 70%, at least about 60%, at least about 50%, at least about 40%, at least about 30%, at least about 20%, at least about 10%, or at least about 5% β-cell mass compared with that of a healthy subject. In some embodiments, the insulin-Fc fusion protein is administered to a subject in combination with a therapy that prevents the symptoms of an autoimmune disease (e.g., autoimmune diabetes, e.g., Type 1 diabetes) and results in maintenance of at least about 90% β-cell mass compared with that of a healthy subject. In some embodiments, the insulin-Fc fusion protein is administered to a subject in combination with a therapy that prevents the symptoms of an autoimmune disease (e.g., autoimmune diabetes, e.g., Type 1 diabetes) and results in maintenance of at least about 80%, at least about 70%, at least about 60%, at least about 50%, at least about 40%, at least about 30%, at least about 20%, at least about 10%, or at least about 5% β-cell mass compared with that of a healthy subject.

In some embodiments, the at least one additional therapy is administered to prevent full onset of an autoimmune disease (e.g., autoimmune diabetes, e.g., Type 1 diabetes) or the symptoms thereof and results in maintenance of at least about 90% endogenous C-peptide level compared with that of a healthy subject. In some embodiments, the at least one additional therapy is administered to prevent full onset of an autoimmune disease (e.g., autoimmune diabetes, e.g., Type 1 diabetes) or the symptoms thereof and results in maintenance of at least about 80%, at least about 70%, at least about 60%, at least about 50%, at least about 40%, at least about 30%, at least about 20%, at least about 10%, or at least about 5% endogenous C-peptide level compared with that of a healthy subject. In some embodiments, the insulin-Fc fusion protein is administered to a subject in combination with a therapy that prevents the symptoms of an autoimmune disease (e.g., autoimmune diabetes, e.g., Type 1 diabetes) and results in maintenance of at least about 90% endogenous C-peptide level compared with that of a healthy subject. In some embodiments, the insulin-Fc fusion protein is administered to a subject in combination with a therapy that prevents the symptoms of an autoimmune disease (e.g., autoimmune diabetes, e.g., Type 1 diabetes) and results in maintenance of at least at least about 80%, at least about 70%, at least about 60%, at least about 50%, at least about 40%, at least about 30%, at least about 20%, at least about 10%, or at least about 5% endogenous C-peptide level compared with that of a healthy subject.

Kits

The present disclosure also provides kits for the prevention and/or treatment of an autoimmune disease (e.g., autoimmune diabetes, e.g., Type 1 diabetes) comprising one or more of the insulin-Fc fusion proteins described herein. Optionally, the above described components of the kits of the present technology are packed in suitable containers and labeled for the prevention and/or treatment of an autoimmune disease (e.g., autoimmune diabetes, e.g., Type 1 diabetes).

The above-mentioned components may be stored in unit or multi-dose containers, for example, sealed ampoules, vials, bottles, syringes, and test tubes, as an aqueous, preferably sterile, solution or as a lyophilized, preferably sterile, formulation for reconstitution. The kit may further comprise a second container which holds a diluent suitable for diluting the pharmaceutical composition towards a higher volume. Suitable diluents include, but are not limited to, the pharmaceutically acceptable excipient of the pharmaceutical composition and a saline solution. Furthermore, the kit may comprise instructions for diluting the pharmaceutical composition and/or instructions for administering the pharmaceutical composition, whether diluted or not. The containers may be formed from a variety of materials such as glass or plastic and may have a sterile access port (for example, the container may be an intravenous solution bag or a vial having a stopper which may be pierced by a hypodermic injection needle). The kit may further comprise more containers comprising a pharmaceutically acceptable buffer, such as phosphate-buffered saline, Ringer's solution and dextrose solution. It may further include other materials desirable from a commercial and user standpoint, including other buffers, diluents, filters, needles, syringes, culture medium for one or more of the suitable hosts. The kits may optionally include instructions customarily included in commercial packages of therapeutic products, that contain information about, for example, the indications, usage, dosage, manufacture, administration, contraindications and/or warnings concerning the use of such therapeutic or products.

The kit can also comprise, e.g., a buffering agent, a preservative or a stabilizing agent. The kit can also contain a control sample or a series of control samples, which can be assayed and compared to the test sample. Each component of the kit can be enclosed within an individual container and all of the various containers can be within a single package, along with instructions for interpreting the results of the assays performed using the kit. The kits of the present technology may contain a written product on or in the kit container. The written product describes how to use the reagents contained in the kit. In certain embodiments, the use of the reagents can be according to the methods of the present technology.

EXAMPLES

The present technology is further illustrated by the following Examples, which should not be construed as limiting in any way.

Example 1: Synthesis and Methods of Making an Insulin-Fc Fusion Protein in HEK293 Cells Insulin-Fc fusion proteins were synthesized as follows. A gene sequence of interest was constructed using proprietary software (LakePharma, Belmont, Calif.) and were cloned into a high expression mammalian vector. HEK293 cells were seeded in a shake flask 24 hours before transfection, and were grown using serum-free chemically defined media. A DNA expression construct that encodes the insulin-Fc fusion protein of interest was transiently transfected into a 2 L suspension of HEK293 cells using the Syd Labs (Natick, Mass.) standard operating procedure for transient transfection. After 20 hours, cells were counted to determine the viability and viable cell count, and titer was measured by ForteBio® Octet® (Pall ForteBio LLC, Fremont, Calif.). Additional readings were taken throughout the transient transfection production run. The culture was harvested on or after day 5.

As shown in Table 1, exemplary insulin-Fc fusion proteins of the present technology (SEQ ID NO: 2; SEQ ID NO: 3; SEQ ID NO: 4; SEQ ID NO: 5; SEQ ID NO: 6; SEQ ID NO: 7; and SEQ ID NO: 8) that were synthesized in HEK293 cells exhibited a significantly higher titer than other insulin-Fc fusion proteins that do not contain the 'AAK' C-chain sequence (SEQ ID NO: 9 and SEQ ID NO: 10).

TABLE 1

Titer (mg/L) for Insulin-Fc Fusion Proteins Manufactured in HEK293 Cells

| Sequence | Titer (mg/L) | % of Maximum Titer |
| --- | --- | --- |
| SEQ ID NO: 2 | 139 | 100% |
| SEQ ID NO: 3 | 93 | 67% |
| SEQ ID NO: 4 | 117 | 84% |
| SEQ ID NO: 5 | 93 | 67% |
| SEQ ID NO: 6 | 88 | 63% |
| SEQ ID NO: 7 | 83 | 60% |
| SEQ ID NO: 8 | 138 | 99% |
| SEQ ID NO: 9 | 29 | 21% |
| SEQ ID NO: 10 | 33 | 24% |

Example 2: Synthesis and Methods of Making an Insulin-Fc Fusion Protein in CHO Cells A CHO cell line was originally derived from CHO-K1 (LakePharma, Belmont, Calif.), and the endogenous glutamine synthetase (GS) genes were knocked out by recombinant technology using methods known in the art. Stable expression DNA vectors were designed and optimized for CHO expression and GS selection and incorporated into a high expression mammalian vector (LakePharma, Belmont, Calif.). The sequence of each completed construct was confirmed prior to initiating scale up experiments. The suspension CHO cells were cultured in a humidified 5% $CO_2$ incubator at 37° C. in a chemically defined media (CD OptiCHO™; Invitrogen, Carlsbad, Calif.). No serum or other animal-derived products were used in culturing the CHO cells.

Approximately 80 million suspension-adapted CHO cells, growing in CD OptiCHO™ media during the exponential growth phase, were transfected by electroporation using MaxCyte® STX® system (MaxCyte, Inc., Gaithersburg, Md.) with 80 μg DNA to a create a stable CHO cell line for each insulin-Fc fusion protein (DNA construct contains the full-length sequence of the insulin-Fc fusion protein). After twenty-four hours, the transfected cells were counted and placed under selection for stable integration of the insulin-Fc fusion genes. The transfected cells were seeded into CD OptiCHO™ selection media containing 100 μM methionine sulfoximine (MSX) at a cell density of $0.5 \times 10^6$ cells/mL in a shaker flask and incubated at 37° C. with 5% $CO_2$. During a selection process, the cells were spun down and resuspended in fresh selection media every 2-3 days until the pool recovered its growth rate and viability. The cell culture was monitored for growth and titer.

The cells were grown to $2.5 \times 10^6$ cells per mL. At the time of harvest for cell banking, the viability was above 95%. The cells were then centrifuged, and the cell pellet was resuspended in the CD OptiCHO™ media with 7.5% dimethyl sulfoxide (DMSO) to a cell count of $15 \times 10^6$ cells per mL per vial. Vials were cryopreserved for storage in liquid nitrogen.

A small-scale-up production was performed using the CHO cells as follows. The cells were scaled up for production in CD OptiCHO™ growth medium containing 100 μM MSX at 37° C. and fed every 2-4 days as needed, with CD OptiCHO™ growth medium supplemented with glucose and additional amino acids as necessary for approximately 14-21 days. The conditioned media supernatant harvested from the stable pool production run was clarified by centrifuge spinning. The protein was run over a Protein A (MabSelect, GE Healthcare, Little Chalfont, United Kingdom) column and eluted using a pH gradient. Filtration using a 0.2 μM membrane filter was performed.

The cell line was optionally further subcloned to monoclonality and optionally further selected for high titer insulin-Fc-fusion protein-expressing clones using the method of limiting dilution, a method known to those skilled in the art. After obtaining a high titer, monoclonal insulin-Fc fusion protein-expressing cell line, production of the insulin-Fc fusion protein was accomplished as described above in growth medium without MSX, or optionally in growth medium containing MSX, to obtain a cell culture supernatant that containing the recombinant, CHO-made, insulin-Fc fusion protein.

Example 3: Purification of an Insulin-Fc Fusion Protein

Figure 2:
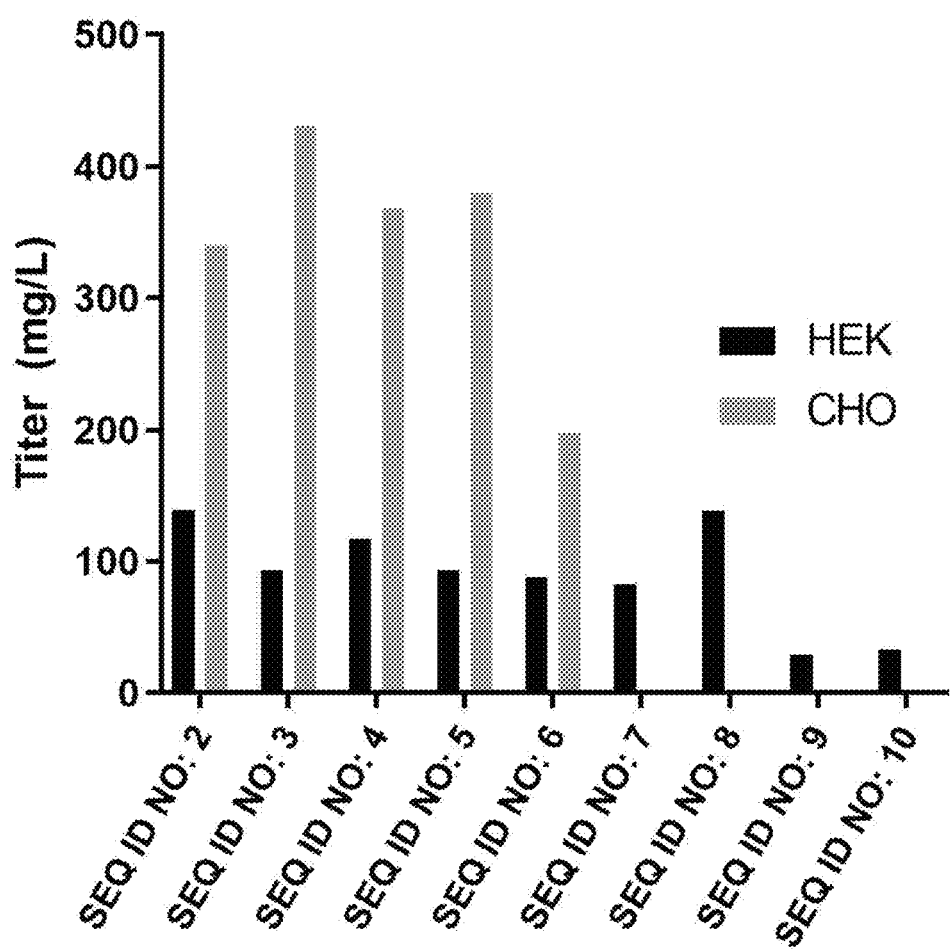
FIG. 2 shows a graph depicting the titer concentrations for the insulin-Fc fusion proteins of the present technology, manufactured in HEK cells and in CHO cells. The titers shown are titers observed after the Protein A purification step.

Purification of an insulin-Fc fusion protein was performed as follows. Conditioned media supernatants containing the secreted insulin-Fc fusion protein were harvested from the transiently or stably transfected HEK or CHO production runs and were clarified by centrifugation. The supernatant containing the desired insulin-Fc fusion protein was run over a Protein A column and eluted using a low pH gradient. Afterwards, the eluted desired protein fractions were pooled and buffer exchanged into 200 mM HEPES, 100 mM NaCl, 50 mM NaOAc, pH 7.0 buffer. A final filtration step was performed using a 0.2 μm membrane filter. The final protein concentration was calculated from the solution optical density at 280 nm. Further optional purification by ion-exchange chromatography, gel filtration chromatography, or other methods was performed as necessary. The titer results (mg/L) obtained after Protein A column purification are displayed in FIG. 2.

Example 4: Structure Confirmation by Non-Reducing and Reducing CE-SDS

CE-SDS analysis was performed in a LabChip® GXII (Perkin Elmer, Waltham, Mass.) on a solution of a purified insulin-Fc fusion protein dissolved in 200 mM HEPES, 100 mM NaCl, 50 mM NaOAc, pH 7.0 buffer, and the electropherogram was plotted. Under non-reducing conditions, the sample was run against known molecular weight (MW) protein standards, and the eluting peak represented the 'apparent' MW of the insulin-Fc fusion protein homodimer.

Under reducing conditions (using beta-mercaptoethanol to break disulfide bonds of the insulin-Fc fusion protein homodimer), the apparent MW of the resulting insulin-Fc fusion protein monomer is compared against half the molecular weight of the insulin-Fc fusion protein homodimer as a way of determining that the structural purity of the insulin-Fc fusion protein is likely to be correct.

The non-reducing and reducing main peak found via CE-SDS analysis for insulin-Fc fusion proteins synthesized in HEK293 cells are shown in Table 2. The non-reducing and reducing main peak found via CE-SDS analysis for insulin-Fc fusion proteins synthesized in CHO cells are shown in Table 3, and 2× the apparent MW of the resulting insulin-Fc fusion protein monomer was compared the molecular weight of the insulin-Fc fusion protein homodimer. The results in Table 2 and Table 3 illustrate that the structural purities of the insulin-Fc fusion proteins are likely to be correct.

TABLE 2

CE-SDS Non-Reducing and Reducing Main Peak for insulin-Fc fusion proteins synthesized in HEK293 cells

| Sequence | Non-reducing (kDa) Peak 1 | Reducing (kDa) Peak 1 | $\dfrac{MW_{homodimer}}{2 \times MW_{monomer}}$ |
|---|---|---|---|
| SEQ ID NO: 2 | 94.0 | 46.1 | 1.0 |
| SEQ ID NO: 3 | 87.7 | 42.3 | 1.1 |
| SEQ ID NO: 4 | 87.1 | 42.8 | 1.0 |
| SEQ ID NO: 5 | 93.7 | 44.0 | 1.1 |
| SEQ ID NO: 6 | 95.5 | 44.0 | 1.1 |
| SEQ ID NO: 7 | 95.6 | 43.4 | 1.1 |
| SEQ ID NO: 8 | 97.3 | 43.3 | 1.1 |
| SEQ ID NO: 9 | 88.0 | 44.5 | 1.0 |
| SEQ ID NO: 10 | 89.1 | 46.3 | 1.0 |

TABLE 3

CE-SDS Non-Reducing and Reducing Main Peak for insulin-Fc fusion proteins synthesized in CHO cells

| Sequence | Non-reducing (kDa) Peak 1 | Reducing (kDa) Peak 1 | $\dfrac{\text{non-reducing}}{2 \times \text{reducing}}$ |
|---|---|---|---|
| SEQ ID NO: 2 | 78.8 | 40.4 | 1.0 |
| SEQ ID NO: 3 | 83.9 | 42.8 | 1.0 |
| SEQ ID NO: 4 | 88.3 | 43.0 | 1.1 |
| SEQ ID NO: 5 | 84.7 | 42.4 | 1.0 |
| SEQ ID NO: 6 | 86.1 | 41.4 | 1.1 |
| SEQ ID NO: 7 | DNS | DNS | DNS |
| SEQ ID NO: 8 | DNS | DNS | DNS |
| SEQ ID NO: 9 | DNS | DNS | DNS |
| SEQ ID NO: 10 | DNS | DNS | DNS |

*DNS = did not synthesize

Example 5: Sequence Identity by LC-MS with Glycan Removal

To obtain an accurate estimate of the insulin-Fc mass via mass spectroscopy (MS), the sample was first treated to remove naturally occurring glycan that might interfere with the MS analysis. 100 µL of a 2.5 mg/mL insulin-Fc fusion protein dissolved in 200 mM HEPES, 100 mM NaCl, 50 mM NaOAc, pH 7.0 buffer solution was first buffer exchanged into 0.1 M Tris, pH 8.0 buffer containing 5 mM EDTA using a Zeba desalting column (Pierce, ThermoFisher Scientific, Waltham, Mass.). 1.67 µL of PNGase F enzyme (Prozyme N-glycanase) was added to this solution in order to remove N-linked glycan present in the fusion protein, and the mixture was incubated at 37° C. overnight in an incubator. The sample was then analyzed via LC-MS (NovaBioassays, Woburn, Mass.) resulting in a molecular mass of the molecule which corresponds to the desired homodimer without the glycan. This mass was then further corrected since the enzymatic process used to cleave glycan from asparagine, also deaminates the asparagine side chain to form an aspartic acid, and in doing so the enzymatically treated homodimer gains 2 Da overall, corresponding to a mass of 1 Da for each chain present in the homodimer. Therefore the actual molecular mass is the measured mass minus 2 Da to correct for the enzymatic modification of the insulin-Fc fusion protein structure in the analytical sample. The LC-MS molecular mass data, corrected mass data, and theoretical molecular masses (obtained via Expasy MW/pI tool) for exemplary insulin-Fc fusion proteins is shown in Table 4.

TABLE 4

Molecular Mass Determined by MS Compared to Theoretical

| Sequence | Measured Molecular Mass (Da) | Measured Mass, Corrected for N to D transformation (subtract 2 Da) | Desired Homodimer Molecular Mass (theoretical, from AA sequence, Da) |
|---|---|---|---|
| SEQ ID NO: 2 - HEK | 63,767.5 | 63,765.5 | 63,764.3 |
| SEQ ID NO: 3 - HEK | 63,582.8 | 63,580.8 | 63,580.1 |
| SEQ ID NO: 3 - CHO | 63,583.1 | 63,581.1 | 63,580.1 |
| SEQ ID NO: 9 - HEK | 63,727.8 | 63,725.8 | 63,722.3 |
| SEQ ID NO: 10 - HEK | 63,865.6 | 63,863.6 | 63,864.4 |

Example 6: % Homodimer by Size-Exclusion Chromatography (SEC-HPLC)

Figure 3:
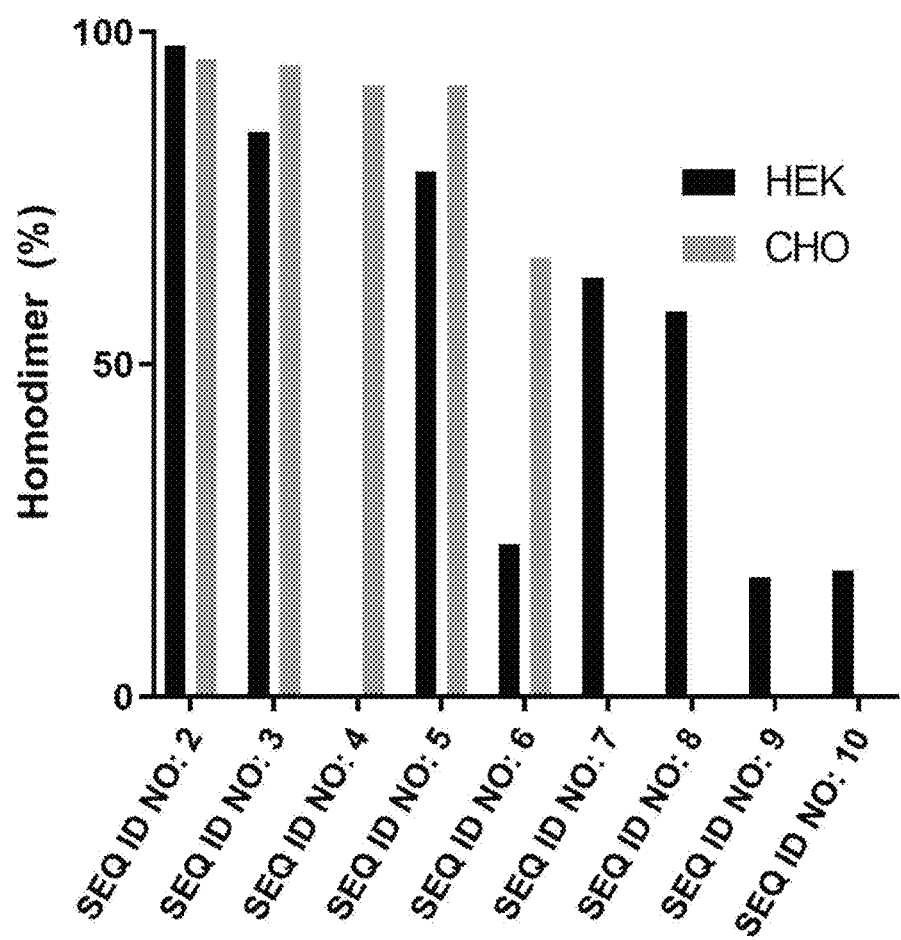
FIG. 3 shows a graph depicting the homodimer percentage for the insulin-Fc fusion proteins of the present technology, calculated using size-exclusion chromatography (SEC-HPLC).

Size-exclusion chromatography (SEC-HPLC) of insulin-Fc fusion proteins was carried out using a Waters 2795HT HPLC (Waters Corporation, Milford, Mass.) connected to a Waters 2998 Photodiode array at a wavelength of 280 nm. 100 µL or less of a sample containing an insulin-Fc fusion protein of interest was injected into a MAbPac SEC-1, 5 μm, 4×300 mm column (ThermoFisher Scientific, Waltham, Mass.) operating at a flow rate of 0.2 mL/min and with a mobile phase comprising 50 mM sodium phosphate, 300 mM NaCl, and 0.05% w/v sodium azide, pH 6.2. The MAbPac SEC-1 column operates on the principle of molecular size separation. Therefore, larger soluble insulin-Fc aggregates (e.g. multimers of insulin-Fc fusion protein homodimers) eluted at earlier retention times, and the non-aggregated homodimers eluted at later retention times. In separating the mixture of homodimers from aggregated multimeric homodimers via analytical SEC-HPLC, the purity of the insulin-Fc fusion protein solution in terms of the percentage of non-aggregated homodimer was ascertained. FIG. 3 shows the homodimer percentage of insulin-Fc fusion proteins manufactured in HEK293 cells and in CHO cells. FIG. 3 demonstrates that the insulin-Fc fusion proteins of the present technology ((SEQ ID NO: 2; SEQ ID NO: 3; SEQ ID NO: 4; SEQ ID NO: 5; SEQ ID NO: 6; SEQ ID NO: 7; and SEQ ID NO: 8) showed relatively high homodimer % when manufactured in one or both of HEK293 and CHO cells. In contrast, SEQ ID NO: 9 and SEQ ID NO: 10 showed relative low homodimer % when manufactured in HEK293 cells.

Example 7: Biotin Conjugates of Insulin-Fc Fusion Proteins

Insulin-Fc fusion proteins were conjugated to biotin as follows: 1 mL of insulin-Fc fusion protein at 0.5 mg/mL in PBS, pH 7.4 was added to a small vial equipped with a magnetic stir bar. Separately, a 30 mM solution of biotinidase-resistant, biotin-BR-PEG4-NHS reagent (Quanta BioDesign, Union County, Ohio) was made in dimethyl sulfoxide (DMSO). A portion of the biotin reagent stock solution was then diluted by 10× in unbuffered, pH 4.0 deionized water just prior to addition of the diluted DMSO/water biotin reagent solution to the insulin-Fc protein solution. An amount of diluted biotin DMSO/water solution was added portion-wise to the insulin-Fc protein solution with intermittent stirring such that the molar ratio of biotin reagent to insulin-Fc protein is between 1-100 mol/mol. Typical biotin conjugation reactions target a biotin reagent to insulin-Fc fusion protein molar ratio of 12:1. The combined biotin reagent-insulin-Fc fusion protein solution was allowed to react for 2 hours or more at room temperature (RT) after which time the unconjugated biotin reagent and DMSO were removed via gel filtration using Zeba™ 10 mL, 7 kDa Pierce™ spin columns (ThermoFisher Scientific, Waltham, Mass.) into endotoxin-free phosphate buffered saline (PBS). The final concentration of the solution was determined by absorbance at 280 nm.

Proof of biotin conjugation was obtained via an ELISA assay as follows. Insulin-Fc fusion protein and a non-biotinylated mouse $IgG_1$ control antibody were diluted to 10 μg/mL in 0.1 M sodium carbonate buffer, and 100 μL/well of each solution was added separately to wells of a 96-well assay Nunc MaxiSorp™ microplate (ThermoFisher Scientific, Waltham, Mass.), and allowed to incubate for 1 hour at RT to coat plate wells. The plates were then washed with a plate washer (Biotek®, Winnoski, Vt.) with PBS containing 0.1% v/v Tween-20 (PBST), and the well surfaces were blocked with 250 μL/well of Pierce™ SuperBlock™ (ThermoFisher Scientific, Waltham, Mass.) for 1 hour at RT. The plate was then washed with PBST, and samples were incubated separately with 100 μL/well with a Streptavidin-HRP conjugate (Abcam, Cambridge, Mass.) diluted between 1:8000 to 1:15,000 from stock. The plate was allowed to incubate for 1 hour at RT. The plate was then washed a final time with a plate washer using PBST, and then again with deionized water 2×. Finally, the plate was incubated with 100 μL/well TMB (Life Technologies (ThermoFisher Scientific), Carlsbad, Calif.) for an appropriate amount of time (typically 5 minutes) to develop the plate, followed by 100 μL/well ELISA stop solution (Boston BioProducts, Ashland, Mass.). The absorbance of the plate was quantified by OD450 nm on a SpectraMax 190 microplate reader (Molecular Devices, Sunnyvale, Calif.). Successful biotin conjugated insulin-Fc fusion protein coated wells typically demonstrated A450 values that were greater with 1.5 OD or more than that of the mouse $IgG_1$ unconjugated control or blank wells.

Example 8: Measurement of Pharmacokinetic (PK) and Pharmocodynamic (PD) Parameters In Vivo Biotin conjugated insulin-Fc fusion protein and unconjugated insulin-Fc fusion protein were assessed for their in vivo pharmacokinetics as follows. N=4 balb/c mice per group (The Jackson Laboratory (JAX), Bar Harbor, Me.) were weighed and two baseline blood glucose measurements were taken using a glucometer (Abbott Laboratories, Abbott Park, Ill.) and one baseline blood sample was collected via submandibular vein for later serum analysis. Mice were then dosed intraperitoneally (i.p.) with 2 mg/kg of insulin-Fc fusion protein. Blood glucose measurements and blood collections for serum analysis were taken in intervals between t=0 and t=21 days. Blood was allowed to clot, and after centrifugation of the clotted samples, serum was obtained and frozen immediately in a polypropylene 96-well plate and stored at −20° C. until analysis was conducted. Separate control experiments were conducted with recombinant human insulin (RHI) (Sigma-Aldrich Corporation, ST. Louis, Mo.) to demonstrate the difference in glucose-lowering activity of insulin-Fc fusion protein versus the RHI control groups.

ELISA-Based PK Assay.

The pharmacokinetic data was obtained via ELISA analysis as follows. 96-well Nunc MaxiSorp™ plates (ThermoFisher Scientific, Waltham, Mass.) were coated with 10 μg/mL of Pierce™ NeutrAvidin™ (ThermoFisher Scientific, Waltham, Mass.) for 1 hour at RT, after which time the plates were washed and were blocked with 250 μL/well of Pierce™ SuperBlock™ (ThermoFisher Scientific, Waltham, Mass.) overnight at 4° C. Next, 100 μL of diluted in vivo serum samples (typically 2-200× dilution factor or more) and, in separate wells, biotin-conjugated insulin-Fc fusion protein standards with known concentrations in PBST/SB were loaded onto the plate to construct a standard curve (3× serial dilutions) and were incubated for 1 hour at RT. Plates were washed using a plate washer (Biotek®, Winnoski, Vt.) and 100 μL of the appropriate secondary antibody Rabbit-anti-human IgG(H+L)-HRP (Bethyl Laboratories, Montgomery, Tex.)) diluted 1:10,000 from stock into PBST/SB, was added to the plate and incubated for 1 hour at RT. Plates were washed using a plate washer, and 100 μl of TMB solution (Life Technologies (ThermoFisher Scientific), Carlsbad, Calif.) was loaded into each well of the plate. Once the plate was developed for the appropriate amount of time, 100 μL of stop solution (Boston BioProducts, Ashland, Mass.) was added to each well. Plates were read on SpectraMax 190 microplate reader (Molecular Devices, Sunnyvale, Calif.) at OD450 nm, and concentrations of biotin-conjugated insulin-Fc in serum were obtained by comparing the OD450 nm of the diluted serum samples against the OD450 nm curve obtained for the standards. The data was then analyzed via Prism (GraphPad Software, Inc., La Jolla, Calif.) as described further below.

The pharmacokinetic data was also optionally obtained through detection of the proinsulin portion of insulin-Fc fusion protein using Mercodia Mouse Insulin ELISA kits (Mercodia, Uppsala, Sweden) according to the manufacturer's protocol and with the manufacturer's standard curve to report values of insulin-Fc protein concentrations in serum samples in mouse insulin equivalent units. Concentrations for each sample were determined, back multiplied by their dilution factor and analyzed via Excel (Microsoft, Seattle, Wash.) and Prism (GraphPad Software, Inc., La Jolla, Calif.) software to calculate Cmax, tmax, AUC, and terminal phase elimination rate (half-life).

Figure 4A:
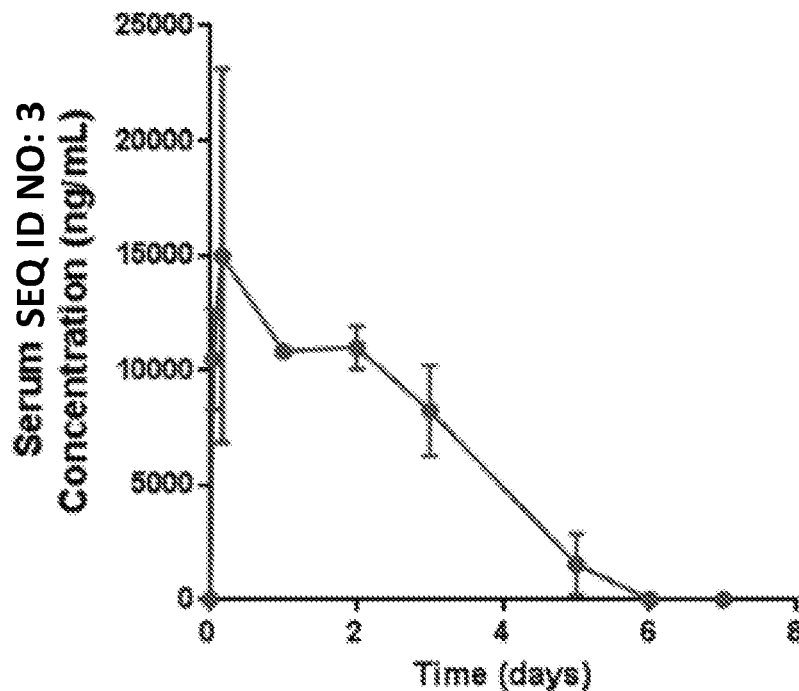
FIG. 4A shows a graph depicting the insulin-Fc fusion protein concentration over time when an exemplary insulin-Fc fusion protein (SEQ ID NO: 3) was dosed at 2 mg/kg i.p. into BALB/c mice.

FIG. 4A illustrates the serum concentration in ng/mL as a function of time in days after an exemplary insulin-Fc fusion protein (SEQ ID NO: 3) was dosed i.p. As shown in FIG. 4A, the serum half-life of the tested insulin-Fc fusion protein was about 1 day.

Figure 4B:
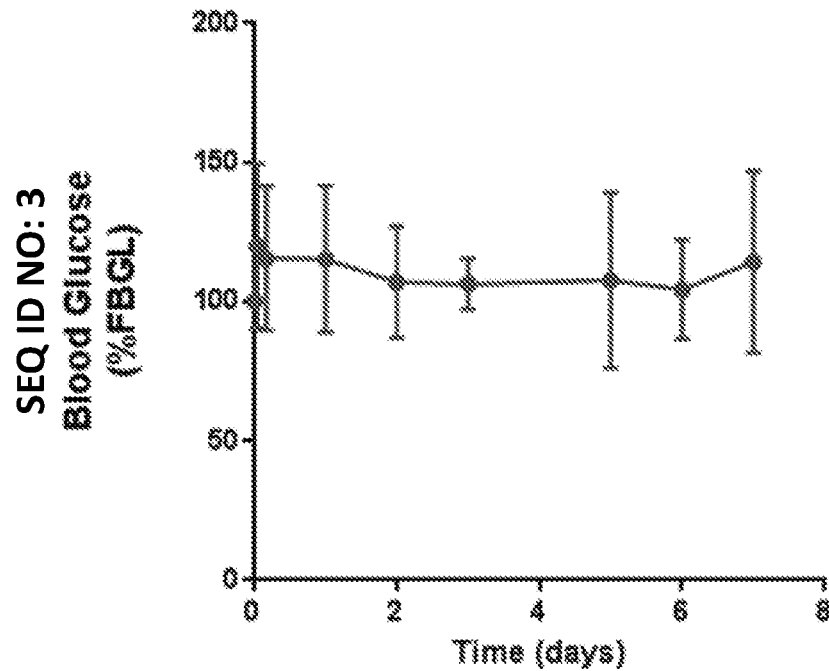
FIG. 4B is a graph depicting serum fasting blood glucose levels (FBGL) over time when an exemplary insulin-Fc fusion protein (SEQ ID NO: 3) was dosed i.p. into BALB/c mice.

The results of the fasting blood glucose (% FBGL) measurements demonstrate that there was no observed glucose lowering activity of the tested biotin conjugated insulin-Fc fusion protein. See FIG. 4B.

Figure 5:
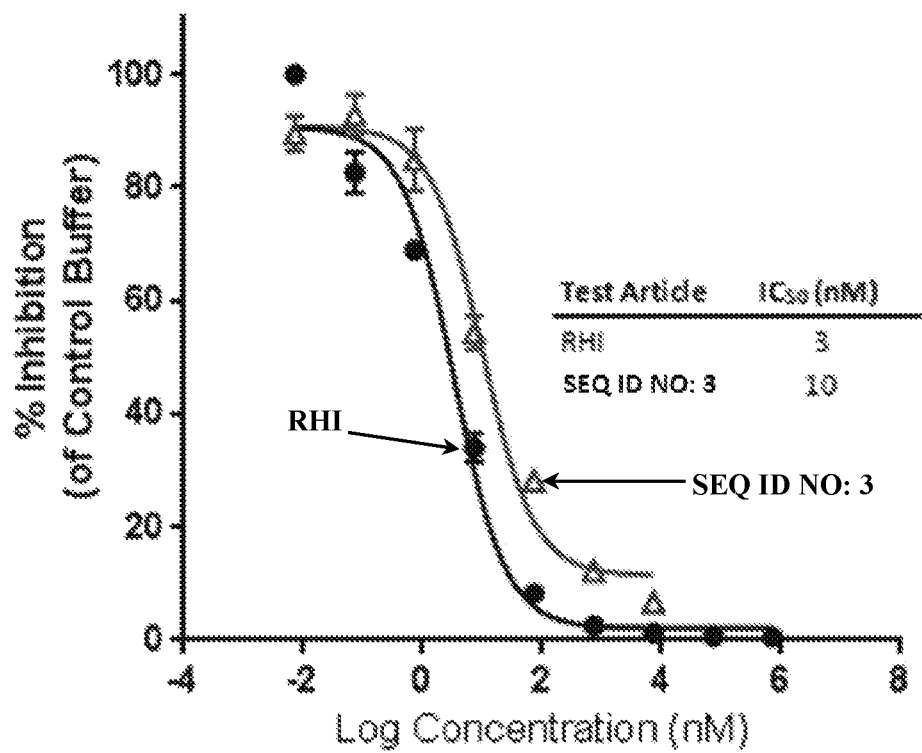
FIG. 5 shows a graph depicting the inhibition of $^{125}I$-labeled recombinant insulin (RHI) binding to insulin autoantibodies (IAAs) in the serum of a pre-diabetic, IAA-positive human subject via radioimmunoassay for RHI ($IC_{50}$=3 nM) and an exemplary insulin-Fc protein (SEQ ID NO: 3) ($IC_{50}$=10 nM).

Example 9: Determination of Binding Affinity to Insulin Autoantibodies (IAAs) in Human Serum Samples The binding affinity of insulin-Fc fusion proteins to circulating human serum insulin autoantibodies (IAAs) was determined as follows. The determination was used as a proxy for the affinity of the insulin-Fc fusion proteins to insulin$^+$ B cells from which the IAAs originated, as antibodies are the secreted forms of B cell receptors in mammals. Human serum samples from pre-diabetic, IAA-positive subjects (Barbara Davis Center for Childhood Diabetes) were mixed in vitro with radiolabeled insulin and serially-diluted concentrations of either unlabeled recombinant human insulin (RHI) or insulin-Fc fusion proteins (e.g., SEQ ID NO: 3) to measure inhibition of $^{125}$I-radiolabeled RHI binding to IAAs. After incubating mixtures for 1 hour at RT, the mixtures were added to a suspension of anti-human IgG beads (CaptureSelect, GE Healthcare, Little Chalfont, United Kingdom). The beads were washed, and the resulting beads were analyzed using a scintillation counter (gamma radiation counter). Strong binding of the RHI control or insulin-Fc fusion protein to the human serum IAAs, inhibits IAA binding to $^{125}$I-labeled insulin, thus resulting in lower gamma radiation counts. Weaker binding of RHI control or insulin-Fc fusion protein, results in higher gamma counts. The data was used to construct a binding curve and analyzed using Prism (GraphPad Software, La Jolla, Calif.) to determine the concentration to inhibit 50% of the radiolabeld insulin binding to the IAAs ($IC_{50}$). As shown in FIG. 5, SEQ ID NO: 3 insulin-Fc fusion protein ($IC_{50}$=10 nM) had a similar affinity compared to RHI ($IC_{50}$=3 nM) for the pooled, pre-diabetic human IAA samples, demonstrating that SEQ ID NO: 3 insulin-Fc fusion protein is useful in targeting anti-insulin B cell clones in a subject.

These results demonstrate that the insulin-Fc fusion proteins of the present technology are useful in methods for treating or preventing an autoimmune disease (e.g., autoimmune diabetes, e.g., Type 1 diabetes).

Example 10: In Vitro Reduction of Anti-Insulin B Cells—125Tg NOD Mice

To assess the ability of the insulin-Fc fusion proteins of the present technology to specifically delete insulin$^+$ B cells, an in vitro assay was developed using 125Tg NOD mouse splenocytes and primary rat alveolar macrophages (AMs, lung lavage) or mouse macrophages (MMs from bone marrow) from animals bred at Akston Biosciences (Beverly, Mass.). The spleens were harvested, the erythrocytes were lysed, and the splenocytes purified by Ficoll prep to obtain a purified mixture of T cells and B cells. The advantage of the 125Tg NOD model is that approximately 50-80% of the splenocytes are insulin$^+$ B cells, which facilitates experimental testing. The purified splenocyte mixture was then co-cultured with rat AMs or MMs over a period of three days (~5×10$^5$ splenocytes with 5×10$^4$ AMs or MMs per 96-microtiter well) along with varying concentrations of an exemplary insulin-Fc fusion protein and control. After incubation, the cells were washed repeatedly and incubated overnight in fresh medium to ensure complete removal of the exemplary insulin-Fc fusion protein. Cells were then harvested and labeled with a cocktail of 1 μg anti-B220-PE mAb, 0.7 μg anti-IgM-PECy7 mAb, and 5 μL of RHI-μBeads (made using RHI (Sigma-Aldrich Corporation, St. Louis, Mo.) and a NHS-activated microbead kit (Miltenyi Biotec, Cambridge, Mass.)). Next, beads are additionally labeled with anti-μBead-APC mAb (Miltenyi Biotec, Cambridge, Mass.). Cells were fixed after washing and analyzed by FACS.

FACS analysis was performed in a four-color 2-laser FACSCalibur® flow cytometer using CellQuest Pro software (BD Biosciences, San Jose, Calif.). Live lymphocytes were gated in a FSC vs. SSC scatter and the gated lymphocytes were analyzed in FL2 vs. FL4 dot plot to enumerate the B220$^+$ B cells and B220$^+$ insulin$^+$ B cells (insulin-specific B cells) using quadrant stats. The quadrant gating of insulin$^+$ and insulin(−) populations were set based on the B220(−) insulin(−) population levels and on the inhibition control samples (inhibited by adding unlabeled RHI prior to labeling of the cells). The B cell receptor density on the B cells was also estimated using the median fluorescent intensity (MFI) of anti-IgM-PECy7 in a FL2 vs. FL3 dot plot.

Figure 6A:
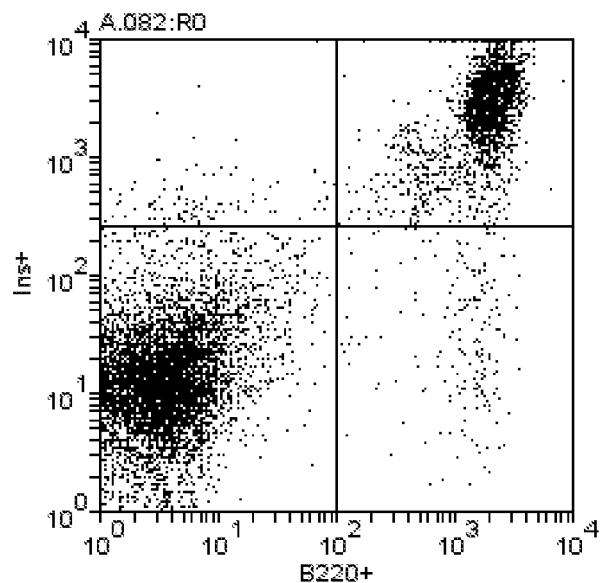
FIG. 6A shows a graph depicting representative FACS dot plots for % insulin$^+$ B cells from 125Tg splenocyte/rat AM co-cultures treated with vehicle.
Figure 6B:
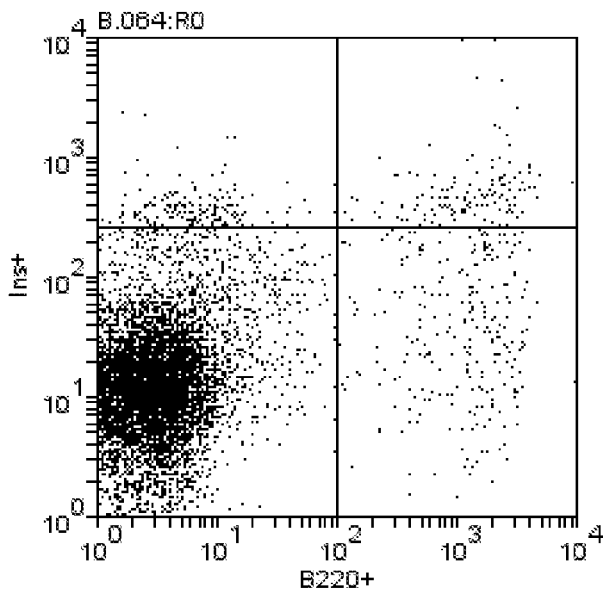
FIG. 6B shows a graph depicting representative FACS dot plots for % insulin$^+$ B cells from 125Tg splenocyte/rat AM co-cultures treated with an exemplary insulin-Fc fusion protein (SEQ ID NO: 3).

The results of the FACS analysis are shown in FIG. 6A-6B. B220 is a B cell surface marker that allows quantification of total B cells in a mixture of multiple cell types. B220$^+$ refers to the fraction of cells that are labeled with anti-B220-fluorophore conjugate that bind and fluoresce as B220$^+$ B cells in a flow cytometer. Ins$^+$ refers to the fraction of cells that bind a labeled insulin (or insulin conjugated bead) of all types that are quantified in a flow cytometer. By assessing the Ins$^+$ and B220$^+$ fraction, it is possible to ascertain the percentage of cells that are both B cells and capable of binding insulin.

The targeted cell removal with SEQ ID NO: 3 was highly specific for B220$^+$ insulin$^+$ B cells, leaving both the B220$^+$ insulin(−) B cells (lower right quadrants, FIGS. 6A and 6B) and B220(−) insulin(−) cell populations (lower left quadrants, FIGS. 6A and 6B) indistinguishable from controls. The overall dose response curve for SEQ ID NO: 3-mediated deletion of insulin$^+$ B cells is depicted in FIG. 6C. These data demonstrate that an exemplary insulin-Fc fusion protein (SEQ ID NO: 3) caused a >95% reduction in B220$^+$ insulin$^+$ B cells from the co-culture at a concentration of 80 nM and that the effect was dose dependent with an $EC_{50}$ of about 70 pM.

These results demonstrate that the insulin-Fc fusion proteins of the present technology are useful in methods for treating or preventing an autoimmune disease (e.g., autoimmune diabetes, e.g., Type 1 diabetes).

Example 11: In Vivo Reduction of Anti-Insulin B Cells—VH125 NOD Mice

Experiments were carried out using an exemplary insulin-Fc fusion protein, SEQ ID NO: 3, or a vehicle control formulation via twice-weekly i.p. injections at 0.4 mg/kg for two weeks in male and female VH125 NOD mice (N=3-6 mice per group). After two weeks of dosing, mice were anesthetized using isoflurane during blood collection (sub-mandibular vein), followed by carbon dioxide asphyxiation and collection of lymph nodes, bone marrow, and/or spleens was conducted under sterile conditions. Blood and spleen samples were processed and analyzed as described in Examples 12-13. The results of these experiments are shown in FIGS. 7A-7H, which demonstrate the ability of the exemplary insulin-Fc fusion protein (SEQ ID NO: 3), to achieve removal of insulin$^+$ B cells in VH125 NOD mice in blood and spleen while preserving the insulin(−) B cell population.

These results demonstrate that the insulin-Fc fusion proteins of the present technology are useful in methods for treating or preventing an autoimmune disease (e.g., autoimmune diabetes, e.g., Type 1 diabetes).

Example 12: In Vivo Reduction of Anti-Insulin B Cells—Whole Blood Analysis (VH125 NOD Mice)

A procedure was developed for analyzing the insulin-specific B cells in peripheral blood collected from VH125 NOD mice following treatment with exemplary insulin-Fc fusion proteins described herein. Approximately 200-400 µL of blood was collected from treated mice by sub-mandibular (SMD) venipuncture into 5 mL microcentrifuge with 2 mL of 2 mM EDTA/HBSS/Gentamycin, immediately mixed by inverting to prevent clotting. Tubes were then centrifuged at 500×g for 7 minutes and washed twice with 5 mL of HBSS/heparin buffer at 500×g for 7 minutes. Blood pellet was resuspended in complete IMDM medium (10% FBS, 5 mg/mL gentamycin and 2-ME) with heparin and incubated in 10 well plates overnight at 37° C. to allow turnover of B cell receptors (BCR) so that they were freed from any endogenous mouse insulin or any residual insulin-Fc fusion protein present from the in vivo experiments. Blood cells were then harvested into 5 mL tubes, centrifuged at 500×g for 7 minutes, cell pellets were resuspended in 5 mL of RBC-Lysis buffer and kept for 5 minutes at room temperature. After lysing RBCs, leukocytes were washed twice with HBSS/2% FBS at 500×g for 7 minutes and finally suspended in 100 µL of cold FACS staining medium containing 10 µL of mouse FcR block (Miltenyi Biotech, Cambridge, Mass.), 1 µg of mAb rat anti-mouse B220-Alexa Fluor® 488 (BioLegend®, San Diego, Calif.), 0.7 µg of rat anti-mouse IgM-PE/Cy7 mAb and 100 equivalent volume (12.5 µL) of RHI-conjugated micro beads (Miltenyi Biotech, Cambridge, Mass.) and kept for 30 minutes at 4° C. Blood cells were washed once by adding 2 mL of ice-cold FACS wash buffer and centrifuging at 500×g for 7 minutes. Cells were finally labeled with 6 µL of anti-pead-APC (Miltenyi Biotech, Cambridge, Mass.) in 100 µL of FACS staining buffer for 20 minutes at 4° C., washed once with 2 mL of FACS wash buffer and resuspended in 150 µL of 2% paraformaldehyde buffer for FACS analysis. For VH125 transgenic mice, due to low frequency of insulin-specific B cells in blood, an optional enrichment procedure was conducted before FACS analysis. For the enrichment procedure, approximately 500-600 µL blood was required which necessitated pooling of N=3 or more individual mouse blood samples for a given treatment group. The blood labeling procedure was combined with the insulin-specific B cell enrichment protocol described in Example 12. The labeled blood cells after fixing and washing steps could be enriched using a MS column as described above for VH125 NOD spleen cells before FACS analysis.

Figure 7A:
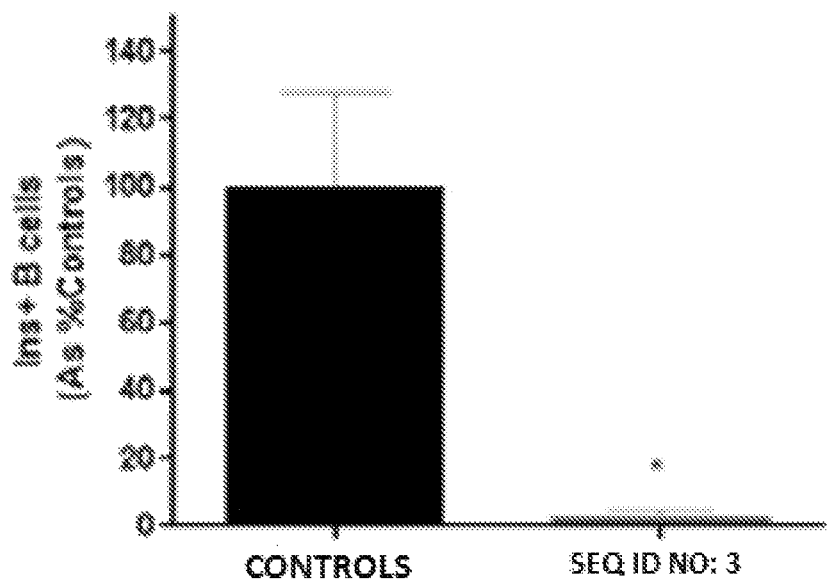
Figure 7B:
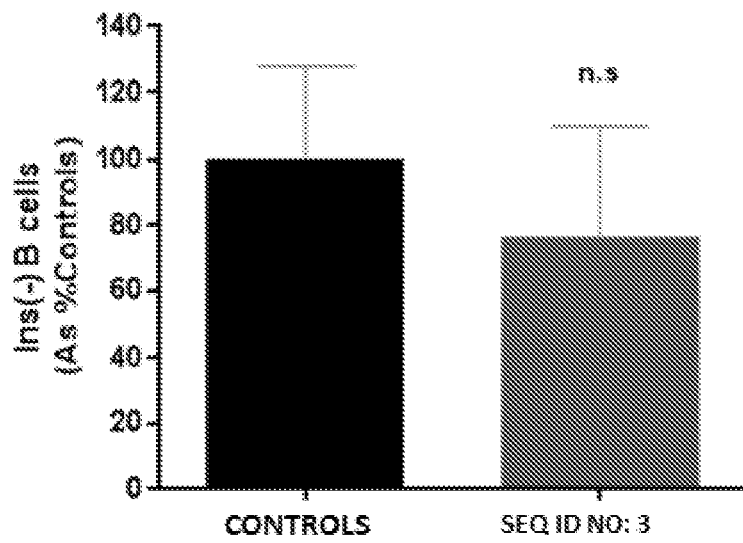

FIG. 7A is a graph showing the insulin$^+$ B cells in blood as a percent of vehicle-treated controls; FIG. 7B is a graph showing the insulin(−) B cells in blood as a percent of controls. It can be seen from FIG. 7A and FIG. 7B that the exemplary insulin-Fc fusion protein (SEQ ID NO: 3) significantly reduced Ins+ B cells, while not significantly reducing Ins(−) B cells (* means that the result is statistically significant, p value ≤0.05 (student t-test) and, n.s. means that the result is not statistically significant, with a p value >0.05 (student t-test)).

These results demonstrate that the insulin-Fc fusion proteins of the present technology are useful in methods for treating or preventing an autoimmune disease (e.g., autoimmune diabetes, e.g., Type 1 diabetes).

Example 13: In Vivo Reduction of Anti-Insulin B Cells—Spleen Analysis (VH125 NOD Mice)

Enrichment of Insulin-Specific B Cells from Mouse Splenocytes for FACS Analysis.

This procedure can be applied to analyze insulin-specific B cells in freshly isolated splenocytes from VH125 NOD mice. Since the frequency of insulin-specific B cells in VH125 NOD mice is 2-5% of all B cells, a magnetic activated cell sorting (MACS) column enrichment procedure was used to enrich the insulin-specific B cells from total splenocytes to properly quantitate the extent of in vivo insulin-specific B cell reduction. Approximately, ~10×10$^6$ spleen cells were labeled for each enrichment procedure. When freshly isolated VH125 NOD spleen cells were enriched, the cells were incubated with complete culture medium (IMDM or DMEM medium with 10% FBS, 5 mg/mL gentamycin and 2-mercaptoethanol) in a 37° C., 5% CO$_2$ incubator overnight to allow turnover of B cell receptors (BCR) so that they are freed from any endogenous mouse insulin or any residual insulin-Fc fusion protein present from the in vivo experiments. Cells were harvested into 15 mL tubes and Ficoll purified by underlaying the cells with 2.5 ml of Ficoll and centrifuging at 800×g for 15 minutes.

After washing twice with HBSS/2% FBS buffer at 500×g for 10 minutes, cells were resuspended in 250 µL FACS staining buffer (HBSS/2 mM EDTA/0.1% Na-azide plus 4% horse serum) and kept at 4° C. for 20-30 minutes for blocking. Cells were counted and adjusted to 10$^7$ cells in 250 µL volume. Cells were labeled with 3.5 µg of mAb rat anti-mouse B220-Alexa Fluor® 488 (BioLegend), 2.5 µg of rat anti-mouse IgM-PE/Cy7 mAb, 1.6 µg of BV510-anti-mouse CD23, 0.7 µg of BV421-anti-mouse CD21, 1.6 µg of PE-anti-mouse CD43 and 200 ng equivalent (25 µL) RHI-conjugated microbeads (described above) for 30 minutes at 4° C. Cells were washed once by adding 5 mL of ice-cold FACS wash buffer and centrifuging at 500×g for 7 minutes. Cells were then resuspended in 100 µL FACS staining buffer containing 10 µL of anti-µBead-APC (Miltenyi Biotec, Cambridge, Mass.) for 20 minutes at 4° C., and washed once with 2-4 mL of ice-cold FACS wash buffer at 500×g for 7 minutes. Cells were then fixed with 200 mL of 21% freshly prepared ultra-pure paraformaldehyde at RT for 5 minutes. After fixation, cells were washed twice with FACS wash buffer and finally resuspended in 600 µL of MACS buffer (HBSS/0.5% horse serum/0.1% azide/2 mM EDTA). MS columns (Miltenyi Biotec, Cambridge, Mass.) were placed in the magnetic separator, washed once with 500 µL of MACS buffer and the cell suspension was then added to the column to pass through. Approximately 100 µL of labeled cell suspension was kept without passing through the MS column for analyzing the un-enriched total cells. MS columns were then washed three times with 3×500 µl MACS buffer. Microbead labeled insulin-specific B cells held in the column were then eluted by removing the columns from the magnet, adding 1 mL of MACS buffer and plunging them using the plunger provided with MS column into a 1.8 mL microcentrifuge tube. Enriched cells were then centrifuged at 500×g for 7 minutes and resuspended in 250 µL of MACS buffer for FACS analysis.

FIG. 7C is a graph depicting the insulin$^+$ B cells in all spleen compartments. According to FIG. 7C, the exemplary insulin-Fc fusion protein (SEQ ID NO: 3) significantly reduced insulin$^+$ B cells in all spleen compartments (** means p value ≤0.01 (statistically significant)).

FIG. 7D shows the insulin$^+$ B cells in the marginal zone spleen compartment (CD21$^{High}$ CD23$^{High}$) As shown in FIG. 7D, the exemplary insulin-Fc fusion protein (SEQ ID NO: 3) significantly reduced insulin$^+$ B cells in the marginal zone spleen compartment (* means p value ≤0.05 (statistically significant)).

FIG. 7E shows the insulin$^+$ B cells in the follicular spleen compartment (IgM$^{Mid}$ CD21$^{Mid}$). According to FIG. 7E, the exemplary insulin-Fc fusion protein (SEQ ID NO: 3) significantly reduced insulin$^+$ B cells in the follicular spleen compartment (* means p value ≤0.05 (statistically significant)).

FIG. 7F shows the insulin$^+$ B cells in the T1 spleen compartment (CD21$^{Low}$CD23$^{low}$). As shown in FIG. 7F, the exemplary insulin-Fc fusion protein (SEQ ID NO: 3) significantly reduced insulin$^+$ B cells in the T1 spleen compartment (* means p value ≤0.05 (statistically significant)).

FIG. 7G shows the insulin$^+$ B cells in the T2 spleen compartment (IgM$^{High}$ CD21$^{Mid}$). According to FIG. 7G, the exemplary insulin-Fc fusion protein (SEQ ID NO: 3) has significantly reduced insulin$^+$ B cells in the T2 spleen compartment (* means p value ≤0.05 (statistically significant)).

FIG. 7H shows the insulin$^+$ B cells in the pre-marginal zone spleen compartment (IgM$^{High}$ CD21$^{High}$) As shown in FIG. 7G, the exemplary insulin-Fc fusion protein (SEQ ID NO: 3) significantly reduced insulin$^+$ B cells in the pre-marginal zone spleen compartment (* means p value ≤0.05 (statistically significant)).

These results demonstrate that the insulin-Fc fusion proteins of the present technology are useful in methods for treating or preventing an autoimmune disease (e.g., autoimmune diabetes, e.g., Type 1 diabetes).

Example 14: In Vivo Reduction of Anti-Insulin B Cells—Bone Marrow Analysis (VH125 NOD Mice)

Sample Processing and Enrichment (Bone Marrow).

An in vivo experiment similar to the one described in Example 11 was conducted, except in this case the test articles were dosed twice weekly from 6 weeks of age through 34 weeks of age. VH125 NOD tibias and femurs were dissected from the surrounding muscles and tendons after conducting the in vivo experiment described in Example 11. After muscles and tissue debris were scraped off from bones using sterile scalpels, bones were washed once with 70% isopropanol and twice with sterile PBS. Both ends of each bone were cut with sterile scissors and the marrow was flushed by plunging approximately 8-10 mL of sterile HBSS/2% FBS buffer filled in a 20 mL syringe and 25 G needle inserted through one end of the bone. Bone marrow suspension was filtered through 20 µm cell strainer and then centrifuged at 500×g for 10 minutes. After aspirating the supernatant, red blood cells were lysed using RBC Lysis buffer for 5 minutes at room temperature and then washed twice with HBSS/2% FBS buffer. The bone marrow cell suspension was resuspended in complete medium (DMEM, 5% BSA, 1 mM sodium pyruvate, 50 µg/mL gentamycin, 5×10$^{-5}$ M beta mercaptoethanol) and incubated overnight at 37° C. to allow for BCR turnover. At the end of the incubation period, Ficoll density gradient separation was used to clear the bone marrow mononuclear cells from debris.

Cells were then suspended in FACS staining buffer (PBS, 2% BSA, 0.1% sodium azide) and Fc Block (Mitenyi Biotech, Cambridge, Mass.). Biotinylated insulin and other B cell markers were added to the cells on ice. After 30 minutes, cells were washed and re-suspended in HBSS buffer with 2% PFA. Cells were washed again and a subsequent staining step in FACS staining buffer with Streptavidin-Alexa Fluor® 647 was completed. Miltenyi anti-Alexa Flour® 647 microbeads (Miltenyi Biotec, Cambridge, Mass.) were then used, for an optional positive enrichment step (according to the manufacturer protocol). A BD FACSCalibur™ (BD Biosciences, San Jose, Calif.) was used for sample acquisition with gating of the high MFI insulin+ B cells. Voltages and compensation were set using single stain controls. Data were analyzed using FlowJo software (FlowJo, LLC, Ashland, Oreg.).

Figure 8A:
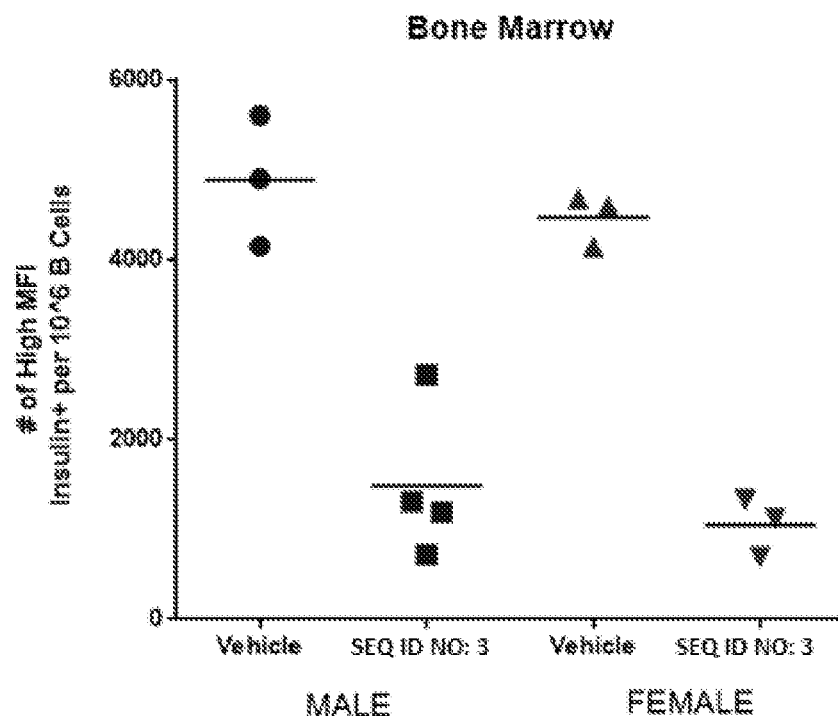
FIGS. 8A-8B are graphs showing in vivo insulin$^+$ B cell reduction data.

The bone marrow analysis from study week 34 is illustrated in FIG. 8A, which shows significant reduction of anti-insulin B cells in both male and female VH125 mice after treatment with SEQ ID NO:3.

These results demonstrate that the insulin-Fc fusion proteins of the present technology are useful in methods for treating or preventing an autoimmune disease (e.g., autoimmune diabetes, e.g., Type 1 diabetes).

Example 15: In Vivo Reduction of Anti-Insulin B Cells—Lymph Node Analysis (VH125 NOD Mice)

Figure 8B:
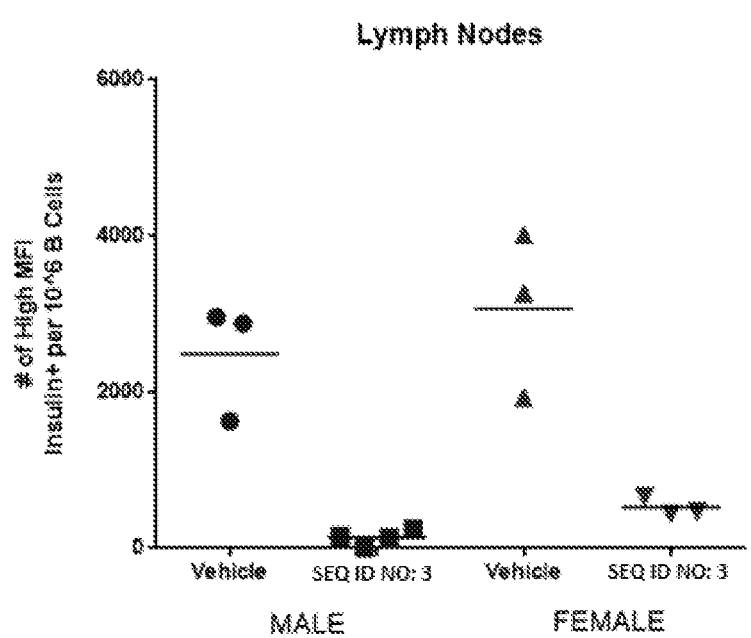

The in vivo experiment of Example 14 was conducted, and lymph nodes and resulting lymph node cell suspensions were processed and collected in a similar manner to the procedure previously described for splenocytes, except that for a given animal two to four lymph nodes were pooled together as one sample, and no Ficoll purification and no lysis buffer steps were performed. Resulting lymph node cell suspensions were labeled in a similar manner to that described for the bone marrow cell suspensions described above. Lymph node analysis from study week 34 is depicted in FIG. 8B, which shows significant reduction of anti-insulin B cells in both male and female VH125 mice after treatment with SEQ ID NO:3.

These results demonstrate that the insulin-Fc fusion proteins of the present technology are useful in methods for treating or preventing an autoimmune disease (e.g., autoimmune diabetes, e.g., Type 1 diabetes).

Example 16: T-cell Activation Assay—Single Concentration

The ability of insulin-Fc fusion proteins to activate T cells was assessed by measuring IL-2 secretion by a 5KC-3-4 mouse IAg7 T cell hybridoma with a reactive T cell receptor (TCR) for the insulin B-chain epitope (positions 9 through 23 on the insulin B-chain). Insulin-specific B cells were isolated from 125Tg NOD spleens for use as antigen presenting cells. Spleens were isolated aseptically, and cells were isolated in sterile buffer containing 2% FBS, filtered through 40 μm sterile cell strainers. Red blood cells lysed using ACK Lysing Buffer (ThermoFisher Scientific, Waltham, Mass.) followed by two washes with 2% FBS in sterile buffer. B cells were isolated from the spleen cell mixture using a no-touch B cell isolation kit according to manufacturer's directions (Mouse Pan B Cell Isolation Kit II, Miltenyi Biotec, Cambridge, Mass.). Cells were then used as antigen presenting cells without activation or fixation. 5KC-3-4 cells and B cells were mixed and resuspended in FBS at $6.67 \times 10^6$/mL and $1.33 \times 10^7$/mL respectively. Test compounds were buffer exchanged into IMDM containing 0.002% Tween-80 1 mM pyruvate 55 μM beta-mercaptoethanol, and Gentamicin using a 7 kDa MWCO Zeba spin column, and then diluted to 0.2 mg/mL. As a positive control, recombinant human insulin (RHI) at 0.018 mg/mL was prepared in the same medium so that the RHI (MW~5.8 kDa) is compared at an equimolar concentration to that of the insulin-Fc fusion proteins (MW~63.5 kDa). 15 μL cell suspension (containing $1 \times 10^5$ 5 KC-3-4 and $2 \times 10^5$ B cells) and 150 μL test compound were combined in a 96-well tissue culture plate. Following an overnight incubation at 37° C., culture medium was collected and centrifuged at 3500 rpm, 5 minutes at 4° C. Supernatant was then assayed for IL-2 via a mouse IL-2 Quantikine ELISA Kit (R&D Systems, Minneapolis, Minn.) according to the manufacturer's protocol.

Figure 9:
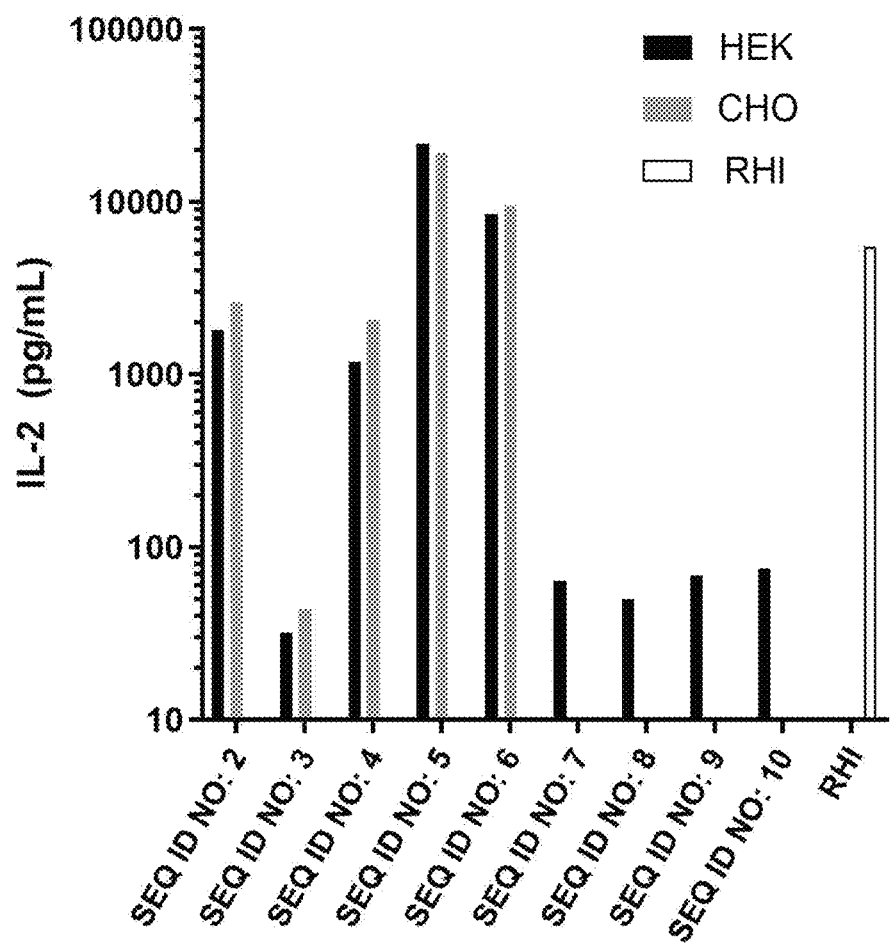
FIG. 9 is a graph showing IL-2-mediated 5KC-3-4 T cell line stimulation ELISA data for several insulin-Fc fusion proteins of the present technology (SEQ ID NOs: 2, 3, 4, 5, 6, 7, 8, 9, and 10) and a recombinant human insulin (RHI) control.

FIG. 9 shows the results of the T cell stimulation experiment (as indicated by IL-2 secretion) ELISA in pg/mL. FIG. 9 demonstrates that some insulin-Fc fusion proteins exhibit very low or non-stimulatory behavior with respect to the 5KC-3-4 cells (SEQ ID NO: 3—T cell stimulation=32 pg/mL IL-2), while some insulin-Fc fusion proteins are T cell stimulatory (SEQ ID NO: 5—T cell stimulation=21,635 pg/mL IL-2). RHI control was also somewhat stimulatory (RHI-T cell stimulation=5,503 pg/mL IL-2).

These results demonstrate that the insulin-Fc fusion proteins of the present technology are useful in methods for treating or preventing an autoimmune disease (e.g., autoimmune diabetes, e.g., Type 1 diabetes).

Example 17: Inhibition of T-Cell Activation Assay—Multiple Concentrations

Insulin B9-23 reactive 5KC-3-4 T cells were mixed with 125Tg B cells, which acted as the antigen presenting cells in the assay. To this cell suspension was added a fixed concentration (10 ng/mL) of insulin-Fc fusion protein SEQ ID NO: 5 as stimulatory control that was premixed with various serially diluted concentrations of test compounds between 130 and 10,000 ng/mL, and the assay plate was incubated overnight at 37° C. IL-2 secretion was measured, and $IC_{50}$ concentrations were determined from the data.

A more detailed description of the assay is as follows. Insulin specific B cells were isolated from 125Tg NOD spleens for use as antigen presenting cells. Spleens were isolated aseptically, and cells were isolated in sterile buffer containing 2% FBS, filtered through 40 μm sterile cell strainers. Red blood cells lysed using ACK Lysing Buffer (ThermoFisher Scientific, Waltham, Mass.) followed by two washes with 2% FBS in sterile buffer. B cells were isolated from the spleen cell mixture using a no-touch B cell isolation kit according to manufacturer directions (Mouse Pan B Cell Isolation Kit II, Miltenyi Biotec, Cambridge, Mass.). Cells were then used as antigen presenting cells without activation or fixation. 5KC-3-4 and 125Tg B cells were resuspended in 40% FBS (in serum free medium) at $2.67 \times 10^6$ and $3.6 \times 10^6$ cells per mL, respectively. Test compounds were diluted to $2 \times (20,000$ ng/mL$)$ in IMDM containing 1 mM pyruvate, 125 μM β-mercaptoethanol, and 0.002% Tween-80, and seven further 1:5 serial dilutions were prepared in the same medium. In addition to tested insulin-Fc fusion proteins, purified human IgG was also used as a non-inhibitory control. Insulin-Fc fusion protein SEQ ID NO: 5 was diluted to 4× (10 ng/mL) in the same medium. 37.5 μL cell suspension (containing $1 \times 10^5$ 5 KC-3-4 and $1.4 \times 10^5$ 125 Tg B cells), 37.5 μL SEQ ID NO: 5 (or medium) and 75 μL test compound (or medium) were combined in a 96-well tissue culture plate. Following an overnight incubation at 37° C., culture medium was collected and centrifuged at 3500 rpm, 5 minutes at 4° C. Supernatants were then assayed for IL-2 levels via a mouse IL-2 Quantikine ELISA Kit (R&D Systems, Minneapolis, Minn.) according to the manufacturer's protocol.

Figure 10:
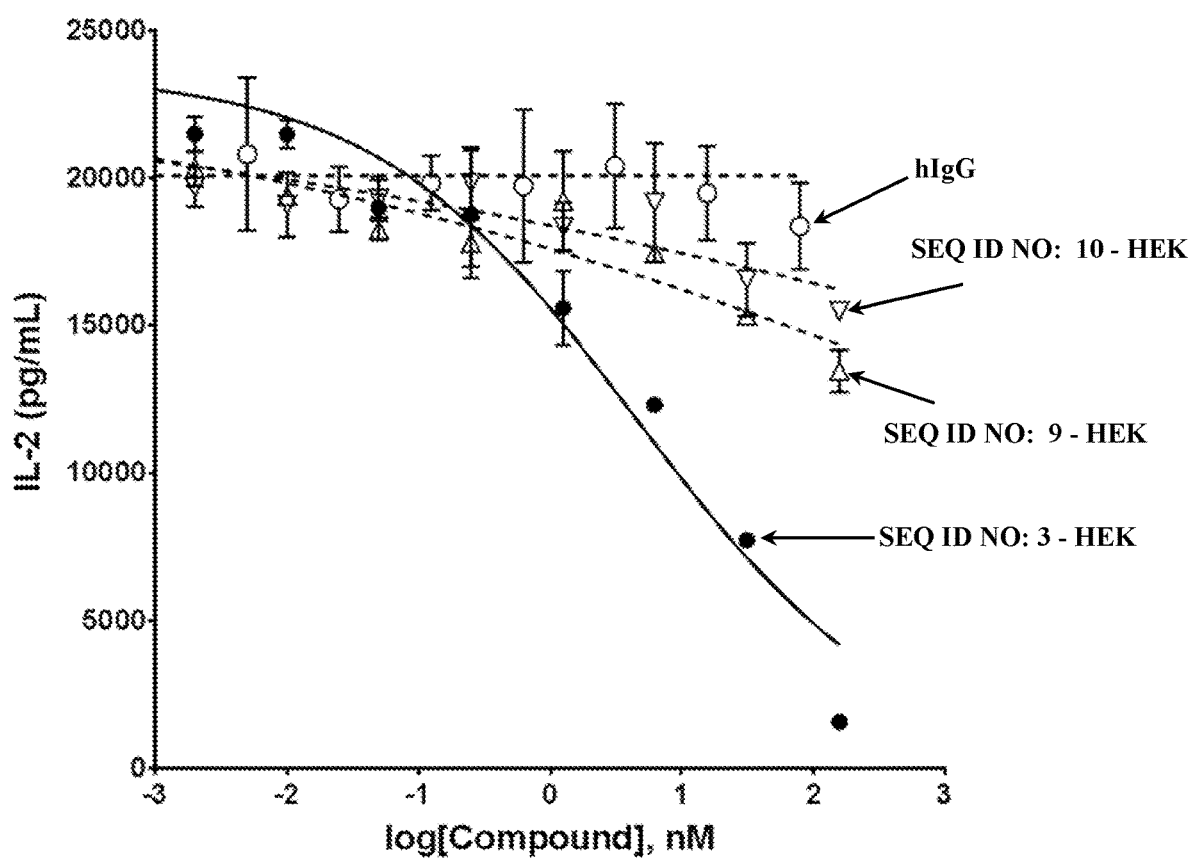
FIG. 10 is a graph showing competitive inhibition of IL-2 secretion induced by a T cell stimulatory compound for an exemplary insulin-Fc fusion protein (SEQ ID NO: 3) and various contrasting insulin-Fc fusions proteins (SEQ ID NOs: 9 and 10) and a control over multiple concentrations.

FIG. 10 shows the results of the competitive inhibition of IL-2 secretion in the presence of a fixed amount of insulin-specific T cell stimulatory compound (SEQ ID NO: 5). Table 5 shows the competitive inhibition of IL-2 secretion induced by a T cell stimulatory compound for an exemplary insulin-Fc fusion protein (SEQ ID NO: 3) and various contrasting insulin-Fc fusions proteins (SEQ ID NO: 9 and SEQ ID NO: 10) and a hIgG negative control at the $IC_{50}$ (hIgG). Lower $IC_{50}$ values indicate more potent inhibitors of IL-2 secretion.

TABLE 5

Competitive Inhibition of IL-2 Secretion Induced by a T Cell Stimulatory Compound at the $IC_{50}$

| Identifier | $IC_{50}$ (nM) |
|---|---|
| SEQ ID NO: 3 - HEK | $4.6 \times 10^0$ |
| SEQ ID NO: 9 - HEK | $5.0 \times 10^3$ |
| SEQ ID NO: 10 - HEK | $6.2 \times 10^5$ |
| hIgG | $>1.0 \times 10^6$ |

Table 5 shows that SEQ ID NO: 3 exhibited significantly greater inhibition of T cell activation compared to SEQ ID NO: 9 and SEQ ID NO: 10. Without wishing to be bound by theory, it is believed that the C-chain of SEQ ID NO: 9 and SEQ ID NO: 10 (i) reduces their ability to bind to the insulin+ B cell receptor (mAb125) in vitro (see Example 18), and (ii) because of their relatively weak interaction with the B cell receptors, are likely unable to be as efficiently be processed and presented by 125Tg B cells, thus accounting for the decreased inhibition of insulin peptide-specific T cells co-incubated with SEQ ID NO: 5 compared to that observed with SEQ ID NO: 3.

These results demonstrate that the insulin-Fc fusion proteins of the present technology are useful in methods for treating or preventing an autoimmune disease (e.g., autoimmune diabetes, e.g., Type 1 diabetes).

Example 18: In Vitro Insulin+ B Cell Deletion Assay (125Tg NOD Cells)

To assess the ability of the insulin-Fc fusion proteins of the present technology to specifically delete insulin+ B cells, an in vitro assay was developed using 125Tg NOD mouse splenocytes and primary rat alveolar macrophages (AMs, lung lavage) or mouse macrophages (MMs from bone marrow) from animals bred at Akston Biosciences (Beverly, Mass.). The spleens were harvested, the erythrocytes were lysed, and the splenocytes purified by Ficoll prep to obtain a purified mixture of T cells and B cells. The advantage of the 125Tg NOD model is that approximately 30-80% of the splenocytes are insulin$^+$ B cells, which facilitates experimental testing. The purified splenocyte mixture was then co-cultured with rat AMs or MMs over a period of three days ($5 \times 10^5$ splenocytes with $5 \times 10^4$ AMs or MMs per 96-microtiter well) along with varying concentrations of an exemplary insulin-Fc fusion protein and control. After incubation, the cells were washed repeatedly and incubated overnight in fresh medium to ensure complete removal of the exemplary insulin-Fc fusion protein. Cells were then harvested and labeled with a cocktail of 1 µg anti-B220-PE mAb, 0.7 µg anti-IgM-PECy7 mAb, and 5 µL of RHI-µBeads (made using RHI (Sigma-Aldrich Corporation, St. Louis, Mo.) and a NHS-activated microbead using a standard kit (Miltenyi Biotec, Cambridge, Mass.)) followed by labeling with anti-µBead-APC mAb (Miltenyi Biotec, Cambridge, Mass.). Cells were fixed after washing and analyzed by FACS.

FACS analysis was performed in a four-color 2-laser FACSCalibur® flow cytometer using CellQuest Pro software (BD Biosciences, San Jose, Calif.). Live lymphocytes were gated in a FSC vs. SSC scatter and the gated lymphocytes were analyzed in FL2 vs. FL4 dot plot to enumerate the B220$^+$ B cells and B220$^+$/insulin$^+$ B cells (insulin-specific B cells) using quadrant stats. The quadrant gating of insulin and insulin(-) populations were set based on the B220(-) insulin(-) population levels and on the inhibition control samples (inhibited by adding unlabeled RHI prior to labeling of the cells). The B cell receptor density on the B cells was also estimated using the median fluorescent intensity (MFI) of anti-IgM-PECy7 in a FL2 vs. FL3 dot plot.

Table 6 describes the qualitative scoring scheme used. RHI was used as a negative control.

TABLE 6

Qualitative Scoring Rubric for In Vitro Insulin$^+$ B Cell Deletion

| Qualitative Scoring | Number of test compound serial dilutions that result in >50% of insulin$^+$ B cell deletion (as % of total B cells) for given test compound concentration |
|---|---|
| − | Zero |
| + | 1 |
| ++ | 2 |
| +++ | 3 |
| ++++ | 4 or greater |

Figure 11:
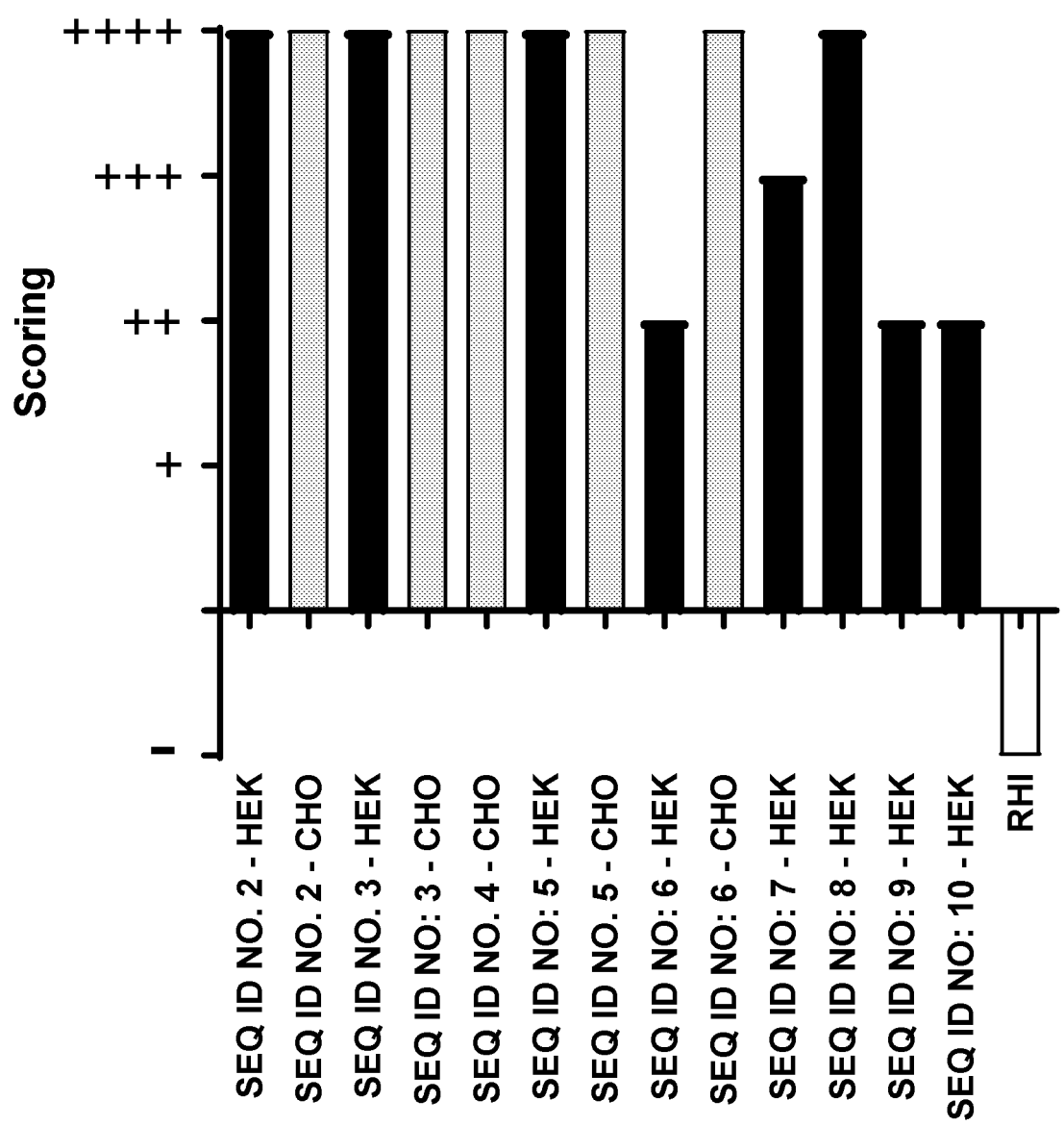
FIG. 11 is a graph showing qualitative scoring of insulin-specific 125Tg B cell deletion effectiveness for several insulin-Fc fusion proteins (SEQ ID NOs: 2, 3, 4, 5, 6, 7, 8, 9, and 10) in addition to RHI as a control.

FIG. 11 shows the effectiveness of various insulin-Fc fusion proteins (SEQ ID NOs: 2-10) in deleting insulin-specific 125Tg B cells. As shown in FIG. 11, the insulin-Fc fusion proteins of the present technology (SEQ ID NOs: 2-8) were significantly more effective at deleting insulin-specific B cells than SEQ ID NO: 9 and SEQ ID NO: 10 (which contain longer C-peptide chains, i.e. "AAAK" (SEQ ID NO: 17) and "AAAAK" (SEQ ID NO. 18) versus "AAK" (SEQ ID NO: 16)).

These results demonstrate that the insulin-Fc fusion proteins of the present technology are useful in methods for treating or preventing an autoimmune disease (e.g., autoimmune diabetes, e.g., Type 1 diabetes).

Example 19: Insulin-Specific B Cell Receptor Binding ELISA

Monoclonal antibody mAb125 (Clone AE9D6 ATCC # HB-125) is a soluble version of surface IgM (B Cell Receptor) of 125Tg transgenic mice, and can therefore be used for binding insulin or insulin-Fc fusion proteins to measure their binding properties to insulin-specific B cell receptors. mAb125 is made in vivo using ascites production in nude mice and purified via Protein G affinity chromatography using methods known in the art. mAb125 coated on ELISA plates was used to bind serial dilutions of insulin-Fc fusion proteins against a fixed amount of biotin-labeled recombinant human insulin (RHI) in a competitive-inhibition ELISA format to determine the relative efficiency of binding to mAb125 (a surrogate B cell receptor (BCR)) which was quantified by their IC$_{50}$ values (calculated by plotting the data and fitting the resulting curves using GraphPad Prism (GraphPad Software, La Jolla, Calif.)). 96-well MaxiSorp plates were coated with 10 µg/mL of mAb125 for 1 hour at room temperature (RT), and then washed and blocked with SuperBlock blocking solution (ThermoFisher, Waltham, Mass.) 250 µL/well overnight at 4° C. Eight serial dilutions of insulin-Fc fusion proteins were prepared ranging from 75 µg/mL to 34 ng/mL for testing in PBS buffer containing 0.1% Tween-80 and 10% v/v SuperBlock (PBST/SB10). 120 µL of serial dilutions of each compound was mixed with 6 µL of 1.5 ng/mL biotin-RHI (20×) in 1.2 mL tubes and 100 µL of these mixed solutions were quickly added to mAb125 coated plates using a multichannel pipettor. Plates were incubated for 1 hour at RT and then washed using a plate washer (Biotek, Winooski, Vt.) to remove unbound reagents. 100 µL/well 1:20,000 diluted Streptavidin-HRP (Thermo Fisher Scientific, Waltham, Mass.) was added to the wells and incubated for 1 hour. Plates were washed again using plate washer, and 100 µL/well TMB solution (Life Technologies, Carlsbad, Calif.) was added to the plate. After 5-15 min, the color development was stopped by adding 100 µL of ELISA stop solution (Boston Bioproducts, Ashland, Mass.) to all wells. Plates were read on microplate reader (SpectraMax190, Molecular Devices, Sunnyvale, Calif.) at OD450 nm. The OD values were used to calculate % inhibition of binding of biotin-RHI, and IC$_{50}$ values were calculated using GraphPad Prism.

Figure 12:
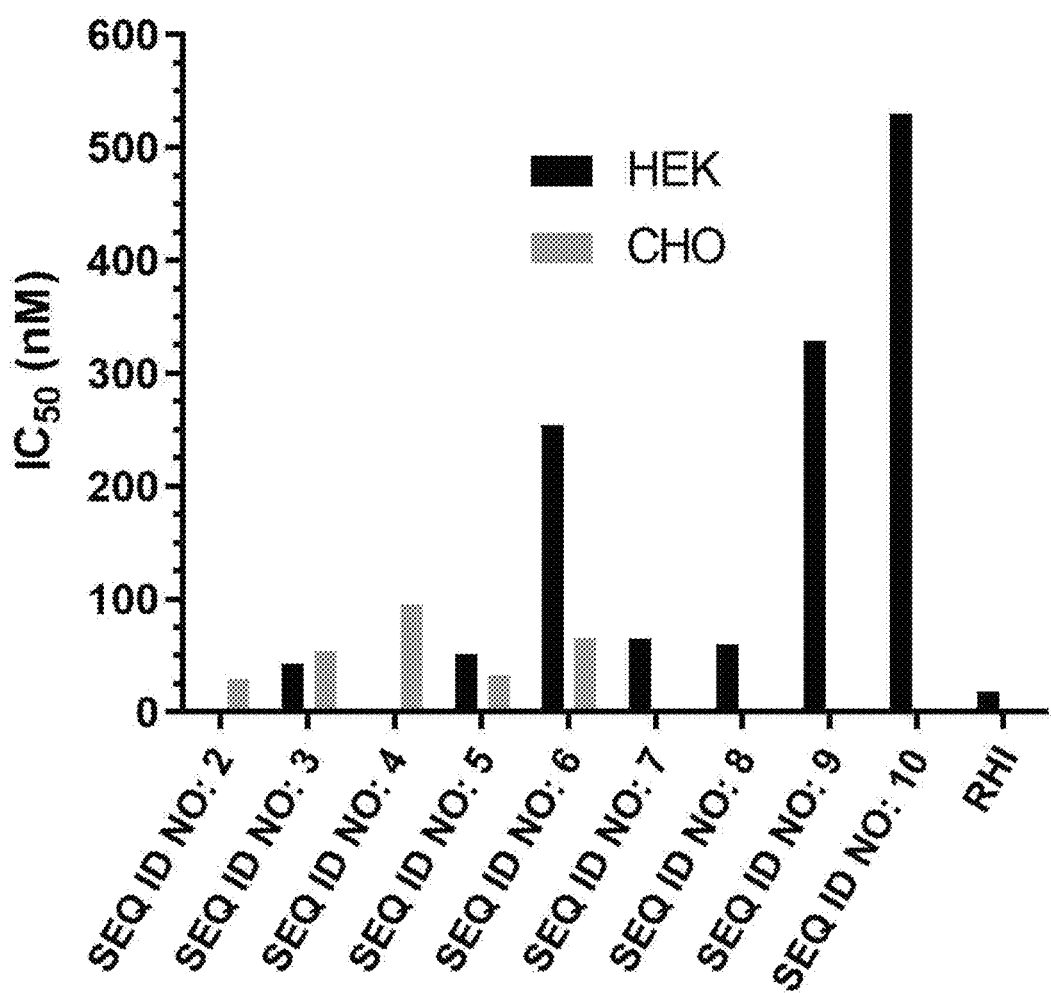
FIG. 12 is a graph showing the inhibition of biotin labelled-insulin binding to an antibody form of a cloned insulin-specific B cell receptor (mAb125) for several insulin-Fc fusion proteins (SEQ ID NOs: 2, 3, 4, 5, 6, 7, 8, 9, and 10) in addition to RHI as a control.

FIG. 12 is a graph showing the inhibition of biotin labelled-insulin binding to an antibody form of a cloned insulin$^+$ B cell receptor (mAb125) for several insulin-Fc fusion proteins (SEQ ID NOs: 2, 3, 4, 5, 6, 7, 8, 9, and 10 in addition to RHI as a control). As shown in FIG. 12, the insulin-Fc fusion proteins of the present technology (SEQ ID NOs: 2-8) significantly inhibited the binding of biotin labelled-insulin to the insulin-specific B cell receptor and in some instances exhibited inhibitory activity that was comparable to that observed with RHI (positive control). In contrast, SEQ ID NOs: 9, and 10 were less effective in inhibiting the binding of biotin labelled-insulin to the insulin-specific B cell receptor.

These results demonstrate that the insulin-Fc fusion proteins of the present technology are useful in methods for treating or preventing an autoimmune disease (e.g., autoimmune diabetes, e.g., Type 1 diabetes).

Example 20: Insulin Receptor Binding Assay

The insulin receptor binding assay is a competitive binding assay designed to assess the ability of the insulin-Fc fusion proteins disclosed herein to bind to insulin receptors present on the surface of human IM-9 cells (ATCC # CCL-159). Seven serial dilutions of insulin-Fc fusion proteins and control recombinant human insulin (RHI) diluted in FACS staining buffer were pre-mixed with a fixed concentration of biotinylated-RHI and then added to IM-9 cells and incubated on ice to allow competitive binding to occur with insulin receptors present on the cells. Resulting bound biotinylated-RHI was then labeled by streptavidin-PE reagent and fluorescent intensity of labeled receptors was analyzed in a FACSCalibur flow cytometer. IM-9 cells were grown in complete RPMI-10 medium (RPMI with 10% fetal bovine serum, 25 mM HEPES, and 50 µg/mL Gentamycin) in log growth phase in T75 culture flasks, harvested on the day of culture in 50 mL tubes, centrifuged at 250×g for 10 min and resuspended in cold FACS staining medium (HBSS/2 mMEDTA/Na-azide/4% horse serum) to a concentration of $2\times10^6$ cells/mL and kept on ice.

Biotinylated-RHI was prepared at 10 µg/mL in cold FACS staining medium and 5 µL of this solution was added per well in a V-bottom 96 well plate placed on ice. The test compounds were serially diluted (1:3) in cold FACS staining medium to seven molar concentrations (784 nM, 261 nM, 87 nM, 29 nM, 9.7 nM, 3.2 nM and 1.1 nM) in tubes. RHI was serially diluted from 192 nM to 0.26 nM. 50 µL of the serial dilutions of each test compound was added to wells containing the biotinylated-RHI and the contents were mixed in a plate shaker and then placed on ice. 50 µL of IM-9 cell suspension at $2\times10^6$ cells/mL was then added using a multichannel pipettor to all wells and contents were mixed again on a plate shaker and incubated on ice for 30 minutes. Cells were then washed twice with cold MACS buffer (HBSS/2 mM EDTA/Na-azide/0.5% horse serum) by centrifuging at 3000 rpm for 3 minutes at 4° C. and aspirating the supernatant. Cells were resuspended again in 50 µL/well cold FACS medium containing 1:100 diluted streptavidin-PE and incubated on ice for 20 min. Cells were finally washed once with cold MACS buffer and then fixed with 3% paraformaldehyde. Cells were analyzed in a FACSCalibur flow cytometer and FL-2 MFI for each sample tube was analyzed. The percent (%) inhibition by test compounds of biotinylated-RHI binding to insulin receptors on IM-9 cells was plotted against log concentrations of each test compounds and $IC_{50}$ values were calculated in GraphPad Prism (GraphPad Software, La Jolla, Calif.). Lower $IC_{50}$ values of test compounds were reflective of stronger binding to insulin receptors.

Table 7 shows the inhibition of biotin labelled-insulin binding to IM-9 insulin receptor ($IC_{50}$; nM) for several insulin-Fc fusion proteins (SEQ ID NOs: 2, 3, 4, 5, 6, 7, 8, 9, and 10) and RHI (control). As shown in Table 7, the insulin-Fc fusion proteins SEQ ID NO: 2, SEQ ID NO: 3, SEQ ID NO: 4, SEQ ID NO: 5, SEQ ID NO: 6, SEQ ID NO: 7, and SEQ ID NO: 8 do not interfere with the binding of biotin labelled-insulin to the IM-9 insulin-hormone receptor, and therefore bind the insulin receptor present on IM-9 cells very weakly or not at all, which minimizes their chances of lowering blood sugar in vivo. This is an advantageous property for treating patients with an autoimmune disease (e.g., pre-diabetic patients, patients with insulin autoantibodies, or recent-onset type 1 diabetic patients), who may have normal or slightly elevated blood sugar levels and would be susceptible to the risk of potential hypoglycemia (e.g. low blood sugar) induced by therapy with insulin-Fc fusion proteins that are able to bind the insulin receptor with $IC_{50}$ values <3,000 nM in this assay (e.g. SEQ ID NO: 9, SEQ ID NO: 10, or proteins with even higher binding affinities with $IC_{50}$ values <1,000 nM in this assay).

TABLE 7

Inhibition of biotin labelled-insulin binding to IM-9 Insulin Receptor

| Identifier | Cell Type | $IC_{50}$ (nM) |
| --- | --- | --- |
| SEQ ID NO: 2 | HEK | >5000 |
|  | CHO | >5000 |
| SEQ ID NO: 3 | HEK | >5000 |
|  | CHO | >5000 |
| SEQ ID NO: 4 | HEK | DNM |
|  | CHO | >5000 |
| SEQ ID NO: 5 | HEK | >5000 |
|  | CHO | >5000 |
| SEQ ID NO: 6 | HEK | >5000 |
|  | CHO | >5000 |
| SEQ ID NO: 7 | HEK | >5000 |
|  | CHO | DNM |
| SEQ ID NO: 8 | HEK | >5000 |
|  | CHO | DNM |
| SEQ ID NO: 9 | HEK | 2560 |
|  | CHO | DNM |
| SEQ ID NO: 10 | HEK | 1160 |
|  | CHO | DNM |
| RHI | N/A | 18 |

DNM = Did not measure

These results demonstrate that the insulin-Fc fusion proteins of the present technology are useful in methods for treating or preventing an autoimmune disease (e.g., autoimmune diabetes, e.g., Type 1 diabetes).

Example 21: SEQ ID NOs: 2-4 Prevent Diabetes in Wild Type NOD Mice

This Example demonstrates that the insulin-Fc fusion proteins of the present technology are useful in methods for preventing an autoimmune disease (e.g., autoimmune diabetes, e.g., Type 1 diabetes).

The study was initiated with 3-week old, wild type NOD female mice (n=15 per group) as follows. NOD female mice were treated twice-weekly (2 mg/kg, intraperitoneal injection (i.p.)) with an insulin-Fc fusion protein (SEQ ID NO: 3—treatment group) or with vehicle control (saline plus 0.02% Tween-80), and in some cases, a mouse $IgG_1$ isotype control (secreted and purified from cell line # CC9C10). Treatment duration was noted in the test study results. Blood glucose levels were measured at least one time per week using a handheld AlphaTRAK glucometer (Abbott, Abbott Park, Ill.). T1D was diagnosed after two successive weekly blood glucose readings >240 mg/dL.

The diabetes incidence data was converted into a Kaplan-Meier survival curve format to perform a statistical comparison of diabetes incidence between the treatment group and control groups (vehicle and $IgG_1$ isotype control), using the log-rank test with p<0.05 indicating statistical significance.

Figure 13:
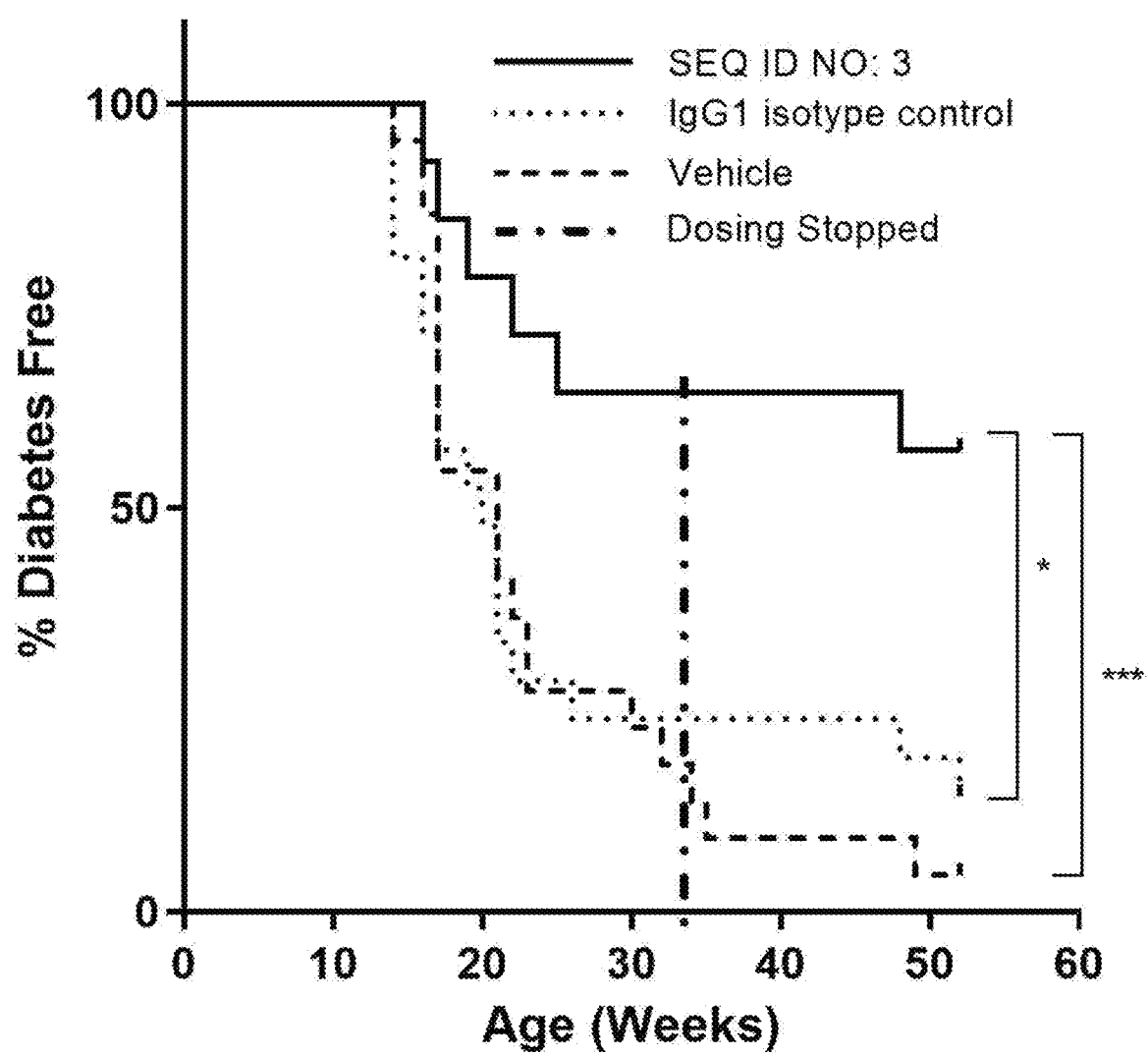
FIG. 13 shows a Kaplan-Meier survival curve for the development of T1D in female 3-week old wild type NOD mice (n=15 in each treatment group) treated with an exemplary insulin-Fc fusion protein (SEQ ID NO: 3).
Figure 14:
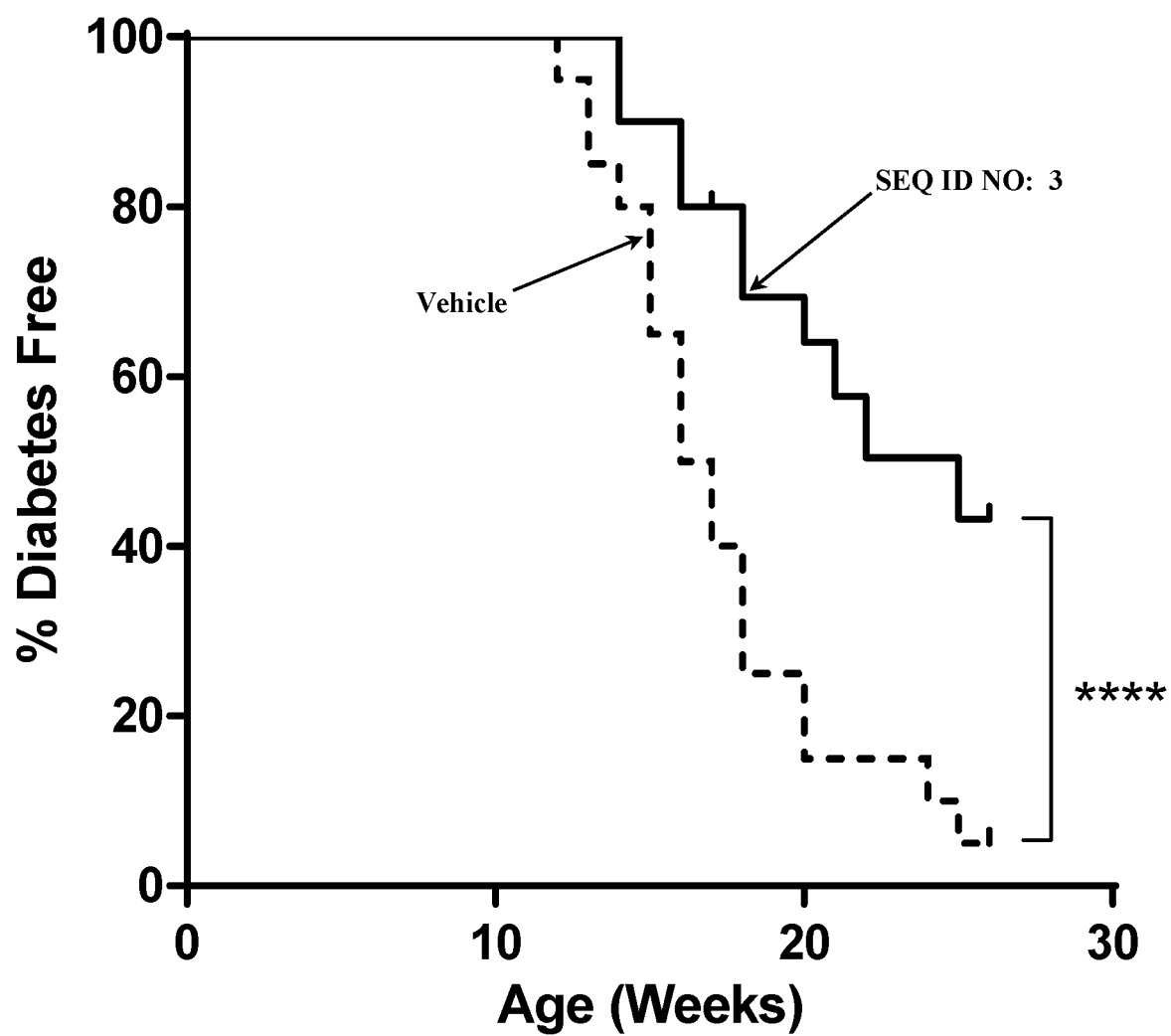
FIG. 14 shows a Kaplan-Meier survival curve for the development of T1D in female 3-week old wild type NOD mice (n=20 in each treatment group) treated with an exemplary insulin-Fc fusion protein (SEQ ID NO: 3).

FIG. 13 shows a statistically significant (p≤0.05 versus $IgG_1$ isotype control; p≤0.001 versus vehicle control) decrease in T1D development at 49 weeks of age in the treatment group which received SEQ ID NO: 3 (22% conversion) compared to the control group (55% conversion). Dosing was stopped at 34 weeks of age. These results were confirmed in a subsequent blinded study. See FIG. 14 (showing a statistically significant difference (p≤0.0001) in diabetes prevention between the treatment group which received SEQ ID NO: 3 (56% conversion) vs. the control group (94% conversion) at 26 weeks of age).

Figure 15:
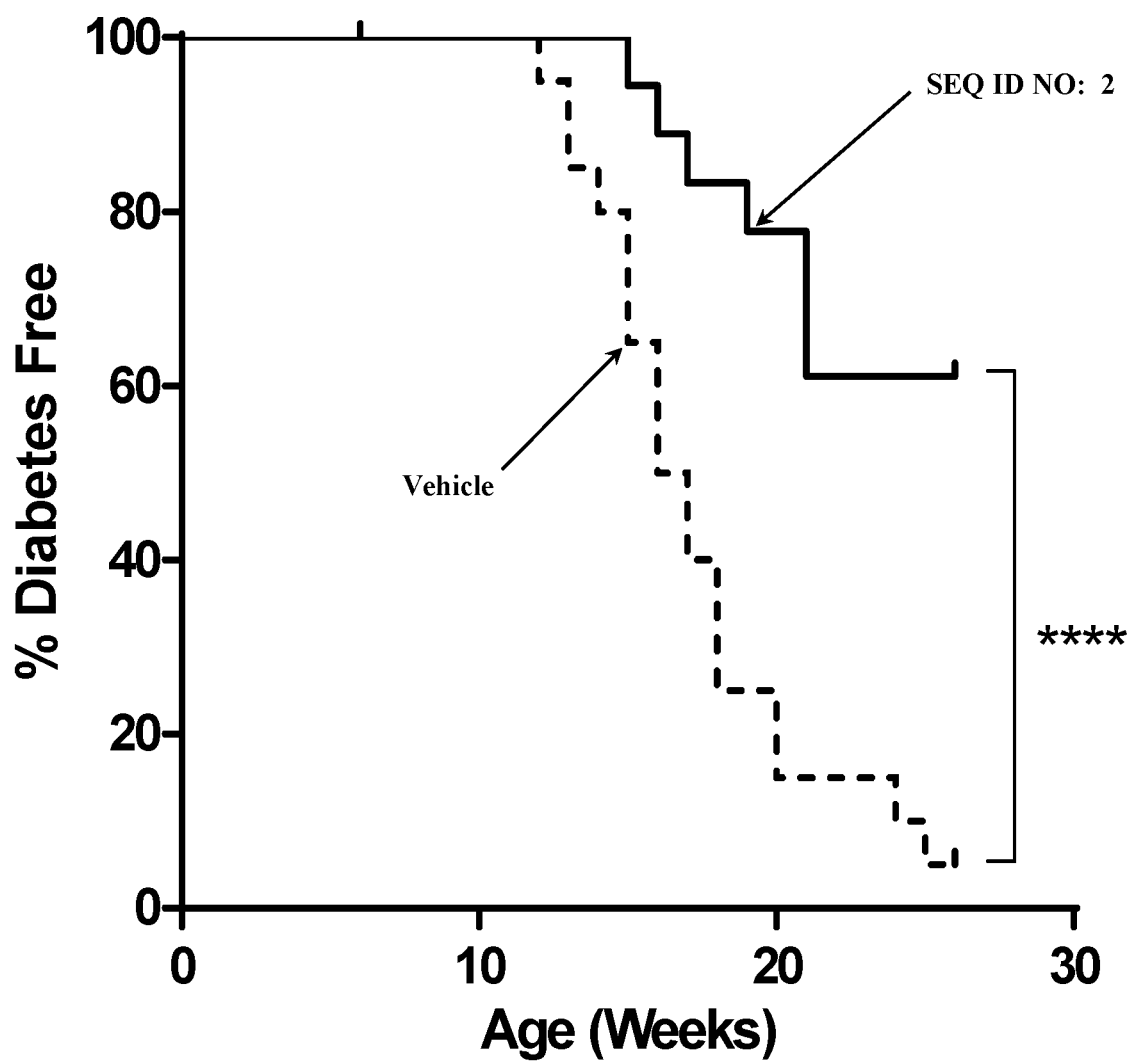
FIG. 15 shows a Kaplan-Meier survival curve for the development of T1D in female 3-week old wild type NOD mice (n=20 in each treatment group) treated with an exemplary insulin-Fc fusion protein (SEQ ID NO: 2).
Figure 16:
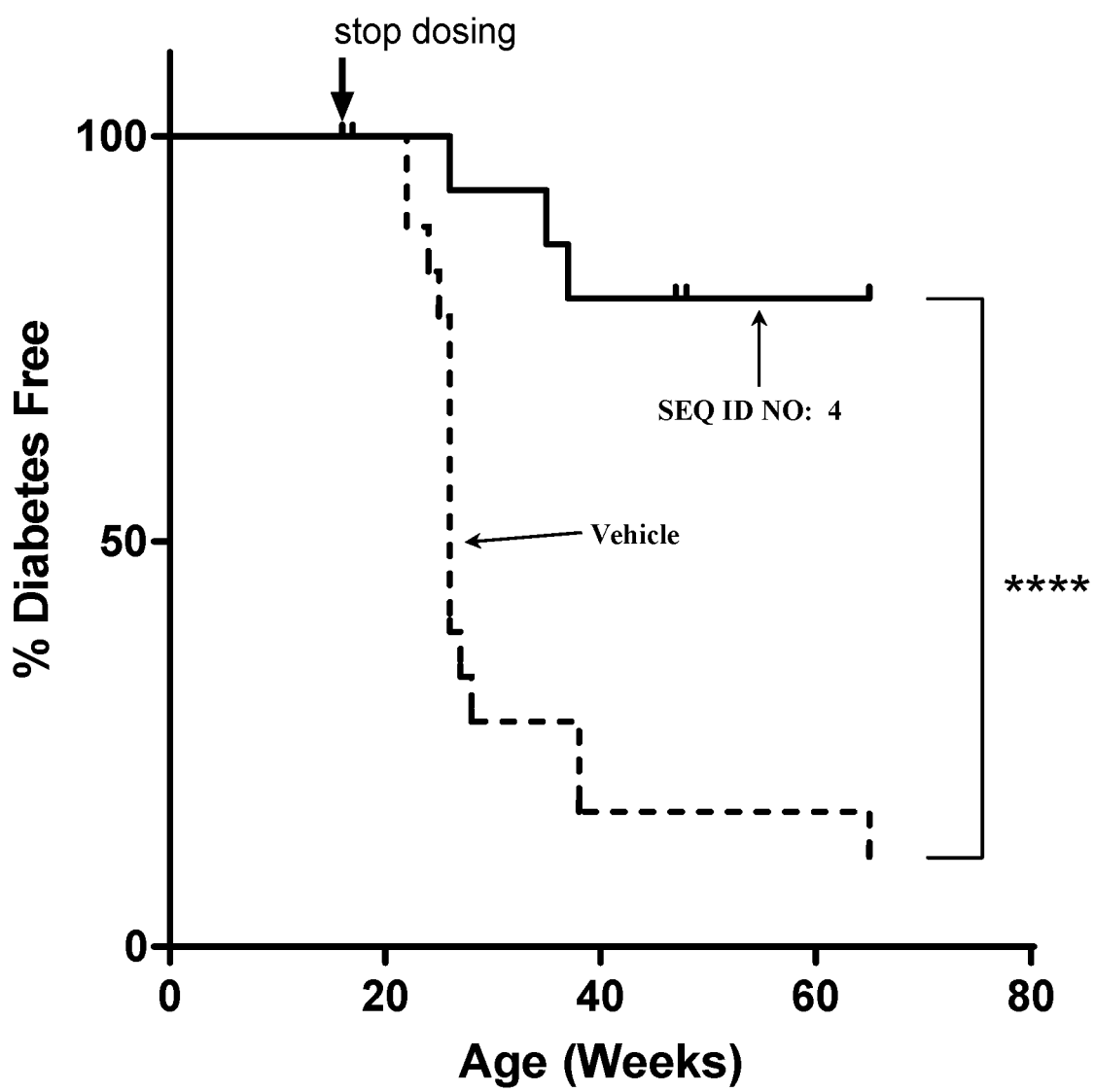
FIG. 16 shows a Kaplan-Meier survival curve for the development of T1D in female 3-week old wild type NOD mice (n=18 in each treatment group) treated with an exemplary insulin-Fc fusion protein (SEQ ID NO: 4).

FIG. 15 shows a statistically significant difference (p≤0.0001) in diabetes prevention between the treatment group which received SEQ ID NO: 2 (40% conversion) vs. the control group (94% conversion) at 26 weeks of age. FIG. 16 shows a statistically significant (p≤0.0001) decrease in T1D development at 68 weeks of age in the treatment group which received SEQ ID NO: 4 (22% conversion) vs. the control group (85% conversion). Dosing was stopped at 18 weeks of age in this study.

These results demonstrate that the insulin-Fc fusion proteins of the present technology are useful in methods for preventing an autoimmune disease (e.g., autoimmune diabetes, e.g., Type 1 diabetes).

Example 22: SEQ ID NOs: 5-8 Prevent Diabetes in Wild Type NOD Mice

This Example demonstrates that the insulin-Fc fusion proteins of the present technology are useful in methods for preventing an autoimmune disease (e.g., autoimmune diabetes, e.g., Type 1 diabetes).

A further study will be conducted with 3-week old, wild type NOD female mice (n=15 per group) to evaluate other exemplary sequences. NOD female mice are treated twice-weekly (2 mg/kg, intraperitoneal injection (i.p.)) with an insulin-Fc fusion protein (one of SEQ ID NO: 5, SEQ ID NO: 6, SEQ ID NO: 7, SEQ ID NO: 8, SEQ ID NO: 9 or SEQ ID NO: 10) or with saline or vehicle controls. Treatment duration is carried out to between 26 and 60 weeks of age. Blood glucose levels are measured at least one time per week using a handheld AlphaTRAK glucometer (Abbott, Abbott Park, Ill.). T1D is diagnosed after two successive weekly blood glucose readings >240 mg/dL. The diabetes incidence data will be converted into a Kaplan-Meier survival curve format to perform a statistical comparison of diabetes incidence between the treatment group and control groups (vehicle or saline controls), using the log-rank test with p<0.05 indicating statistical significance.

It is predicted that SEQ ID NO: 5, SEQ ID NO: 6, SEQ ID NO: 7 and SEQ ID NO: 8 will prevent T1D phenotypes similar to that observed with SEQ ID NO: 2 (FIG. 15), SEQ ID NO: 3 (FIG. 13 and FIG. 14) and SEQ ID NO: 4 (FIG. 16). It is also predicted that SEQ ID NO: 9 and SEQ ID NO: 10 will be less effective in preventing T1D.

These results demonstrate that the insulin-Fc fusion proteins of the present technology are useful in methods for preventing an autoimmune disease (e.g., autoimmune diabetes, e.g., Type 1 diabetes).

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

---

The invention claimed is:

1. An insulin-Fc fusion protein comprising an insulin polypeptide fused to a Fc domain, wherein the insulin polypeptide comprises a B-chain peptide, a C-chain peptide, and an A-chain peptide, wherein the amino acid sequence of the C-chain peptide is AAK (SEQ ID NO: 16), and optionally wherein the insulin-Fc fusion protein binds human insulin receptor at an $IC_{50}>5{,}000$ nM in a competitive binding assay, wherein the B-chain peptide comprises the amino acid sequence FVNQHLCGSHLV$X_1$AL$X_2$LVCGE$X_3$GFFYTPK (SEQ ID NO: 28), wherein $X_1$ is E, $X_2$ is A, and $X_3$ is R.

2. The insulin-Fc fusion protein of claim 1, wherein the insulin-Fc fusion protein inhibits in vitro binding of insulin B cell receptors to insulin at an $IC_{50}$≤100 nM.

3. The insulin-Fc fusion protein of claim 1, wherein the insulin-Fc fusion protein activates T-cells to secrete IL-2 levels that are reduced compared to that observed in T-cells activated by recombinant human insulin.

4. The insulin-Fc fusion protein of claim 1, wherein the amino acid sequence of the A-chain peptide comprises SEQ ID NO: 19.

5. The insulin-Fc fusion protein of claim 1, wherein the Fc domain comprises a wild-type Fc fragment of human $IgG_1$, and wherein the amino acid sequence of the Fc domain comprises SEQ ID NO: 22.

6. The insulin-Fc fusion protein of claim 1, wherein the insulin polypeptide is fused to the Fc fragment via a peptide linker, and wherein the amino acid sequence of the peptide linker is selected from the group consisting of SEQ ID NO: 20 and SEQ ID NO: 21.

7. A method for treating autoimmune diabetes in a subject in need thereof comprising administering to the subject an effective amount of the insulin-Fc fusion protein of claim 1, wherein autoimmune diabetes is selected from the group consisting of Type 1 diabetes, juvenile diabetes, insulin-dependent diabetes, and latent autoimmune diabetes;

wherein the subject has been diagnosed with or is at risk for autoimmune diabetes; and wherein the subject is not hyperglycemic.

8. The method of claim 7, wherein the subject has detectable levels of at least one autoimmune antibody selected from the group consisting of an insulin autoantibody (IAA), an anti-glutamic acid decarboxylase (GAD) antibody, and an anti-islet antigen-2 (IA-2) antibody, and wherein the subject has detectable levels of an insulin-specific B cell population.

9. The method of claim 7, wherein the subject harbors one or more human leukocyte antigen (HLA) haplotypes selected from the group consisting of: (a) DRB1*0301-DQA1*0501-DQB1*0201; (b) DRB1*0405-DQA1*0301-DQB1*0302; (c) DRB1*0401-DQA1*0301-DQB*0302; (d) DRB1*0402-DQA1*0301-DQB1*0302; (e) DRB1*0404-DQA1*0301-DQB1*0302; and (f) DRB1*0801-DQB1*0401-DQB1*0402.

10. The method of claim 7, wherein the subject displays a reduction in the number of anti-insulin B cells after at least one administration of the insulin-Fc fusion protein compared to that observed in the subject prior to the at least one administration, wherein the subject displays decreased levels of insulin autoantibody after the at least one administration of the insulin-Fc fusion protein compared to that observed in the subject prior to the at least one administration; and wherein blood glucose levels of the subject after at least one administration of the insulin-Fc fusion protein are comparable to that observed in the subject prior to the at least one administration.

11. An insulin-Fc fusion protein comprising an insulin polypeptide fused to a Fc domain, wherein the insulin polypeptide comprises a B-chain peptide, a C-chain peptide, and an A-chain peptide, wherein the B-chain peptide comprises the amino acid sequence FVNQHLCGSHLV$X_1$AL$X_2$LVCGE$X_3$GFFYTPK (SEQ ID NO: 28), wherein $X_1$ is E, $X_2$ is A, and $X_3$ is R; and wherein the amino acid sequence of the C-chain peptide is AAK (SEQ ID NO: 16).

12. The insulin-Fc fusion protein of claim 11, wherein the amino acid sequence of the A-chain peptide comprises SEQ ID NO: 19.

13. The insulin-Fc fusion protein of claim 11, wherein the Fc domain comprises a wild-type Fc fragment of human $IgG_1$, and wherein the amino acid sequence of the Fc domain comprises SEQ ID NO: 22.

14. The insulin-Fc fusion protein of claim 11, wherein the insulin polypeptide is fused to the Fc fragment via a peptide linker, and wherein the amino acid sequence of the peptide linker is selected from the group consisting of SEQ ID NO: 20 and SEQ ID NO: 21.

15. The insulin-Fc fusion protein of claim 11, wherein the amino acid sequence of the insulin-Fc fusion protein is SEQ ID NO: 3.

16. The insulin-Fc fusion protein of claim 11, wherein the insulin-Fc fusion protein inhibits in vitro binding of $insulin^+$ B cell receptors to insulin at an $IC_{50}$≤100 nM.

17. The insulin-Fc fusion protein of claim 11, wherein the insulin-Fc fusion protein activates T-cells to secrete IL-2 levels that are reduced compared to that observed in T-cells activated by recombinant human insulin.

* * * * *